United States Patent
Nunn et al.

(10) Patent No.: US 11,865,298 B2
(45) Date of Patent: Jan. 9, 2024

(54) SYSTEMS AND TECHNIQUES FOR GENERATING, INFUSING, AND CONTROLLING RADIOISOTOPE DELIVERY

(71) Applicant: BRACCO DIAGNOSTICS INC., Monroe Township, NJ (US)

(72) Inventors: Adrian Nunn, Lambertville, NJ (US); Clif Moyers, Oak Ridge, TN (US); Andrew Schimmoeller, Plain City, OH (US); Brian Cherundolo, White Marsh, MD (US); Tarah Bolas, Knoxville, TN (US)

(73) Assignee: Bracco Diagnostics Inc., Monroe Township, NJ (US)

( * ) Notice: Subject to any disclaimer, the term of this patent is extended or adjusted under 35 U.S.C. 154(b) by 1029 days.

(21) Appl. No.: 16/334,887

(22) PCT Filed: Sep. 20, 2017

(86) PCT No.: PCT/US2017/052537
§ 371 (c)(1),
(2) Date: Mar. 20, 2019

(87) PCT Pub. No.: WO2018/057636
PCT Pub. Date: Mar. 29, 2018

(65) Prior Publication Data
US 2020/0030523 A1    Jan. 30, 2020

Related U.S. Application Data

(60) Provisional application No. 62/397,025, filed on Sep. 20, 2016, provisional application No. 62/397,022, (Continued)

(51) Int. Cl.
*A61M 5/00* (2006.01)
*A61K 51/12* (2006.01)
(Continued)

(52) U.S. Cl.
CPC .......... *A61M 5/007* (2013.01); *A61K 51/121* (2013.01); *A61K 51/1282* (2013.01); (Continued)

(58) Field of Classification Search
CPC .............. A61K 51/121; A61K 51/1282; A61K 2123/00; A61M 5/007; A61M 5/1408; (Continued)

(56) References Cited

U.S. PATENT DOCUMENTS 3,483,867 A    12/1969 Markovitz
3,535,085 A    10/1970 Shumate
(Continued)

FOREIGN PATENT DOCUMENTS

AT    399241 B  *  2/1995    ............. G21G 4/08
CA    2913373 A1    4/2008
(Continued)

OTHER PUBLICATIONS

Patent Translate: Translation of patent Jungmann (AT 399241) (Year: 1995).*
(Continued)

*Primary Examiner* — Nilay J Shah
(74) *Attorney, Agent, or Firm* — Fredrikson & Bryon, P.A.

(57) ABSTRACT

An infusion system may include a strontium-rubidium radioisotope generator that generates a radioactive eluate via elution, a beta detector, a gamma detector, and a controller. The beta detector and the gamma detector may be positioned to measure beta emissions and gamma emissions, respectively, emitted from the radioactive eluate. In some examples, the controller is configured to determine an activity of rubidium in the radioactive eluate based on the beta emissions measured by the beta detector and determine an
(Continued)

activity of strontium in the radioactive eluate based on the gamma emissions measured by the gamma detector.

38 Claims, 21 Drawing Sheets

Related U.S. Application Data filed on Sep. 20, 2016, provisional application No. 62/397,026, filed on Sep. 20, 2016.

(51) Int. Cl.

| | |
|---|---|
| *G21F 5/015* | (2006.01) |
| *G21G 1/00* | (2006.01) |
| *G21G 4/08* | (2006.01) |
| *A61M 5/14* | (2006.01) |
| *A61M 5/162* | (2006.01) |
| *A61M 5/168* | (2006.01) |
| *G01T 1/20* | (2006.01) |
| *G21H 5/02* | (2006.01) |
| *G01T 7/00* | (2006.01) |
| *A61N 5/10* | (2006.01) |
| *A61M 5/142* | (2006.01) |
| *G01T 1/16* | (2006.01) |

(52) U.S. Cl.
CPC .......... *A61M 5/142* (2013.01); *A61M 5/1408* (2013.01); *A61M 5/162* (2013.01); *A61M 5/16827* (2013.01); *A61M 5/16881* (2013.01); *A61N 5/1007* (2013.01); *G01T 1/20* (2013.01); *G01T 7/005* (2013.01); *G21F 5/015* (2013.01); *G21G 1/0005* (2013.01); *G21G 4/08* (2013.01); *G21H 5/02* (2013.01); *A61K 2123/00* (2013.01); *A61M 2205/18* (2013.01); *A61M 2205/3313* (2013.01); *A61M 2205/3389* (2013.01); *A61M 2205/702* (2013.01); *A61N 2005/1021* (2013.01); *G01T 1/1603* (2013.01); *G21G 2001/0031* (2013.01)

(58) Field of Classification Search
CPC .......... A61M 5/16827; A61M 5/16881; A61M 2205/18; A61M 2205/3389; A61M 2205/3313; A61M 2205/702; G01T 1/20; G01T 7/005; G21F 5/015; G21G 1/0005; G21G 2001/0031; G21G 4/08; G21H 5/02
See application file for complete search history.

(56) References Cited

U.S. PATENT DOCUMENTS

| | | | |
|---|---|---|---|
| 3,543,752 A | 12/1970 | Hesse et al. | |
| 3,565,376 A | 2/1971 | Viers | |
| 3,576,998 A | 5/1971 | Deutsch et al. | |
| 3,710,118 A | 1/1973 | Holgate et al. | |
| 3,714,429 A | 1/1973 | Mozley et al. | |
| 3,767,915 A * | 10/1973 | Battist | G01T 7/02 250/369 |
| 3,774,036 A | 11/1973 | Gerhart | |
| 3,847,138 A | 11/1974 | Gollub | |
| 3,861,380 A | 1/1975 | Chassagne | |
| 3,953,567 A | 4/1976 | Grant et al. | |
| 3,991,960 A | 11/1976 | Tanaka | |
| 3,997,784 A | 12/1976 | Picunko et al. | |
| 4,096,859 A | 6/1978 | Agarwal et al. | |
| 4,160,910 A | 7/1979 | Thornton et al. | |
| 4,212,303 A | 7/1980 | Nolan | |
| 4,239,970 A | 12/1980 | Eckhardt et al. | |
| 4,241,728 A | 12/1980 | Mirell | |
| 4,286,169 A | 8/1981 | Rossem | |
| 4,336,036 A | 6/1982 | Leeke et al. | |
| 4,406,877 A | 9/1983 | Neirinckx et al. | |
| 4,466,888 A | 8/1984 | Verkaart | |
| 4,562,829 A * | 1/1986 | Bergner | A61M 5/172 600/432 |
| 4,585,009 A | 4/1986 | Barker et al. | |
| 4,585,941 A | 4/1986 | Bergner | |
| 4,597,951 A | 7/1986 | Gennaro et al. | |
| 4,623,102 A | 11/1986 | Hough, Jr. | |
| 4,624,661 A | 11/1986 | Arimond | |
| 4,625,118 A | 11/1986 | Kriwetz et al. | |
| 4,656,697 A | 4/1987 | Naeslund | |
| 4,674,403 A | 6/1987 | Bryant et al. | |
| 4,679,142 A | 7/1987 | Lee | |
| 4,755,679 A | 7/1988 | Wong | |
| 4,759,345 A | 7/1988 | Mistry | |
| 4,769,008 A | 9/1988 | Hessel | |
| 4,847,505 A | 7/1989 | Suthanthiran | |
| 4,853,546 A | 8/1989 | Abe et al. | |
| 4,859,431 A | 8/1989 | Ehrhardt | |
| 4,994,056 A | 2/1991 | Ikeda | |
| 5,039,863 A | 8/1991 | Matsuno et al. | |
| 5,092,834 A | 3/1992 | Bradshaw et al. | |
| 5,115,407 A | 5/1992 | Bird et al. | |
| 5,166,526 A | 11/1992 | Dietzel | |
| 5,223,434 A | 6/1993 | Kanno et al. | |
| 5,254,328 A | 10/1993 | Herscheid et al. | |
| 5,258,906 A | 11/1993 | Kroll et al. | |
| 5,265,133 A | 11/1993 | Matthews | |
| 5,274,239 A | 12/1993 | Lane et al. | |
| 5,284,481 A | 2/1994 | Soika et al. | |
| 5,395,320 A | 3/1995 | Padda et al. | |
| 5,468,355 A | 11/1995 | Shefer et al. | |
| 5,475,232 A | 12/1995 | Powers et al. | |
| 5,483,070 A | 1/1996 | Valenta | |
| 5,485,831 A | 1/1996 | Holdsworth et al. | |
| 5,573,747 A | 11/1996 | Lacy | |
| 5,580,541 A | 12/1996 | Wells et al. | |
| 5,590,648 A | 1/1997 | Mitchell et al. | |
| 5,674,404 A | 10/1997 | Kenley et al. | |
| 5,681,285 A | 10/1997 | Ford et al. | |
| 5,702,115 A | 12/1997 | Pool | |
| 5,739,508 A | 4/1998 | Uber, III | |
| 5,765,842 A | 6/1998 | Phaneuf et al. | |
| 5,827,429 A | 10/1998 | Ruschke et al. | |
| 5,840,026 A | 11/1998 | Uber, III et al. | |
| 5,885,216 A | 3/1999 | Evans, III et al. | |
| 5,971,923 A | 10/1999 | Finger | |
| 6,058,718 A | 5/2000 | Forsberg et al. | |
| 6,157,036 A | 12/2000 | Whiting et al. | |
| 6,220,554 B1 | 4/2001 | Daoud | |
| 6,267,717 B1 | 7/2001 | Stoll et al. | |
| 6,269,810 B1 | 8/2001 | Brooker et al. | |
| 6,327,895 B1 | 12/2001 | Jeppsson et al. | |
| 6,347,711 B1 | 2/2002 | Goebel et al. | |
| 6,442,418 B1 | 8/2002 | Evans et al. | |
| 6,450,936 B1 | 9/2002 | Smith et al. | |
| 6,454,460 B1 | 9/2002 | Ramanathan et al. | |
| 6,558,125 B1 | 5/2003 | Futterknecht | |
| 6,626,862 B1 | 9/2003 | Duchon et al. | |
| 6,639,237 B2 | 10/2003 | Pedersen et al. | |
| 6,673,594 B1 | 1/2004 | Owen et al. | |
| 6,758,975 B2 | 7/2004 | Peabody et al. | |
| 6,767,319 B2 | 7/2004 | Reilly et al. | |
| 6,773,686 B1 | 8/2004 | Herscheid et al. | |
| 6,787,030 B2 | 9/2004 | Hsi et al. | |
| 6,870,175 B2 | 3/2005 | Dell et al. | |
| 6,901,283 B2 | 5/2005 | Evans, III et al. | |
| 6,908,598 B2 | 6/2005 | Sylvester | |
| 6,931,327 B2 | 8/2005 | Goode, Jr. et al. | |
| 7,091,494 B2 | 8/2006 | Weisner et al. | |
| 7,125,166 B2 | 10/2006 | Eck et al. | |
| 7,163,031 B2 | 1/2007 | Graves et al. | |
| 7,169,135 B2 | 1/2007 | Duchon et al. | |
| 7,204,797 B2 | 4/2007 | Reilly et al. | |
| 7,256,888 B2 | 8/2007 | Staehr et al. | |
| 7,286,867 B2 | 10/2007 | Schlyer et al. | |
| 7,413,123 B2 | 8/2008 | Ortenzi | |

(56) References Cited

U.S. PATENT DOCUMENTS

| | | | |
|---|---|---|---|
| 7,476,377 B2 | 1/2009 | Moller et al. |
| 7,504,646 B2 | 3/2009 | Balestracci et al. |
| 7,522,952 B2 | 4/2009 | Krieg et al. |
| 7,586,102 B2 | 9/2009 | Mourtada et al. |
| 7,605,384 B2 | 10/2009 | Sonnenhol et al. |
| 7,608,831 B2 | 10/2009 | Lamb et al. |
| 7,612,999 B2 | 11/2009 | Clark et al. |
| 7,712,491 B2 | 5/2010 | Tochon-Danguy et al. |
| 7,734,331 B2 | 6/2010 | Dhawale et al. |
| 7,737,415 B2 | 6/2010 | Casale et al. |
| 7,780,352 B2 | 8/2010 | Fox et al. |
| 7,804,415 B2 | 9/2010 | Cheng et al. |
| 7,813,841 B2 | 10/2010 | deKemp et al. |
| 7,825,372 B2 | 11/2010 | Allberg |
| 7,862,534 B2 | 1/2011 | Quirico et al. |
| 7,996,068 B2 | 8/2011 | Telischak et al. |
| 8,058,632 B2 | 11/2011 | Balestracci et al. |
| 8,071,959 B2 | 12/2011 | deKemp |
| 8,198,599 B2 | 6/2012 | Bouton et al. |
| 8,216,181 B2 | 7/2012 | Balestracci |
| 8,216,184 B2 | 7/2012 | Balestracci |
| 8,317,674 B2 | 9/2012 | Quirico et al. |
| 8,295,916 B2 | 10/2012 | Shimchuk et al. |
| 8,431,909 B2 | 4/2013 | Horton et al. |
| 8,439,815 B2 | 5/2013 | Lemer |
| 8,442,803 B2 | 5/2013 | Chen et al. |
| 8,571,881 B2 | 9/2013 | Rousso et al. |
| 8,615,405 B2 | 12/2013 | Rousso et al. |
| 8,708,352 B2 | 4/2014 | Quirico et al. |
| 9,056,164 B2 | 6/2015 | Tate et al. |
| 9,056,200 B2 | 6/2015 | Uber, III et al. |
| 9,326,742 B2 | 5/2016 | Hirschman et al. |
| 2002/0128594 A1 | 9/2002 | Das et al. |
| 2002/0129471 A1 | 9/2002 | Wang |
| 2003/0014035 A1 | 1/2003 | Trombley, III et al. |
| 2003/0139640 A1 | 7/2003 | Whittacre et al. |
| 2003/0194894 A1 | 10/2003 | Wariar et al. |
| 2003/0216609 A1 | 11/2003 | Dell et al. |
| 2004/0054319 A1 | 3/2004 | Langley et al. |
| 2004/0104160 A1 | 6/2004 | Scagliarini et al. |
| 2004/0260143 A1 | 12/2004 | Reilly et al. |
| 2005/0029465 A1 | 2/2005 | Lemer |
| 2005/0058839 A1* | 3/2005 | Moller | A61K 51/1282 |
| | | | 423/2 |
| 2005/0085682 A1 | 4/2005 | Sasaki et al. |
| 2005/0107698 A1 | 5/2005 | Powers et al. |
| 2005/0187515 A1 | 8/2005 | Varrichio et al. |
| 2005/0277833 A1 | 12/2005 | Williams |
| 2005/0278066 A1 | 12/2005 | Graves et al. |
| 2006/0015056 A1 | 1/2006 | Ellingboe et al. |
| 2006/0151048 A1 | 7/2006 | Tochon-Danguy et al. |
| 2006/0164093 A1 | 7/2006 | Ooe et al. |
| 2006/0173419 A1 | 8/2006 | Malcolm |
| 2006/0235353 A1 | 10/2006 | Gelfand et al. |
| 2007/0080223 A1 | 4/2007 | Japuntich |
| 2007/0140958 A1 | 6/2007 | deKemp |
| 2007/0213848 A1 | 9/2007 | deKemp et al. |
| 2007/0226175 A1 | 9/2007 | Resnic et al. |
| 2007/0232980 A1 | 10/2007 | Felt et al. |
| 2007/0260213 A1 | 11/2007 | Williams et al. |
| 2007/0282263 A1 | 12/2007 | Kalafut et al. |
| 2008/0015794 A1 | 1/2008 | Eiler et al. |
| 2008/0035542 A1 | 2/2008 | Mourtada et al. |
| 2008/0071219 A1 | 3/2008 | Rhinehart et al. |
| 2008/0093564 A1 | 4/2008 | Tartaglia et al. |
| 2008/0128626 A1 | 6/2008 | Rousso et al. |
| 2008/0131362 A1 | 6/2008 | Rousso et al. |
| 2008/0152083 A1* | 6/2008 | Juni | A61B 6/037 |
| | | | 250/363.04 |
| 2008/0166292 A1 | 7/2008 | Levin et al. |
| 2008/0177126 A1 | 7/2008 | Tate et al. |
| 2008/0191148 A1 | 8/2008 | Gibson |
| 2008/0195249 A1 | 8/2008 | Rousso et al. |
| 2008/0200747 A1 | 8/2008 | Wagner et al. |
| 2008/0203318 A1 | 8/2008 | Wagner et al. |
| 2008/0224065 A1 | 9/2008 | Pollard, Jr. |
| 2008/0237502 A1 | 10/2008 | Fago |
| 2008/0242915 A1 | 10/2008 | Jackson et al. |
| 2008/0260580 A1 | 10/2008 | Helle et al. |
| 2009/0032729 A1 | 2/2009 | Piancastelli |
| 2009/0112478 A1 | 4/2009 | Mueller, Jr. et al. |
| 2009/0155167 A1 | 6/2009 | Powell et al. |
| 2009/0224171 A1 | 9/2009 | Verbokkem |
| 2009/0309465 A1* | 12/2009 | Quirico | G21F 5/015 |
| | | | 600/431 |
| 2009/0312630 A1 | 12/2009 | Hidem et al. |
| 2009/0312635 A1* | 12/2009 | Shimchuk | A61M 5/142 |
| | | | 600/3 |
| 2010/0030009 A1 | 2/2010 | Lemer |
| 2010/0312039 A1 | 12/2010 | Quirico et al. |
| 2011/0071392 A1 | 3/2011 | Quirico et al. |
| 2011/0172524 A1 | 7/2011 | Hidem et al. |
| 2011/0178359 A1 | 7/2011 | Hirschman et al. |
| 2011/0209764 A1 | 9/2011 | Uber et al. |
| 2012/0098671 A1 | 4/2012 | Wieczorek et al. |
| 2012/0305730 A1 | 12/2012 | Balestracci |
| 2012/0310031 A1 | 12/2012 | Quirico et al. |
| 2012/0312980 A1 | 12/2012 | Whitehouse |
| 2013/0300109 A1 | 11/2013 | Balestracci et al. |
| 2014/0084187 A1 | 3/2014 | Quirico et al. |
| 2014/0175959 A1 | 6/2014 | Quirico et al. |
| 2014/0343418 A1 | 11/2014 | Quirico et al. |
| 2014/0374614 A1 | 12/2014 | Hidem et al. |
| 2014/0374615 A1 | 12/2014 | Hidem et al. |
| 2015/0260855 A1 | 9/2015 | McQuaid et al. |

FOREIGN PATENT DOCUMENTS

| | | |
|---|---|---|
| CN | 1137239 A | 12/1996 |
| CN | 1431488 A | 7/2003 |
| CN | 1460849 A | 12/2003 |
| CN | 1471644 A | 1/2004 |
| CN | 2677923 Y | 2/2005 |
| CN | 1946432 A | 4/2007 |
| CN | 1968653 A | 5/2007 |
| CN | 101015459 A | 8/2007 |
| CN | 201017036 Y | 2/2008 |
| CN | 101401009 A | 4/2009 |
| CN | 101801440 A | 8/2010 |
| CN | 104332198 A | 2/2015 |
| CN | 104536031 A | 4/2015 |
| CN | 104597472 A | 5/2015 |
| DE | 19622184 A1 | 12/1997 |
| DE | 19918342 B4 | 5/2017 |
| EP | 102121 A1 | 3/1984 |
| EP | 117752 A2 | 9/1984 |
| EP | 160303 A2 | 11/1985 |
| EP | 310148 A2 | 4/1989 |
| EP | 317114 A1 | 5/1989 |
| EP | 319148 A2 | 6/1989 |
| EP | 919249 A1 | 6/1999 |
| EP | 1421960 A1 | 5/2004 |
| EP | 1772157 A1 | 4/2007 |
| EP | 1820730 A1 | 8/2007 |
| EP | 2332593 A2 | 6/2011 |
| EP | 2011126 B1 | 5/2012 |
| EP | 2492920 A2 | 8/2012 |
| EP | 2542276 A1 | 1/2013 |
| EP | 2896049 A1 | 7/2015 |
| FR | 2867084 A1 | 9/2005 |
| JP | 2000350783 A | 12/2000 |
| JP | 3137622 B1 | 2/2001 |
| JP | 2003520780 A | 7/2003 |
| JP | 2006017660 A | 1/2006 |
| JP | 2006043212 A | 2/2006 |
| JP | 2006325826 A | 12/2006 |
| JP | 2008023346 A | 2/2008 |
| JP | 2011161262 A | 8/2011 |
| KR | 960003726 B1 | 3/1996 |
| KR | 20150125046 A | 11/2015 |
| RU | 2131273 C1 | 6/1999 |
| RU | 2288755 C1 | 12/2006 |
| RU | 65383 U1 | 8/2007 |
| RU | 2429886 C2 | 9/2011 |

(56) References Cited

FOREIGN PATENT DOCUMENTS

| | | |
|---|---|---|
| RU | 2575309 C2 | 2/2016 |
| RU | 2599866 C2 | 10/2016 |
| RU | 2606169 C2 | 1/2017 |
| SU | 244513 A1 | 12/1969 |
| TW | 391868 B | 6/2000 |
| WO | 9615337 A1 | 5/1996 |
| WO | 9956117 A1 | 11/1999 |
| WO | 0156634 A1 | 8/2001 |
| WO | 02096335 A2 | 12/2002 |
| WO | 03034444 A1 | 4/2003 |
| WO | 2004004787 A2 | 1/2004 |
| WO | 2004059661 A1 | 7/2004 |
| WO | 2004080523 A2 | 9/2004 |
| WO | 2005002971 A1 | 1/2005 |
| WO | 2006007750 A1 | 1/2006 |
| WO | 2006026603 A2 | 3/2006 |
| WO | 2006074473 A2 | 7/2006 |
| WO | 2006129301 A2 | 12/2006 |
| WO | 2006135374 A2 | 12/2006 |
| WO | 2007016170 A1 | 2/2007 |
| WO | 2007016173 A1 | 2/2007 |
| WO | 2007030249 A2 | 3/2007 |
| WO | 2007041017 A1 | 4/2007 |
| WO | 2007071022 A1 | 6/2007 |
| WO | 2007082093 A2 | 7/2007 |
| WO | 2007096119 A2 | 8/2007 |
| WO | 2007104133 A1 | 9/2007 |
| WO | WO-2007104133 A1 * 9/2007 ........... G05B 13/024 | |
| WO | 2007149108 A2 | 12/2007 |
| WO | 2008028165 A2 | 3/2008 |
| WO | 2008037939 A2 | 4/2008 |
| WO | 2008066586 A2 | 6/2008 |
| WO | 2008082966 A2 | 7/2008 |
| WO | 2008140351 A1 | 11/2008 |
| WO | 2009152320 A2 | 12/2009 |
| WO | 2009152323 A2 | 12/2009 |
| WO | 2010020596 A1 | 2/2010 |
| WO | 2011126522 A2 | 10/2011 |
| WO | 2013082699 A1 | 6/2013 |
| WO | 2013085428 A1 | 6/2013 |
| WO | 2014036627 A1 | 3/2014 |
| WO | 2018057634 A1 | 3/2018 |
| WO | 2018057635 A1 | 3/2018 |
| WO | 2019191384 A1 | 10/2019 |
| WO | 2019191386 A1 | 10/2019 |

OTHER PUBLICATIONS

Declaration of Robert T. Stone, Ph.D., *Jubilant DraxImage Inc. v. Bracco Diagnostics Inc.*, IPR2018-01449, Exhibit 1015, Aug. 16, 2018, 175 pages.
Petition for Inter Partes Review of U.S. Pat. No. 9,299,467, *Jubilant DraxImage Inc. v. Bracco Diagnostics Inc.*, PR2018-01449, Aug. 22, 2018, 77 pages.
Patent Owner's Submission of Mandatory Notice Information Under 37 CFR 42.8(a)(2), *Jubilant DraxImage Inc. v. Bracco Diagnostics Inc.*, IPR2018-01449, Sep. 13, 2018, 4 pages.
Patent Owner's Preliminary Response, *Jubilant DraxImage Inc. v. Bracco Diagnostics Inc.*, IPR2018-01449, Nov. 29, 2018, 75 pages.
Petition for Inter Partes Review of U.S. Pat. No. 9,299,468, *Jubilant DraxImage Inc. v. Bracco Diagnostics Inc.*, PR2018-01450, Aug. 22, 2018, 56 pages.
Patent Owner's Submission of Mandatory Notice Information Under 37 CFR 42.8(a)(2), *Jubilant DraxImage Inc. v. Bracco Diagnostics Inc.*, IPR2018-01450, Sep. 13, 2018, 4 pages.
Patent Owner's Preliminary Response, *Jubilant DraxImage Inc. v. Bracco Diagnostics Inc.*, IPR2018-01450, Nov. 30, 2018, 64 pages.
Decision to Institute in IPR2018-01448, U.S. Pat. No. 9,299,468 B2, *Jubilant DraxImage Inc. v. Bracco Diagnostics Inc.*, Feb. 8, 2019, 22 pages.
Decision to Institute in IPR2018-01449, U.S. Pat. No. 9,299,467 B2, *Jubilant DraxImage Inc. v. Bracco Diagnostics Inc.*, Feb. 8, 2019, 21 pages.
Decision to Institute in IPR2018-01450, U.S. Pat. No. 9,299,468 B2, *Jubilant DraxImage Inc. v. Bracco Diagnostics Inc.*, Feb. 8, 2019, 19 pages.
ELFO Automatic Radiopharmaceutical Injection System for PET Imaging, Date Not Identified, 3 pages.
Commission Opinion, Inv. No. 337-TA-1110, Public Version, Dec. 11, 2019, 43 pages.
Bracco Diagnostics Inc.'s Petition for Review with Exhibits 1, 2 and 3, Inv. No. 337-TA-1110, Dec. 23, 2019, 240 pages.
Initial Determination on Violation of Section 337 and Recommended Determination on Remedy and Bond, Inv. No. 337-TA-1110, Public Version, Aug. 1, 2019, 185 pages.
337-1110_662084: Complainant Bracco Diagnostics Inc.'s Response to Jubilant's Motion for Summary Determination of Noninfringement of U.S. Pat. No. 9,750,869, U.S. Pat. No. 9,750,870, and U.S. Pat. No. 9,814,826 by Jubilant's Version 3.1 and Version 4 Designs and Memorandum in Support Thereof (Motion Response/Reply); 2-1386970: "Disputes to Chart of Material Facts", create date Nov. 19, 2018, www.edis.usitc.gov.
337-1110_662795: Staff's Response to Respondents' Motion for Summary Determination of Noninfringement of U.S. Pat. No. 9,750,869; U.S. Pat. No. 9,750,870; and U.S. Pat. No. 9,814,826 by Respondents' Version 3.1 and 4 Designs (Motion Response/ Reply); 1-1389338: "Staff's Response to Respondents' Motion for Summary Determination of Noninfringement of U.S. Pat. No. 9,750,869; U.S. Pat. No. 9,750,870; and U.S. Pat. No. 9,814,826 by Respondents' Version 3.1 and 4 Designs", create date Nov. 28, 2018, www.edis.usitc.gov.
337-1110_662796: Staff's Response to Complainant's Motion for Summary Determination of Infringement and Satisfaction of the Economic & Technical Prongs of the Domestic Industry Requirement (Motion Response/Reply); 1-1389340: "Staff's Response to Complainant's Motion for Summary Determination of Infringement & Satisfaction of the Economic & Technical Prongs of the Domestic Industry Requirement", create date Nov. 28, 2018, www.edis.usitc. gov.
Attachment D: Respondents' Obviousness Contentions, Exchanged in ITC Investigation No. 337-TA-1110, Aug. 8, 2018, 38 pages. (Confidential Business Information Redacted).
Exhibit D.1: U.S. Pat. No. 9,814,826 Claim Chart—Obviousness Over Klein, Exchanged in ITC Investigation No. 337-TA-1110, Aug. 8, 2018, 207 pages. (Confidential Business Information Redacted).
Exhibit D.2: U.S. Pat. No. 9,750,869 Claim Chart—Obviousness Over Klein, Exchanged in ITC Investigation No. 337-TA-1110, Aug. 8, 2018, 244 pages. (Confidential Business Information Redacted).
Exhibit D.3: U.S. Pat. No. 9,750,870 Claim Chart—Obviousness Over Klein, Exchanged in ITC Investigation No. 337-TA-1110, Aug. 8, 2018, 172 pages. (Confidential Business Information Redacted).
Exhibit D.4: U.S. Pat. No. 9,814,826 Claim Chart—Obviousness Over Cardiogen-82, Exchanged in ITC Investigation No. 337-TA-1110, Aug. 8, 2018, 224 pages. (Confidential Business Information Redacted).
Exhibit D.5: U.S. Pat. No. 9,750,869 Claim Chart—Obviousness Over Cardiogen-82, Exchanged in ITC Investigation No. 337-TA-1110, Aug. 8, 2018, 255 pages. (Confidential Business Information Redacted).
Exhibit D.6: U.S. Pat. No. 9,750,870 Claim Chart—Obviousness Over Cardiogen-82, Exchanged in ITC Investigation No. 337-TA-1110, Aug. 8, 2018, 199 pages. (Confidential Business Information Redacted).
Bracco Diagnostics Inc.'s Rebuttal Contentions in Response to Respondents' Aug. 8, 2018 Contentions (Including Responses to OUII Staff ROG Nos. 13, 18, 19, 20-22, 32 and Respondents' ROG Nos. 5, 9-11, 18, 33), Investigation No. 337-TA-1110, Aug. 15, 2018, 35 pages. (Confidential Business Information Redacted).
Supplemental Exhibit 1, Response to Supplemental Exhibit D.1: U.S. Pat. No. 9,814,826 Invalidity Contentions, Exchanged in ITC Investigation No. 337-TA-1110, Aug. 15, 2018, 22 pages. (Confidential Business Information Redacted).
Supplemental Exhibit 2, Response to Supplemental Exhibit D.2: U.S. Pat. No. 9,750,869 Invalidity Contentions, Exchanged in ITC Investigation No. 337-TA-1110, Aug. 15, 2018, 23 pages. (Confidential Business Information Redacted).

(56) References Cited

OTHER PUBLICATIONS

Supplemental Exhibit 3, Complainant's Supplemental Response to Respondents' Supplemental Exhibit D.3: U.S. Pat. No. 9,750,870 Invalidity Contentions, Exchanged in ITC Investigation No. 337-TA-1110, Aug. 15, 2018, 19 pages. (Confidential Business Information Redacted).
Bracco Diagnostics Inc.'s Supplemental Rebuttal Contentions in Response to Respondents' Aug. 8, 2018 Contentions Pursuant to Order No. 16, Investigation No. 337-TA-1110, Aug. 23, 2018, 18 pages. (Confidential Business Information Redacted).
Supplemental Exhibit 1, Response to Supplemental Exhibit D.1: U.S. Pat. No. 9,814,826 Invalidity Contentions, Exchanged in ITC Investigation No. 337-TA-1110, Aug. 23, 2018, 22 pages. (Confidential Business Information Redacted).
Supplemental Exhibit 2, Response to Supplemental Exhibit D.2: U.S. Pat. No. 9,750,869 Invalidity Contentions, Exchanged in ITC Investigation No. 337-TA-1110, Aug. 23, 2018, 25 pages. (Confidential Business Information Redacted).
Supplemental Exhibit 3, Complainant's Supplemental Response to Respondents' Supplemental Exhibit D.3: U.S. Pat. No. 9,750,870 Invalidity Contentions, Aug. 23, 2018, 26 pages. (Confidential Business Information Redacted).
Exhibit 4, Response to Exhibit D.4: U.S. Pat. No. 9,814,826 Invalidity Contentions, Aug. 23, 2018, 37 pages. (Confidential Business Information Redacted).
Exhibit 5, Response to Exhibit D.5: U.S. Pat. No. 9,814,826 Invalidity Contentions, Aug. 23, 2018, 39 pages. (Confidential Business Information Redacted).
Supplemental Exhibit 6, Complainant's Supplemental Response to Respondents' Supplemental Exhibit D.6: U.S. Pat. No. 9,750,870 Invalidity Contentions, Aug. 23, 2018, 44 pages. (Confidential Business Information Redacted).
337-1110_652068: Respondents' Jubilant DraxImage Inc., Jubilant Pharma Limited, and Jubilant Life Sciences Limited Notice of Prior Art (Notice of Prior Art); 1-1311880: "Respondents First Supplemental Notice of Prior Art", create date Aug. 3, 2018, www.edis.usitc.gov, 29 pages.
Respondents' Pre-Hearing Brief, Public Version, Investigation No. 337-TA-1110, Dec. 12, 2018, 550 pages.
Complainant Bracco Diagnostics Inc.'s Pre-Hearing Brief, Public Version, Inv. No. 337-TA-1110, Dec. 13, 2018, 568 pages.
Report of Robert T. Stone, Ph.D on Invalidity of U.S. Pat. No. 9,750,869, U.S. Pat. No. 9,750,870 and U.S. Pat. No. 9,814,826, Sep. 17, 2018, 1051 pages. (Confidential Business Information Redacted).
Corrected Expert Report of Norbert J. Pelc, Sc.D, Investigation No. 337-TA-1110, Oct. 1, 2018, 289 pages. (Confidential Business Information Redacted).
Declaration of Robert T. Stone, Ph.D., *Jubilant DraxImage Inc. v. Bracco Diagnostics Inc.*, IPR2018-01448 and PR2018-01450, Exhibit 1015, Aug. 17, 2018, 267 pages.
Curriculum Vitae of Robert T. Stone, Ph.D., *Jubilant DraxImage Inc. v. Bracco Diagnostics Inc.*, IPR2018-01448, Exhibit 1016, filed Aug. 22, 2018, 10 pages.
Declaration of Venkatesh L. Murthy, M.D., Ph.D., *Jubilant DraxImage Inc. v. Bracco Diagnostics Inc.*, IPR2018-01448, Exhibit 1017, Aug. 14, 2018, 52 pages.
US Pharmacopeia 23 National Formulary 18, 1995, 5 pages (cited as Exhibit 1019 in IPR2018-01448, *Jubilant DraxImage Inc. v. Bracco Diagnostics Inc.*).
Declaration of Andy Adler, Ph.D., *Jubilant DraxImage Inc. v. Bracco Diagnostics Inc.*, IPR2018-01448, Exhibit 1020, Aug. 17, 2018, 156 pages.
Bracco CardioGen-82 Infusion System User's Guide, Rev. 07, Jul. 20, 2004, 49 pages (cited as Exhibit 1021 in IPR2018-01448, *Jubilant DraxImage Inc. v. Bracco Diagnostics Inc.*).
Chatal et al., "Story of rubidium-82 and advantages for myocardial perfusion PET imaging," Frontiers in Medicine, v. 2, art. 65, Sep. 11, 2015, pp. 1-7 (cited as Exhibit 1026 in IPR2018-01448, *Jubilant DraxImage Inc. v. Bracco Diagnostics Inc.*).

ISO 13485:2003—Medical Devices—Quality Management Systems—Requirements for Regulatory Purposes, Jul. 15, 2003, 64 pages (cited as Exhibit 1028 in IPR2018-01448, *Jubilant DraxImage Inc. v. Bracco Diagnostics Inc.*).
21 CFR Part 820.1, US Food and Drug Administration, HHS, 2005, pp. 152-153 (cited as Exhibit 1029 in IPR2018-01448, *Jubilant DraxImage Inc. v. Bracco Diagnostics Inc.*).
EN 62274:2005—Medical Electrical Equipment—Safety of Radiotherapy Record and Verify Systems, Dec. 28, 2005, 22 pages (cited as Exhibit 1030 in IPR2018-01448, *Jubilant DraxImage Inc. v. Bracco Diagnostics Inc.*).
21 CFR Part 11.1, US Food and Drug Administration, HHS, 2004, pp. 109-110 (cited as Exhibit 1031 in IPR2018-01448, *Jubilant DraxImage Inc. v. Bracco Diagnostics Inc.*).
10 CFR Part 20.1001-1002, Nuclear Regulatory Commission, 2005, pp. 317-318 (cited as Exhibit 1032 in IPR2018-01448, *Jubilant DraxImage Inc. v. Bracco Diagnostics Inc.*).
10 CFR Part 20.1003, Nuclear Regulatory Commission, 2005, pp. 318-324 (cited as Exhibit 1033 in IPR2018-01448, *Jubilant DraxImage Inc. v. Bracco Diagnostics Inc.*).
Wang et al., Handbook of Radioactive Nuclides, The Chemical Rubber Co., 1969, 59 pages (cited as Exhibit 1034 in IPR2018-01448, *Jubilant DraxImage Inc. v. Bracco Diagnostics Inc.*).
Bates et al., "Effect of Computerized Physician Order Entry and a Team Intervention on Prevention of Serious Medication Errors," JAMA, vol. 280, No. 15, Oct. 21, 1998, pp. 1311-1316 (cited as Exhibit 1035 in IPR2018-01448, *Jubilant DraxImage Inc. v. Bracco Diagnostics Inc.*).
Bates et al., "The Impact of Computerized Physician Order Entry on Medication Error Prevention," Journal of the American Medical Informatics Association, vol. 6, No. 4, Jul./Aug. 1999, pp. 313-321 (cited as Exhibit 1036 in IPR2018-01448, *Jubilant DraxImage Inc. v. Bracco Diagnostics Inc.*).
Medical Devices Security Technical Implementation Guide, Defense Information Systems Agency, Version 1, Release 1, Jul. 27, 2010, 56 pages (cited as Exhibit 1037 in IPR2018-01448, *Jubilant DraxImage Inc. v. Bracco Diagnostics Inc.*).
Implementation Guide for the Use of Bar Code Technology in Healthcare, HIMSS, 2003, 72 pages (cited as Exhibit 1038 in IPR2018-01448, *Jubilant DraxImage Inc. v. Bracco Diagnostics Inc.*).
337-TA-1110: Complainant Bracco Diagnostics Inc.'s Responses to Respondents Jubilant DraxImage, Inc.'s, Jubilant Pharma Limited's, and Jubilant Life Sciences' Fourth Set of Interrogatories (No. 68), Aug. 6, 2018, 11 pages (cited as Exhibit 1039 in IPR2018-01448, *Jubilant DraxImage Inc. v. Bracco Diagnostics Inc.*).
Declaration of Carol Wadke, *Jubilant DraxImage Inc. v. Bracco Diagnostics Inc.*, IPR2018-01448, Exhibit 1042, Jul. 27, 2018, 174 pages.
Petition for Inter Partes Review of U.S. Pat. No. 9,299,468, *Jubilant DraxImage Inc. v. Bracco Diagnostics Inc.*, IPR2018-01448, Aug. 22, 2018, 97 pages.
Patent Owner's Submission of Mandatory Notice Information Under 37 CFR 42.8(a)(2), *Jubilant DraxImage Inc. v. Bracco Diagnostics Inc.*, IPR2018-01448, Sep. 13, 2018, 4 pages.
Patent Owner's Preliminary Response, *Jubilant DraxImage Inc. v. Bracco Diagnostics Inc.*, IPR2018-01448, Nov. 29, 2018, 79 pages.
Redline comparison between US Patent Publication No. 2004/0260143 A1 (Reilly et al.), published Dec. 23, 2004 and U.S. Pat. No. 6,767,319 B2 (Reilly et al.), issued Jul. 27, 2004, filed Nov. 29, 2018 as Exhibit 2002 in PR2018-01448, *Jubilant DraxImage Incv. Bracco Diagnostics Inc.*, 22 pages.
"Alaris GH Syringe Pump Directions For Use," Cardinal Health, Oct. 2005, 34 pages.
Alvarez-Diez et al. "Manufacture of strontium-82/rubidium-82 generators and quality control of rubidium-82 chloride for myocardial perfusion imaging in patients using positron emission tomography," Applied Radiation and Isotopes, 1999, pp. 1015-1023.
"Auto Syringe AS40A: Model AS40A Infusion Pump Operation Manual," Baxter, Aug. 1993, 84 pages.
"BodyGuard 323 Infusion Pump System Operator Manual," Caesarea Medical Electronics Ltd, Mar. 2009, 81 pages.

(56) References Cited

OTHER PUBLICATIONS

Brochure, "IV and Liquid Filters: Speedflow Adult 0.2 um Positive", http://www.gvs.it/flex/FixedPages/UK/LiquidFilters.php/L/UK/ID/Speedflow%20Adjust% . . . Retrieved from URL on Nov. 11, 2008.
BRACCO Brochure, "Rubidium 82 Infusion System, Easy to Operate . . . Automated . . . Complete", © Bracco Diagnostics, Inc., 0605-002NA, Jun. 2001, (2 pages).
"CardioGen-82 Infusion System User's Guide," Medical Product Service GmbH, Jul. 3, 2007, 53 pages.
"CardioGen-82 Rubidium Rb 82 Generator For Elution of Rubidium Chloride Rb 82 Injection," Bracco Diagnostics, May 2000, 13 pages.
Daraban et al., "Efficiency Calibration in Gamma Spectrometry by Using 232Th Series Radionuclides," Romanian Journal of Physics, vol. 58, Supplement, 2013, pp. S99-S107.
Neil J. Epstein, "A Rb82 infusion system for quantitative perfusion imaging with 3D PET" Applied Radiation and Isotopes, vol. 60, Feb. 9, 2004, pp. 921-927, XP002557544 DOI:10, 1016/j.apradiso. 2004.02.002.
International Patent Application No. PCT/US2017/052537, International Search Report and Written Opinion dated Jan. 9, 2018, 12 pages.
Imaging Technology News, web exclusive: "FDG-PET Injector Thrusts New Life into Molecular Imaging", Apr. 2008, 2 pages.
R. Klein, "Precise 82RB infusion system for cardiac perfusion measurement using 3D positron emission tomography", Ottawa-Carleton Institute for Electrical and Computer Engineering School of Information Technology and Engineering (Electrical & Computer Engineering), Feb. 2005, 147 pages.
R. Klein, "Precision control of eluted Activity from a Sr/Rb generator for cardiac positron emission tomography", Proceedings of the 26th Annual International Conference of the IEEE EMBS San Francisco, CA, USA, Sep. 1-5, 2004, 4 pages.
R. Klein, "Precision controlled elution of a Sr82/Rb82 generator for cardiac perfusion imaging with positron emission tomography" Physics in Medicine and Biology, vol. 52, Jan. 11, 2007, pp. 659-673, XP002557545 DOI:10, 1088/0031-9155/52/3/009.
Kost, "Preventing Medical Errors in Point-of-Care Testing," Archives of Pathology & Laboratory Medicine, vol. 125, No. 10, Oct. 2001, pp. 1307-1315.
Emer Pax, POSIJET® Integrated FDG dispensing and infusion system, www.lemerpax.com (copyright date May 2008).
Eveson, "Medical Devices: The Therac-25," Appendix of: Safeware: System Safety and Computers, 1995, 49 pages.
Lortie et al., "Quantification of myocardial blood flow with 82Rb dynamic PET imaging," Eur. J. Nucl. Med. Mol. Imaging, vol. 34, 2007, pp. 1765-1774.
Luca et al., "Calibration of the High and Low Resolution Gamma-Ray Spectrometers," Romanian Reports in Physics, vol. 64, No. 4, 2012, pp. 968-976.
Machine translation of abstract of RU2307378 published Sep. 27, 2007 (Oao Sojuztsvetmetavtomatika).
"Medfusion 3000 Series Technical Service Manual," Smiths Medical, 2010, 184 pages.
Neirincks et al., "Evaluation of Inorganic Adsorbents for the Rubidium-82 Generator: I. Hydrous SnO2," The Journal of Nuclear Medicine, vol. 23, No. 3, Jan. 1, 1982, pp. 245-249.
Rawool-Sullivan et al., "Use of Wavelet Denoising in Identifying Radioactive Isotopes Using a Gamma-Ray Spectrum," Summary #2826 American Nuclear Society, Winter 2010 conference, Nov. 1, 2010, 4 pages.
337-1110_640015: Public Version of Complaint and Exhibits 1-28 (Complaint); 1-1283977: "640015 Public Complaint: GreenbergTraurig's letter dated Mar. 27, 2018 re Complainant's filing of documents to support Bracco's request that the Commission commence 337 investigation", create date Apr. 13, 2018, www.edis.usitc.gov.

337-1110_643191: Notice of Institution of Investigation (Notice); 1-1285952: "1285952: Notice of Institution of Investigation Inv. No. 337-TA-1110", create date Apr. 25, 2018, www.edis.usitc.gov.
337-1110_647318: Joint List of Disputed and Undisputed Claim Terms (Other); 1-1298795: "1298795: Joint List of Disputed and Undisputed Claim Terms", create date Jun. 8, 2018, www.edis.usitc. gov.
337-1110_648102: Proposed Construction of Disputed Claim Terms (Response/Submission to ALJ Order); 1-1301950: "Proposed Constructions", create date Jun. 18, 2018, www.edis.usitc.gov.
337-1110_650007: Respondent Jubilant DraxImage Inc., Jubilant Pharma Limited, and Jubilant Life Sciences Limited's Notice of Prior Art (Notice of Prior Art); 1-1306444: "Notice of Prior Art", create date Jul. 10, 2018, www.edis.usitc.gov.
337-1110_652080: Joint Unopposed Motion for Leave to File Joint Submission of Identification of Claim Terms and Proposed Constructions Thereof out of Time (Motion); 2-1311910: "Identification of Claim Terms", create date Mar. 3, 2018, www.edis.usitc.gov. create date Aug. 3, 2018, www.edis.usitc.gov.
337-1110_652479: Granting Joint Motion to File Identification of Claim Terms and Constructions out of Time (Order); 1-1313857: "652479: Order No. 14", create date Aug. 8, 2018, www.edis.usitc. gov.
337-1110_661785: Complainant Bracco Diagnostics Inc.'s Motion for Summary Determination of Infringement and Satisfaction of the Economic and Technical Prongs of the Domestic Industry Requirement (Motion); 1-1385894: "Letter to Barton", create date Nov. 14, 2018, www.edis.usitc.gov.
337-1110_661785: Complainant Bracco Diagnostics Inc.'s Motion for Summary Determination of Infringement and Satisfaction of the Economic and Technical Prongs of the Domestic Industry Requirement (Motion); 2-1385895: "Motion for Summary Determination", create date Nov. 14, 2018, www.edis.usitc.gov.
337-1110_661785: Complainant Bracco Diagnostics Inc.'s Motion for Summary Determination of Infringement and Satisfaction of the Economic and Technical Prongs of the Domestic Industry Requirement (Motion); 3-1385896: "Chart of Undisputed Material Facts", create date Nov. 14, 2018, www.edis.usitc.gov.
337-1110_661851: Errata to Staff's Response to Complainant's Motion for Summary Determination of Infringement and Satisfaction of the Economic and Technical Prongs of the Domestic Industry Requirement (Motion Response/Reply); 1-1385993:, create date Nov. 14, 2018, www.edis.usitc.gov.
337-1110_660985: Respondents' Motion for Summary Determination of Noninfringement of U.S. Pat. Nos. 9,750,869, U.S. Pat. Nos. 9,750,870, and U.S. Pat. Nos. 9,814,826 by Respondents' Version 3.1 and Version 4 Designs (Motion); 1-1383714: "Respondents' Motion for Summary Determination (PV)", create date Nov. 5, 2018, www.edis.usitc.gov.
337-1110_660985: Respondents' Motion for Summary Determination of Noninfringement of U.S. Pat. No. 9,750,869, U.S. Pat. No. 9,750,870, and U.S. Pat. No. 9,814,826 by Respondents' Version 3.1 and Version 4 Designs (Motion); 2-1383715: "Memorandum in Support of Respondents' Motion for Summary Determination (PV)", create date Nov. 5, 2018, www.edis.usitc.gov.
337-1110_660985: Respondents' Motion for Summary Determination of Noninfringement of U.S. Pat. No. 9,750,869, U.S. Pat. No. 9,750,870, and U.S. Pat. No. 9,814,826 by Respondents' Version 3.1 and Version 4 Designs (Motion); 17-1383730: "Chart of Material Facts in Support of Respondents' MSD", create date Nov. 5, 2018, www.edis.usitc.gov.
337-1110_661010: Complainant Bracco Diagnostics Inc.'s Motion for Summary Determination of Infringement and Satisfaction of the Economic and Technical Prongs of the Domestic Industry Requirement (Motion); 1-1383879: "Bracco's Motion for Summary Determination", create date Nov. 5, 2018, www.edis.usitc.gov.
337-1110_661010: Complainant Bracco Diagnostics Inc.'s Motion for Summary Determination of Infringement and Satisfaction of the Economic and Technical Prongs of the Domestic Industry Requirement (Motion); 2-1383880: "Bracco's Chart of Undisputed Material Facts", create date Nov. 5, 2018, www.edis.usitc.gov.
337-1110_661038: Respondents' Unopposed Motion to Replace Respondents' Chart of Material Facts in Support of Motion for

(56) References Cited

OTHER PUBLICATIONS

Summary Determination (Motion); 1-1383923: "Respondents' Unopposed Motion to Replace Respondents' Chart of Material Facts in Support of Motion for Summary Determination (Public Version)", create date Nov. 5, 2018, www.edis.usitc.gov.

337-1110_662007: Respondents' Memorandum in Opposition of Complainant's Motion for Summary Determination of Infringement and Satisfaction of the Economic and Technical Prongs of the Domestic Industry Requirement (Motion Response/Reply); 1-1386474: "Respondents' Memorandum in Opposition to Complainant's Motion for Summary Determination (PV)", create date Nov. 16, 2018, www.edis.usitc.gov.

Ruby Rubidium Elution System User Manual, Jubilant DraxImage, Version 7, Created Jun. 3, 2014, Modified Jan. 9, 2015, 58 pages.

Intego PET Infusion System Operation Manual, Medrad, Rev. G, Jun. 2013, 142 pages.

Commission Investigative Staff's Prehearing Brief, Inv. No. 337-TA-1110, Dec. 20, 2018, 129 pages. (Confidential Business Information Redacted).

Saha et al., "Use of the 82Sr/82Rb Generator in Clinical PET Studies," International Journal of Radiation Applications and Instrumentation, Part B. Nuclear Medicine and Biology, vol. 17, No. 8, 1990, pp. 763-768.

Yano et al., "Evaluation and Application of Alumina-Based Rb-82 Generators Charged with High Levels of Sr-82/85," The Journal of Nuclear Medicine, vol. 20, No. 9, 1979, pp. 961-966.

Yano et al., "A Precision Flow-Controlled Rb-82 Generator for Bolus or Constant-Infusion Studies of the Heart and Brain," The Journal of Nuclear Medicine, Preliminary Notes, vol. 22, No. 11, 1981, pp. 1006-1010.

Yano, "Essentials of a Rubidium-82 Generator for Nuclear Medicine," International Journal of Radiation Applications and Instrumentation, Part A. Applied Radiation and Isotopes, vol. 38, No. 3, 1987, pp. 205-211.

337-1110_662084: Complainant Bracco Diagnostics Inc.'s Response to Jubilant's Motion for Summary Determination of Noninfringement of U.S. Pat. No. 9,750,869, U.S. Pat. No. 9,750,870, and U.S. Pat. No. 9,814,826 by Jubilant's Version 3.1 and Version 4 Designs and Memorandum in Support Thereof (Motion Response/Reply); 1-1386969: "Complainant's Response to Motion for Summary Determination", create date Nov. 19, 2018, www.edis.usitc.gov.

Final Written Decision in IPR2018-01448, U.S. Pat. No. 9,299,468 B2, *Jubilant DraxImage Inc.* v. *Bracco Diagnostics Inc.*, dated Feb. 6, 2020, 98 pages.

Final Written Decision in IPR2018-01449, U.S. Pat. No. 9,299,467 B2, *Jubilant DraxImage Inc.* v. *Bracco Diagnostics Inc.*, dated Feb. 6, 2020, 58 pages.

Final Written Decision in IPR2018-01450, U.S. Pat. No. 9,299,468 B2, *Jubilant DraxImage Inc.* v. *Bracco Diagnostics Inc.*, dated Feb. 6, 2020, 51 pages.

\* cited by examiner

SYSTEMS AND TECHNIQUES FOR GENERATING, INFUSING, AND CONTROLLING RADIOISOTOPE DELIVERY

CROSS-REFERENCE

This application is a 35 U.S.C. 371 national phase filing from International Application No. PCT/US2017/052537, filed Sep. 20, 2017, which claims the benefit of U.S. Provisional Patent Application No. 62/397,022, U.S. Provisional Patent Application No. 62/397,025, and U.S. Provisional Patent Application No. 62/397,026, each of which was filed on Sep. 20, 2016. The entire contents of these applications are incorporated herein by reference.

TECHNICAL FIELD

This disclosure relates to radiopharmaceuticals used in nuclear medicine and, more particularly, to systems and techniques for generating and delivering radiopharmaceuticals.

BACKGROUND

Nuclear medicine employs radioactive material for therapy and diagnostic imaging. Positron emission tomography (PET) is one type of diagnostic imaging, which utilizes doses of radiopharmaceutical. The doses of radiopharmaceutical may be injected or infused into a patient prior to or during a PET scan procedure. An infused dose of radiopharmaceutical can be absorbed by cells of a target organ of the patient and emit radiation. A PET scanner can detect the emitted radiation in order to generate an image of an organ. For example, to image body tissue such as the myocardium, a patient may be injected or infused with rubidium-82 ($^{82}$Rb). Rubidium-82 may exhibit similar physiological uptake as potassium and, accordingly, may be taken into the myocardium following potassium pathways.

Rubidium-82 can be generated for nuclear medicine procedures using a strontium-rubidium generator ($^{82}$Sr/$^{82}$Rb generator). Rubidium-82 is a radioactive decay product of strontium-82. Typically, strontium-rubidium generators contain strontium bound to a generator column through which an eluant is flushed during operation. As strontium-82 decays to rubidium-82, the rubidium-82 may release from the generator column and enter the eluant. The resulting stream, which is called an eluate, can be injected or infused into a patient.

SUMMARY

In general, the disclosure is directed to devices, systems, components, and techniques for generating and/or delivering radioactive liquids. The radioactive liquid may be generated and infused into a patient during a diagnostic imaging procedure, such as a positron emission tomography (PET)/computed tomography (CT) or a positron emission tomography (PET)/magnetic resonance imaging (MRI) procedure. Before, during, and/or after a specific diagnostic imaging procedure, the radiation level of radioactive liquid generated by an infusion system may be measured to determine the activity level (e.g., magnitude of radiation emissions) of one or more radioisotope in the radioactive liquid. The activity level of one or more radioisotopes may be measured to determine that a radioisotope targeted for infusion into a patient during an imaging procedure is at an appropriate level for the specific procedure being undertaken. Additionally or alternatively, the activity level of one or more radioisotopes may be measured to determine if a radioisotope having a longer half-life than the radioisotope targeted for infusion is present above a threshold concentration in the radioactive liquid. Such comparatively long-lasting radioisotopes may be contaminants that are desirably excluded from infusion into a patient.

For example, in the application of a strontium-rubidium radioisotope generator, a radioactive eluate containing the radioisotope rubidium-82 (also referred to as $^{82}$Rb and Rb-82) can be generated by passing an eluant across a substrate containing bound strontium-82 (also referred to as $^{82}$Sr and Sr-82). As Sr-82 decays into Rb-82, the Rb-82 may release from the substrate, causing the Rb-82 to release into the eluant and thereby generating a radioactive eluate via elution. As the radioisotope generator approaches the end of its service life, strontium may itself begin releasing into the eluate produced by the generator in addition to its decay product Rb-82. The activity level of strontium in the eluate may be monitored to help ensure that eluate containing too much strontium (or other contaminating radioisotope) is not injected into the patient. This is because Sr-82 has a much longer half-life (25.5 days) than the half-life of Rb-82 (76 seconds) and, if injected into the patient, will produce radioactive emissions inside of patient for a longer period of time than Rb-82.

In some examples according to the present disclosure, an infusion system is described that includes multiple detectors positioned to evaluate the safety of radioactive eluate generated by a radioisotope generator. The multiple detectors may each be used to determine the activity of the same or different radioisotopes in the radioactive eluate. Each detector can detect radioactive emissions emitted from the radioactive eluate, and the activity level, or concentration, of one or more radioisotopes that may be present in the radioactive eluate can be determined therefrom. In some configurations, the multiple detectors are implemented using a beta detector and a gamma detector.

A beta detector can measure beta emissions caused by radioactive beta decay. During beta decay, a beta particle that is either an electron or a positron is emitted from an atomic nucleus. The beta detector can detect beta particles emitted from the radioactive eluate, allowing the activity level of a radioisotope assumed to be associated with those beta particles to be determined. By contrast, the gamma detector can measure gamma emissions or photons caused by radioactive gamma decay. During gamma decay, a stream of high-energy photons may be emitted from an atomic nucleus, providing detectable gamma rays. The energy level of the gamma rays may vary depending on the specific radioisotope from which the rays are emitted. The gamma detector can detect the gamma emissions, for example by measuring a full or partial gamma spectrum, allowing the activity level of one or more radioisotopes to be determined. A gamma detector can discriminate photons with different energy levels, unlike a dose calibrator.

Activity measurements made by a beta detector and a gamma detector are distinguishable from activity measurements made by a dose calibrator. A dose calibrator is an instrument used to assay the activity of a radioactive material prior to clinical use. The objective of the assay is to assure that the patient receives the prescribed dose for the diagnostic or therapeutic purpose. A dose calibrator includes an electrometer designed to measure a wide range of ionization current, spanning from femtoamperes (fA) for beta emitters up to tens of picoamperes (pA) for high-energy, high-yield photon emitters. Some high-activity assays can even involve microamperes (pA) currents. The accuracy of the electrometer depends upon the type and quality of the electrometer and the accuracy of the standard reference sources used to calibrate the electrometer. Dose calibrators have no intrinsic photon energy discrimination capability. A dose calibrator does not include a spectrometer and does not restrict the measurement to specific photon energies to the exclusion of others, which a gamma detector is capable of performing.

While the configuration of the radioisotope generator system can vary as described herein, in some examples, the system includes a beta detector positioned to measure the radioactivity of eluate flowing through tubing positioned adjacent the beta detector. The gamma detector may also be positioned to measure the radioactivity of eluate flowing through tubing or may instead be positioned to measure the radioactivity of a static (non-flowing) portion of radioactive eluate positioned adjacent the gamma detector. For example, the radioisotope generator system may include an eluate-receiving container in fluid communication with and downstream of infusion tubing in fluid communication with the outlet of a radioisotope generator. Radioactive eluate generated by the radioisotope generator can flow through the tubing and past the beta detector before discharging into the eluate-receiving container positioned adjacent the gamma detector.

The radioisotope generator system may operate in different modes in which measurements from the beta detector and/or the gamma detector are made. For example, during a quality control procedure, an infusion tubing line in fluid communication with the outlet of the radioisotope generator may be attached to the eluate-receiving container instead of a patient catheter. During this quality control procedure, the radioisotope generator may produce radioactive eluate that flows through the tubing line, past the beta detector, and into the eluate-receiving container. The beta detector may measure beta emissions from the radioactive eluate as it flows through the infusion tubing, e.g., to determine an activity level of Rb-82 in the eluate. The gamma detector may receive gamma emissions from eluate in the eluate-receiving container, e.g., to determine an activity level of Sr-82, strontium-85 (also referred to as $^{85}$Sr or Sr-85), and/or other contaminants in the eluate.

In practice, the activity level of Rb-82 in the eluate flowing through the infusion tubing line may be an order of magnitude or more greater than the activity level of any contaminants in the eluate. Accordingly, all beta emissions measured by the beta detector (including those emitted from Rb-82 and any potential contaminants, such as strontium) may be assumed to be emitted from Rb-82 present in the eluate without resolving those emissions emitted from any contaminating isotopes. To determine the activity of any such contaminating isotopes, the gamma emissions from a static portion of eluate in the eluate-receiving container can be measured. In some applications, the eluate is held in the eluate-receiving container for a period of time sufficient to allow Rb-82 in the eluate to substantially decay. This can reduce the amount of interfering gamma radiation (from Rb-82) measured by the gamma detector and allow the gamma detector to better detect gamma radiation emitted from contaminating radioisotopes (e.g., strontium). The activity level of one or more such contaminating radioisotopes can be determined based on the measured gamma emissions. If the activity of one or more such contaminating radioisotopes exceeds an allowable limit, the radioisotope generator system can prohibit a subsequent patient infusion procedure.

In addition to operating in a quality control mode, the radioisotope can also operate in a patient infusion mode to perform a patient infusion procedure. During the patient infusion procedure, the infusion tubing line in fluid communication with the outlet of the radioisotope generator may be attached to a patient catheter. Radioactive eluate generated by the radioisotope generator can flow through the tubing and past the beta detector. The radioisotope generator system may determine, based on the level of beta emissions measured by the beta detector, the activity of Rb-82 in the eluate produced by the radioisotope generator. The radioisotope generator system may divert eluate initially produced by the generator to a waste container until a threshold amount of Rb-82 activity is detected in the eluate. Upon detecting a threshold amount of Rb-82 activity via the beta detector, the generator system may divert the eluate from the waste container to the patient catheter, thereby injecting or infusing the patient with the eluate containing the radioactive Rb-82.

By configuring the radioisotope generator system with both a beta detector and a gamma detector, the radioisotope generator system can provide an integrated system to help ensure the safety and accuracy of radioactive eluate generated by the system. The combination of detectors can be used to perform a variety of different radioisotope measurements and to implement corresponding control schemes and/or quality analyses based on those radioisotope measurements. Accordingly, configuring the system with multiple detectors (e.g., measuring different types of radioactive emissions) may provide more accurate resolution between different radioisotopes and/or allow activities determined using multiple detectors to be cross-checked for increased accuracy.

In some examples, a radioisotope generator system according to the disclosure is configured as a mobile cart carrying a beta detector, a gamma detector, a radioisotope generator, a controller, and associated hardware and software to execute the techniques describes herein. The radioisotope generator system may also include a shielding assembly that provides a barrier to radioactive radiation. The shielding assembly can be mounted on the mobile cart and one or more of the other components carried on the cart can be mounted in the shielding assembly.

In some configurations, the shielding assembly includes a plurality of compartments separated by one or more walls of shielding material. For example, the shielding assembly may include one compartment containing the radioisotope generator and another compartment containing the gamma detector. The compartments of the shielding assembly can be arranged to position the compartment containing the gamma detector relative to the compartment containing the radioisotope generator so as to reduce background radiation emitted by the radioisotope generator from being detected by the gamma detector. If the gamma detector is exposed to too much background radiation (e.g., radiation emitted by the contents of the generator column), the gamma detector may be saturated and/or unable to suitably detect the level of radiation emitted by an eluate sample positioned in front of the detector when evaluating the safety of the eluate. Accordingly, ensuring that the gamma detector is appropriately shielding from the radioisotope generator may help ensure the safe and efficacious operation of the entire radioisotope generator system.

In one example, an infusion system is described that includes a frame that carries a beta detector and a gamma detector and is further configured to receive a radioisotope generator that generates radioactive eluate via elution. The beta detector is positioned to measure beta emissions emitted from the radioactive eluate. The gamma detector is positioned to measure gamma emissions emitted from a portion of the radioactive eluate to evaluate the safety of the radioactive eluate delivered by the infusion system, e.g., in addition to performing other functions such as dose constancy (which may also be referred to as a constancy evaluation or constancy check).

In another example, an infusion system is described that includes a beta detector, a gamma detector, a radioisotope generator, a waste container, an eluate-receiving container, and an infusion tubing line. The beta detector is positioned to measure beta emissions emitted from radioactive liquid supplied by the radioisotope generator and flowing through the infusion tubing line. The gamma detector is positioned to measure gamma emissions emitted from a static volume of radioactive liquid received by the eluate-receiving container.

In another example, an infusion system is described that includes a movable frame, an eluant reservoir, a pump, and a radioisotope generator coupled to the eluant reservoir through the pump. The radioisotope generator is configured to generate radioactive eluate containing Rb-82 via elution of a column containing Sr-82. The example specifies that the infusion system also includes a waste container, an eluate-receiving container, and an infusion tubing circuit. The infusion tubing circuit includes an infusion tubing line, an eluate line, and a waste line. The eluate line is connected to an outlet of the radioisotope generator, the patent line is positioned to provide fluid communication between the eluate line and the eluate-receiving container, and the waste line is positioned to provide fluid communication between the eluate line and the waste container. The example also includes a beta detector and a gamma detector. The beta detector is positioned to measure beta emissions emitted from radioactive eluate generated by the radioisotope generator and flowing through the eluate line. The gamma detector is positioned to measure gamma emissions emitted from radioactive eluate generated by the radioisotope generator and received by the eluate-receiving container.

In another example, an infusion system is described that includes a movable frame, an eluant reservoir, a pump, and a radioisotope generator coupled to the eluant reservoir through the pump. The radioisotope generator is configured to generate radioactive eluate containing Rb-82 via elution of a column containing Sr-82. The example specifies that the system also includes a waste container, an eluate-receiving container, and an infusion tubing circuit. The infusion tubing circuit includes an infusion tubing line, an eluate line, and a waste line. The eluate line is connected to an outlet of the radioisotope generator, the patent line is positioned to provide fluid communication between the eluate line and the eluate-receiving container, and the waste line is positioned to provide fluid communication between the eluate line and the waste container. The example system also includes radioactive shielding, a beta detector, and a gamma detector. The radioactive shield encloses at least a portion of the infusion tubing circuit, the beta detector, and the gamma detector. The beta detector is positioned to measure beta emissions emitted from radioactive eluate generated by the radioisotope generator and flowing through the eluate line. The gamma detector is positioned to measure gamma emissions emitted from radioactive eluate generated by the radioisotope generator and received by the eluate-receiving container. The system also includes a controller in electronic communication with the beta detector and the gamma detector. The controller is configured to determine an activity of Rb-82 in the radioactive eluate based on beta emissions measured by the beta detector and determine an activity of Sr-82 and/or Sr-85 in the radioactive eluate based on gamma emissions measured by the gamma detector (e.g., by measuring gamma emissions from the decay product of Sr-82, Rb-82). The controller is further configured to control the infusion system to deliver a dose of the radioactive eluate to a patient during a patient infusion procedure.

In another example, a system is described that includes a shielding assembly that has a plurality of compartments each providing a barrier to radioactive radiation. The system includes a first compartment configured to receive a radioisotope generator that generates a radioactive eluate via elution, a second compartment configured to receive a beta detector, and a third compartment configured to receive a gamma detector.

In another example, a system is described that includes a shielding assembly that includes a plurality of compartments each providing a barrier to radioactive radiation. The system includes a first compartment configured to receive and hold a radioisotope generator that generates a radioactive eluate via elution and a second compartment configured to receive a beta detector and at least a portion of an infusion tubing circuit that is in fluid communication with the radioisotope generator. The example specifies that the beta detector is positioned to measure beta emissions emitted from radioactive eluate generated by the radioisotope generator and flowing through the portion of the infusion tubing circuit. The system also includes a third compartment configured to receive an eluate-receiving container and a gamma detector. The gamma detector is positioned to measure gamma emissions emitted from a static portion of the radioactive eluate received by the eluate-receiving container. In addition, the example states that the system includes a fourth compartment configured to receive a waste container.

In another example, an infusion system is described that includes a frame that carries a beta detector, a gamma detector, and a controller communicatively coupled to the beta detector and the gamma detector. The frame is further configured to receive a strontium-rubidium radioisotope generator that generates a radioactive eluate via elution. The example specifies that the beta detector is positioned to measure beta emissions emitted from the radioactive eluate and the gamma detector is positioned to measure gamma emissions emitted from the radioactive eluate. The example also specifies that the controller is configured to determine an activity of rubidium in the radioactive eluate based on the beta emissions measured by the beta detector and determine an activity of strontium in the radioactive eluate based on the gamma emissions measured by the gamma detector.

In another example, a method is described that includes pumping an eluant through a strontium-rubidium radioisotope generator and thereby generating a radioactive eluate via elution. The method involves conveying the radioactive eluate across a beta detector and measuring beta emissions emitted from the radioactive eluate generated by the radioisotope generator and flowing through an eluate line and determining therefrom an activity of the radioactive eluate. The method also involves receiving the radioactive eluate conveyed across the beta detector in an eluate-receiving container positioned adjacent a gamma detector. In addition, the method includes measuring gamma emissions emitted from the radioactive eluate received by the eluate-receiving container and determining therefrom an activity of strontium in the radioactive eluate in the eluate-receiving container.

The details of one or more examples are set forth in the accompanying drawings and the description below. Other features, objects, and advantages will be apparent from the description and drawings, and from the claims.

DETAILED DESCRIPTION

Figure 1:
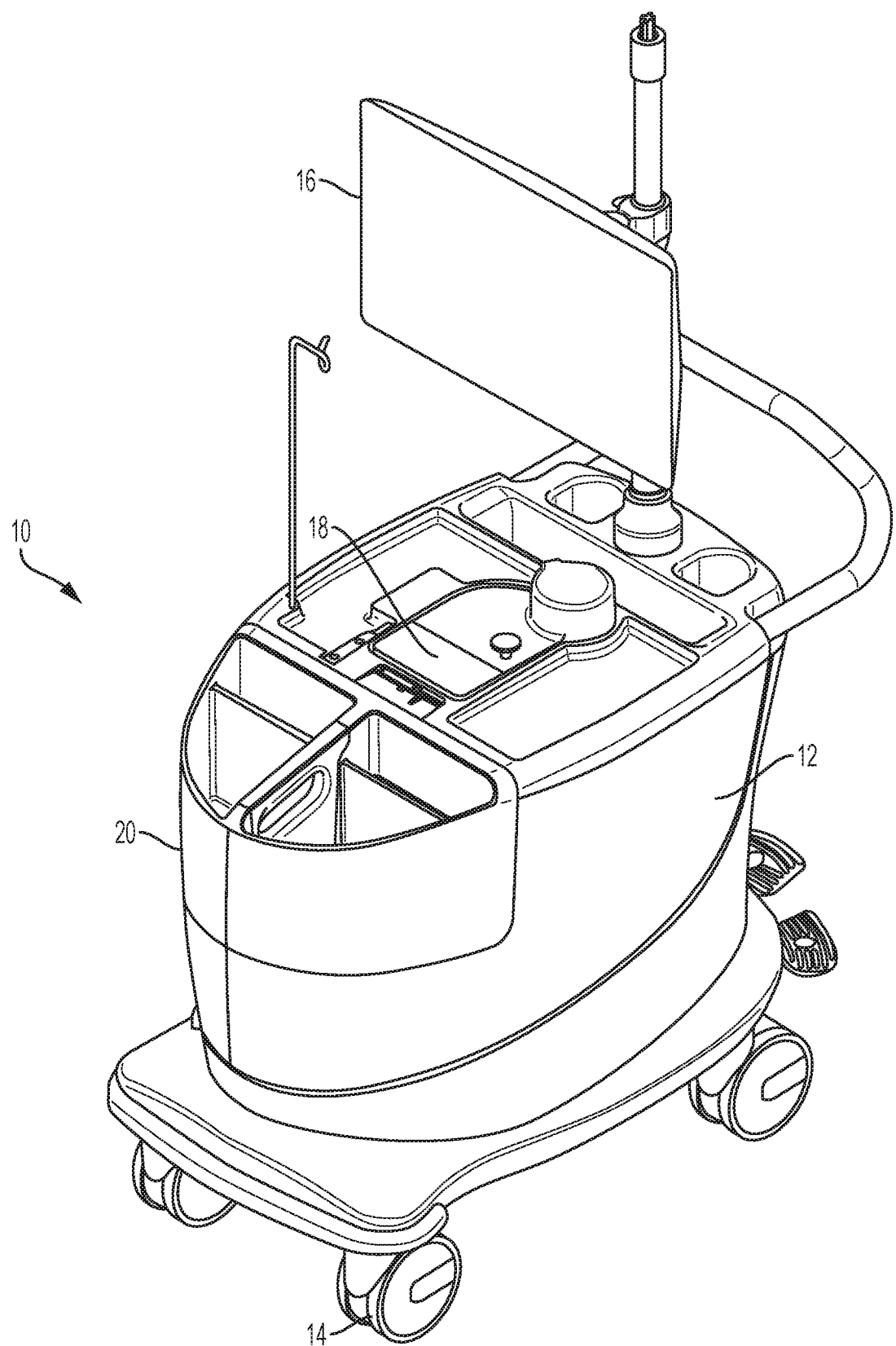
FIGS. 1 and 2 are perspective and top views, respectively, of an example infusion system that can be used to generate and infuse radioactive liquid.

In general, the disclosure relates to systems, components, and techniques for generating radioactive liquids, infusing radioactive liquids into patients, and ensuring the safety, accuracy, and quality of the radioactive liquids so generated. The described systems, components, and techniques can be implemented to detect and quantify multiple different radioisotopes. In some examples, a system includes multiple detectors positioned at different locations along the fluid pathway from a radioisotope source to measure one or more radioisotopes present in the fluid provided by the radioisotope source. The radioactive emissions detected and measured by the multiple detectors, alone or in combination, can be used to determine the activity of one or more radioisotopes present in the system. If the system determines that the activity of one or more radioisotopes is within allowable limits, the system may permit and control delivery of radioactive liquid from the radioisotope source to a patient. By contrast, if the system determines that the activity of one or more radioisotopes is outside of an allowable limit, for example during a quality control procedure, the system may prevent infusion into a patient during a subsequent patient infusion procedure until the issue is resolved.

In some examples described herein, a radioisotope generator system includes a beta detector and a gamma detector positioned downstream of the radioisotope generator that generates radioactive eluate via elution. During a patient infusion procedure, an infusion tubing circuit can connect an outlet of the radioisotope generator to a patient catheter. The infusion tubing circuit can be positioned adjacent the beta detector such that, as eluate flows through the infusion tubing circuit, the eluate passes over the beta detector. Beta emissions emitted by the eluate can be detected by the beta detector and the activity of a radioisotope associated with those beta emissions determined.

To execute a quality control procedure, the infusion tubing circuit can be connected to an eluate-receiving container instead of a patient catheter. The eluate-receiving container may be a vessel positioned adjacent to the gamma detector such that gamma emissions emitted by eluate received in the container can be detected by the gamma detector. During operation, an amount of eluate sufficient to partially or fully fill the eluate-receiving container can be generated and supplied to the eluate-receiving container. The gamma detector can then measure gamma emissions emitted by the eluate in the receiving container, e.g., to determine the activity of one or more radioisotopes present in the eluate. In some applications, beta emissions measured by the beta detector are used to determine the activity of Rb-82 in the eluate while gamma emissions measured by the gamma detector are used to determine the activity of contaminants such as strontium in the eluate.

A multi-detector system that facilitates measurement of different types of radioactive decay products from the same radioactive liquid sample may be integrated with the radioisotope generator that produces the radioactive liquid so measured. This can provide an integrated system for convenient use in, and deployment to, different clinical locations. For example, an integrated system, which may or may not be mobile, can include a frame that carries a beta detector and a gamma detector and is further configured to receive a radioisotope generator that generates radioactive eluate via elution. The beta detector can be supported on the frame either directly or indirectly, e.g., via radioactive shielding material. Similarly, the gamma detector can be supported on the frame either directly or indirectly, e.g., also via radioactive shielding material. The beta detector and the gamma detector can be positioned to measure beta and gamma emissions, respectively, from radioactive eluate discharged from the radioisotope generator. For example, the gamma detector can be positioned to measure gamma emissions from a portion of the radioactive eluate that allows for the safety of the radioactive eluate delivered by the overall infusion system to be evaluated. An infusion system can have a variety of features, functionalities, and components as described herein.

Figure 2:
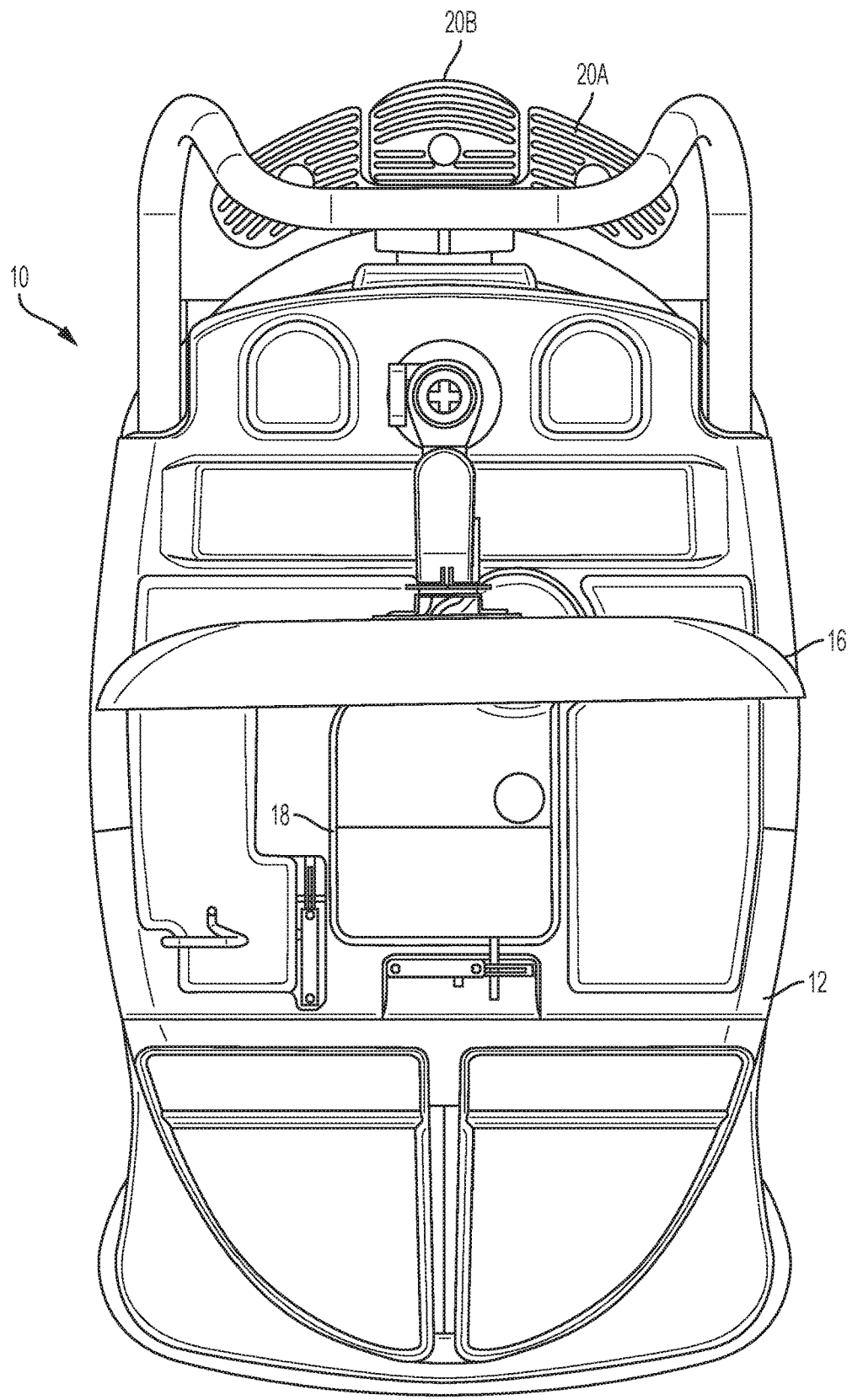

FIGS. 1 and 2 are perspective and top views, respectively, of an example infusion system 10 that can be used to generate and infuse radiopharmaceutical liquid. In the illustrated example, system 10 includes a cabinet structure 12 mounted on wheels 14 so as to be movable. System 10 also includes a user interface 16 that can be electronically and/or communicatively coupled to a controller that controls the operation of the infusion system. As described in greater detail below, cabinet structure 12 may house a radioisotope generator and multiple detectors configured to detect radioactive decay products, such as beta emissions and gamma emissions. In operation, the radioisotope generator may generate radioactive eluate via elution with an eluant. The eluate may be delivered proximate a beta detector to measure beta emissions emanating from the eluate and/or proximate a gamma detector to measure gamma emissions emanating from the eluate. A controller associated with system 10 may control operation of the system based on the measured beta emissions and/or measured gamma emissions.

Cabinet structure 12 may be a shell or a housing that defines an interior space configured to contain various components of system 10. For example, cabinet structure 12 may be configured (e.g., sized and/or shaped) to contain a shielding assembly in which radioactive materials of system 10 are contained, a pump to pump liquid through a radioisotope generator in the cabinet structure, a controller that controls operation of system 10, and/or other components of the system. Cabinet structure 12 may be fabricated from durable polymeric materials, light weight metals, or other suitable materials. In some examples, cabinet structure is fabricated from a radiation-resistant or impregnated polymeric material to prevent degradation of the cabinet structure in the event that radioactive liquid is inadvertently spilled on the cabinet structure.

Cabinet structure 12 may include one or more openings, doors, and/or removable portions to access an interior of the cabinet structure and components contained therein. In the illustrated example, cabinet structure 12 includes an opening 18 formed in the upper surface of the structure through which a portion of a shielding assembly extends and is accessible. As will be discussed in greater detail below, the portion of the shielding assembly extending through opening 18 may include a door to access a compartment that receives a portion of an infusion tubing circuit and/or a door to access a compartment into which an eluate-receiving container is inserted. As further illustrated, cabinet structure 12 may include a removable portion 20 that can be removed from a remainder of the cabinet structure to access an interior of the structure. In some examples, removable portion 20 provides access to a door of a shielding assembly compartment containing a radioisotope generator.

In the example of FIGS. 1 and 2, cabinet structure 12 is mounted on wheels 14. Wheels 14 may be useful to allow system 10 to be easily moved from one location to another location, e.g., to perform patient infusion procedures in different locations or to perform maintenances or repair tasks. To prevent system 10 from inadvertently moving after being positioned in a desired location, the system may include a brake system that prevents the system from being moved when engaged. As shown in FIG. 2, system 10 includes a brake system the includes at least one peddle mounted at the rear end of the cabinet structure, which is illustrated as including a first peddle 20A to engage the brake system and a second peddle 20B to disengage the brake system. The peddles 20A and 20B can be operatively connected to a mechanical interlock, friction pad, or other structure that, once engaged, inhibits movement of system 10. Pushing first peddle 20A downwardly with respect to gravity can engage the brake system while pushing second peddle 20B downwardly with respect to gravity can disengage the brake system. In other configurations, system 10 may only have a single break peddle that is pressed to both engage and disengage the break system, a hand control to engage and disengage the break system, or yet other engagement feature. When configured with multiple brake pedals as shown in FIG. 2, the pedals can be color indexed to indicate engagement (e.g., red for stop) and disengagement (e.g., green for go).

As mentioned above, system 10 also includes user interface 16. User interface 16 may include a display screen as illustrated or other output media, and user input media. For example, user interface may include a keyboard, mouse, depressible buttons, switches, and/or touch screen interface. In some examples, user interface 16 may be configured to provide visual, audible, and/or tactile feedback to a user. User interface 16 may be communicatively coupled (e.g., via a wired or wireless connection) to a controller that controls the operation of system 10. A clinician or other user may interact with system 10 through user interface 16, e.g., to change or establish the parameters of a patient infusion procedure, change or establish the parameters of a quality control procedure, view historical or maintenance information, or otherwise interact with system 10. In one example, user interface 16 is implemented as a touchscreen having a screen that a user can physically touch to communicate with system 10.

In the illustrated example, user interface 16 is shown as a display or touch screen mounted on a pole extending vertically from cabinet structure 12. When so configured, user interface 16 may be rotatably coupled to the mounting pole so as to be swiveled to any rotational position desired by a user and/or translated to different vertical positions. While user interface 16 is illustrated as being physically attached to cabinet structure 12, in other applications, user interface 16 may be physically separated from the cabinet structure. For example, user interface 16 may be provided through a mobile communication device (e.g., smart phone, tablet computer) or otherwise physically separate from cabinet structure 12 and communicatively coupled to components contained therein.

Figure 3:
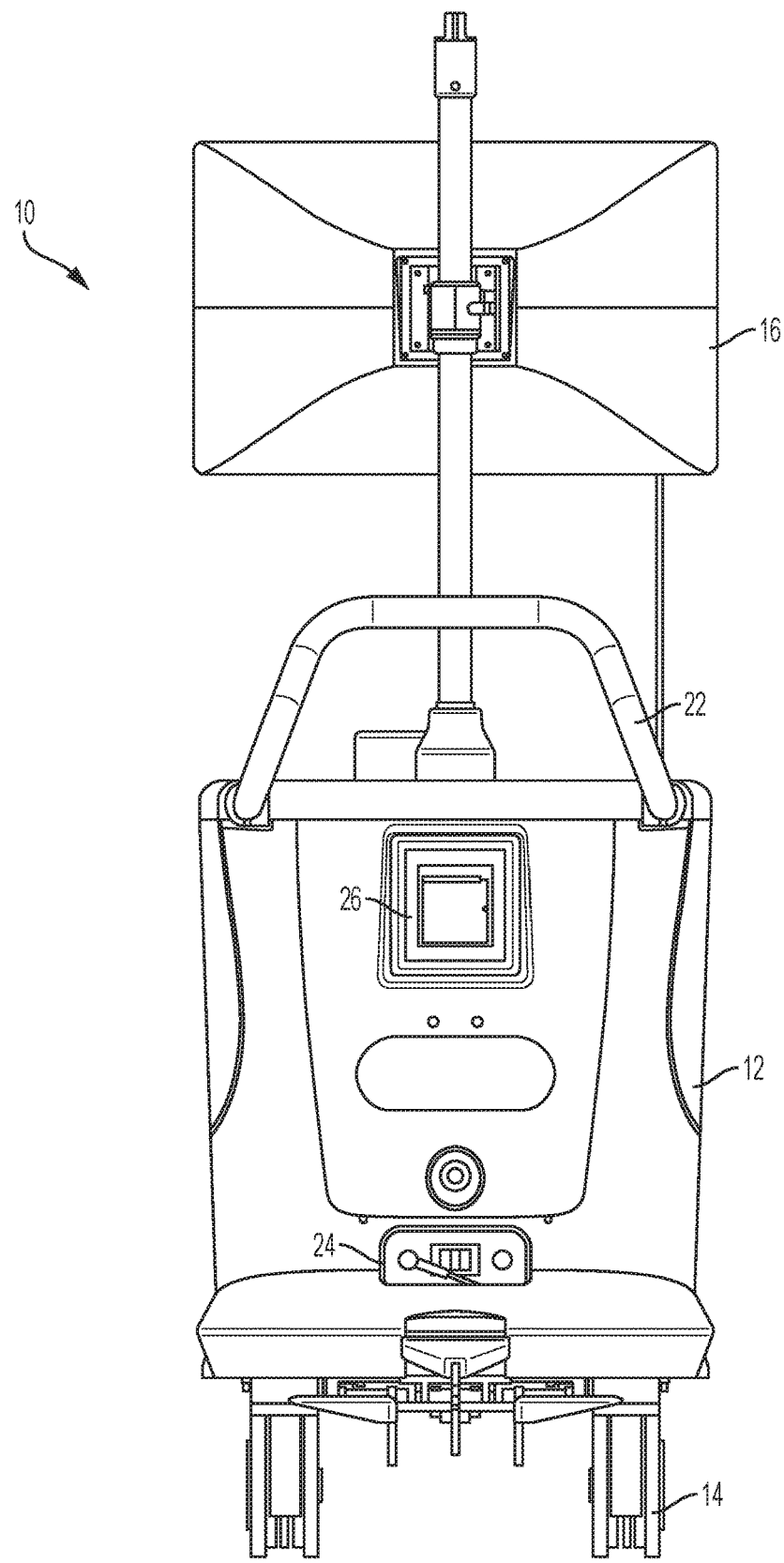
FIG. 3 is a rear view of the system shown in FIGS. 1 and 2 illustrating additional example features that can be included in the system.

System 10 can include a variety of other features and functionalities. FIG. 3 is a rear view of system 10 shown in FIGS. 1 and 2 illustrating additional example features that can be included on the system. In this example, system 10 includes a handle 22 extending outwardly from cabinet structure 12 to provide a surface that an operator can grasp to move the system from one location to another location. System 10 also includes a power connection 24. In different examples, system 10 may be powered via a wired connection to wall or mains power, via a rechargeable battery, or through a combination of power sources. Power connection 24 may be a socket to which an electrical cable can be connected or may be an electrical cable, for example that is retractable inside of cabinet structure 12, to enable connection to an external power source. Power delivered to system 10 via power connection 24 may be used to directly power the various electrical components of the system, such as a controller and/or pump, or may provide power to a battery contained within cabinet structure 12 that then powers the various components of the system.

In some examples, system 10 may also include a printer 26 that can provide printed summaries, reports, or other printed media relating to system 10. For example, printer 26 may be used to generate patient reports containing data related to a specific patient infusion procedure undertaken. The patient report may be incorporated into a patient's file, shared with the caregiver, or otherwise used to document care delivered using the infusion system. As another example, printer 26 may be used to generate maintenance reports indicating the status of one or more components within system 10, document maintenance undertaken on the system, or otherwise record action taken on the system.

Printer 26 can be communicatively coupled to a controller that controls the overall operation of system 10. In some examples, an operator may interact with the user interface 16 to request one or more reports or other printed outputs be generated using printer 26.

Although handle 22, power connection 24, and printer 26 are illustrated as being positioned on the rear side of cabinet structure 12 in the configuration of FIG. 3, it should be appreciated that the features may be positioned at other locations on system 10 while still providing the functionality described herein.

Figure 4:
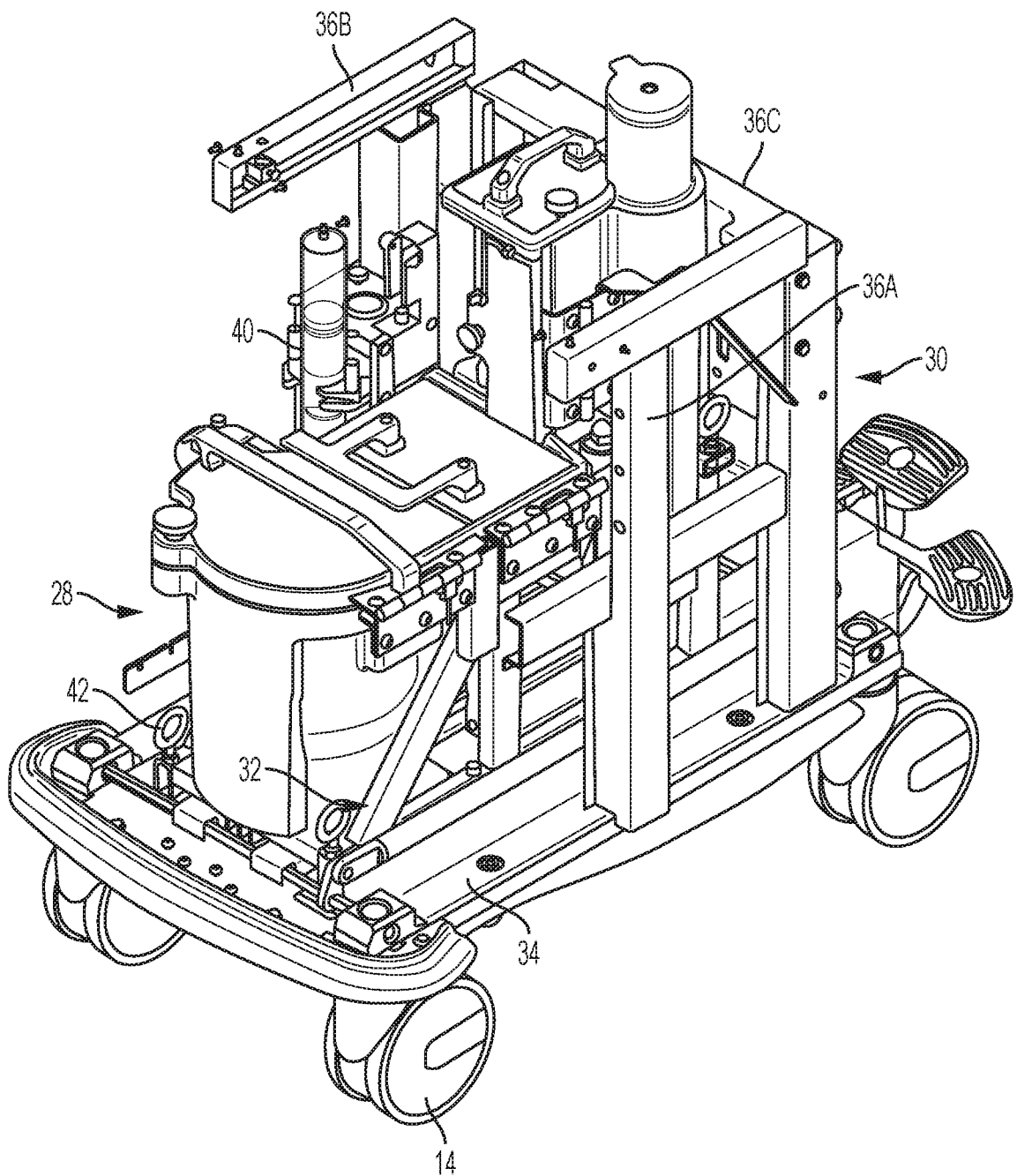
FIGS. 4 and 5 are perspective and top views, respectively, of the system of FIGS. 1-3 shown with the cabinet structure removed for purposes of illustration and illustrating an example shielding assembly arrangement.
Figure 5:
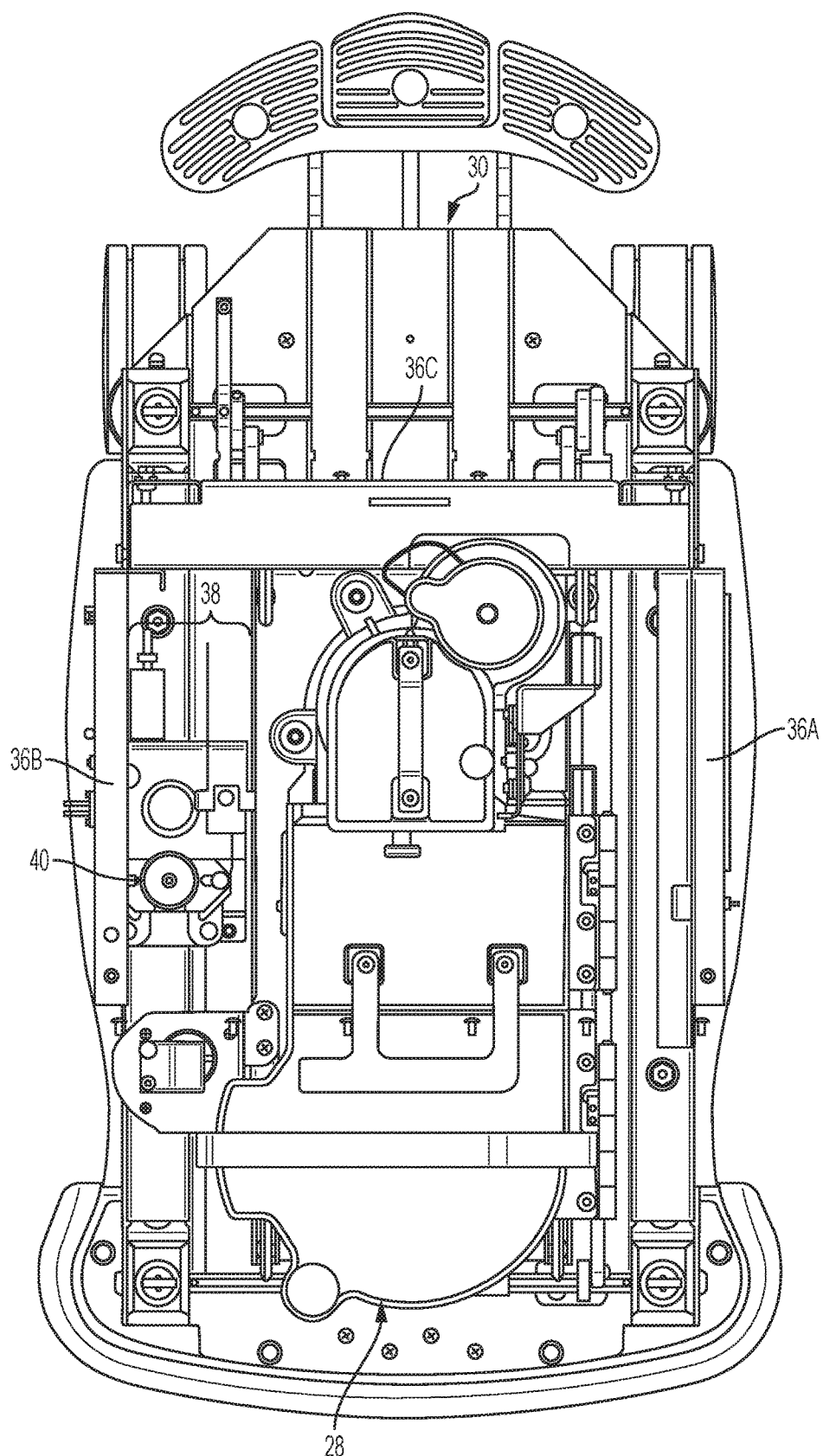

As briefly discussed above, system 10 may include a shielding assembly that blocks radioactive radiation emitted by radioactive materials within the system. FIGS. 4 and 5 are perspective and top views, respectively, of system 10 from FIGS. 1-3 shown with cabinet structure 12 removed for purposes of illustration and illustrating an example shielding assembly arrangement. As shown in this example, system 10 includes a shielding assembly 28 carried by a frame 30. In particular, in the illustrated configuration, shielding assembly 28 is mounted to a shielding assembly frame 32 which, in turn, is mounted to a cart frame 30.

In general, frame 30 may be any rigid structure that defines a surface configured (e.g., sized and/or shaped) to receive and hold shielding assembly 28. Frame 30 may have one or more horizontally oriented members 34 on which a bottom surface of shielding assembly 28 rests when the shielding assembly is inserted onto the frame. In some examples, frame 30 also includes one or more vertically extending members that extend along sidewalls of shielding assembly 28, when the shielding assembly is installed in the frame. For example, as illustrated in the configuration of FIG. 4, shielding assembly 28 includes a first vertical wall surface 36A, a second vertical wall surface 36B, and a rear vertical wall surface 36C that collectively define an opening configured to receive and surround around at least a portion of shielding assembly 28. Configuring system 10 with frame 30 can be useful to provide a structure that supports shielding assembly 28 and/or helps protect the shielding assembly from damage or inadvertent physical contact. In the illustrated configuration, wheels 14 are operatively (e.g., mechanically) connected to frame 30 and, more particularly, horizontally oriented member 34 of the frame. In other examples as indicated above, system 10 does not include wheels 14.

In some examples, a pump that pumps liquid through system 10 is carried by frame 30 inside of cabinet structure 12 (in examples in which system 10 includes an additional exterior cabinet structure). For example, with reference to FIG. 5, frame 30 defines a space 38 offset from shielding assembly 28 that is configured to receive a pump 40. In particular, with the illustrated example, space 38 is positioned between a second vertical wall surface 36B of frame 30 and shielding assembly 28, when the shielding assembly is installed on the frame. Space 38 can be configured (e.g., sized and/or shaped) to receive pump 40 and/or other components of system 10 such as a controller, one or more servomotors to control valves, or other operational hardware to enable system 10 to provide the functions described herein. Such an arrangement may be useful to co-locate hardware components of system 10 not in direct contact with radioactive materials with other components contained in shielding assembly 28 that are in direct contact with radioactive emissions emitted by radioactive liquid generated using the system.

In FIGS. 4 and 5, shielding assembly 28 is mounted to shielding assembly frame 32 which, in turn, can be installed on frame 30 that defines a mobile cart frame. For example, shielding assembly 28 may be physically and/or mechanically connected to shielding assembly frame 32, such that the shielding assembly is in direct physical contact with the shielding assembly frame. In turn, shielding assembly frame 32 can be received in a space defined by horizontally oriented member 34 and vertically oriented sidewalls 36A-C, e.g., such that the shielding assembly frame 32 is in physical contact with frame 30. Shielding assembly frame 32, similar to frame 30, may be a rigid structure that surrounds and or encloses at least a portion of the sidewalls of shielding assembly 28. For example, shielding assembly frame 32 may provide mechanical rigidity and/or support for shielding assembly 28 to allow the shielding assembly to be transported outside of system 10.

To enable efficient installation of shielding assembly 28 onto frame 30, shielding assembly frame 32 may include multiple hooks 42 positioned about a perimeter of the shielding assembly that can be engaged by a lifting device to lift shielding assembly frame 32, and the shielding assembly carried 28 thereon, for installation onto cart frame 30. During assembly or maintenance, an operator may attach a lifting mechanism such as a crane or block and tackle to hooks 42 to enable shielding assembly 28 to be lifted and installed on cart frame 30. Pump 40 and other components of system 10 carried by frame 30 outside of shielding assembly 28 may or may not also be physically attached to shielding assembly frame 32. In some examples, shielding assembly frame 32 carries only shielding assembly 28 and does not carry other components that are received on frame 30 adjacent to shielding assembly 28, such as pump 40, a controller controlling the operation of system 10, and other related hardware or software.

When system 10 includes frame 30 and/or shielding assembly frame 32, each frame may typically be made of a rigid material such as a rigid metal or plastic that provide structural integrity to the overall system. While FIGS. 4 and 5 illustrate one example arrangement of respective frames that can receive various hardware components of system 10, it should be appreciated that in other configurations, system 10 does not include a separate shielding assembly frame and cart frame, or may have a different configuration or arrangement of frame members than that illustrated.

Shielding assembly 28 and frame 30 can receive and hold various components of system 10 that enable the system to perform the functions attributed to it herein. For example, as briefly indicated above, system 10 may include a radioisotope generator that generates radioactive eluate via an elution with an eluant. The system may include a radioisotope generator that contains radioactive material in order to generate the radioactive eluate via elution. The system may also include multiple detectors, such as a beta detector and a gamma detector, positioned downstream of the radioisotope generator to measure radioactive emissions emitted by radioactive eluate produced using the generator.

Figure 6:
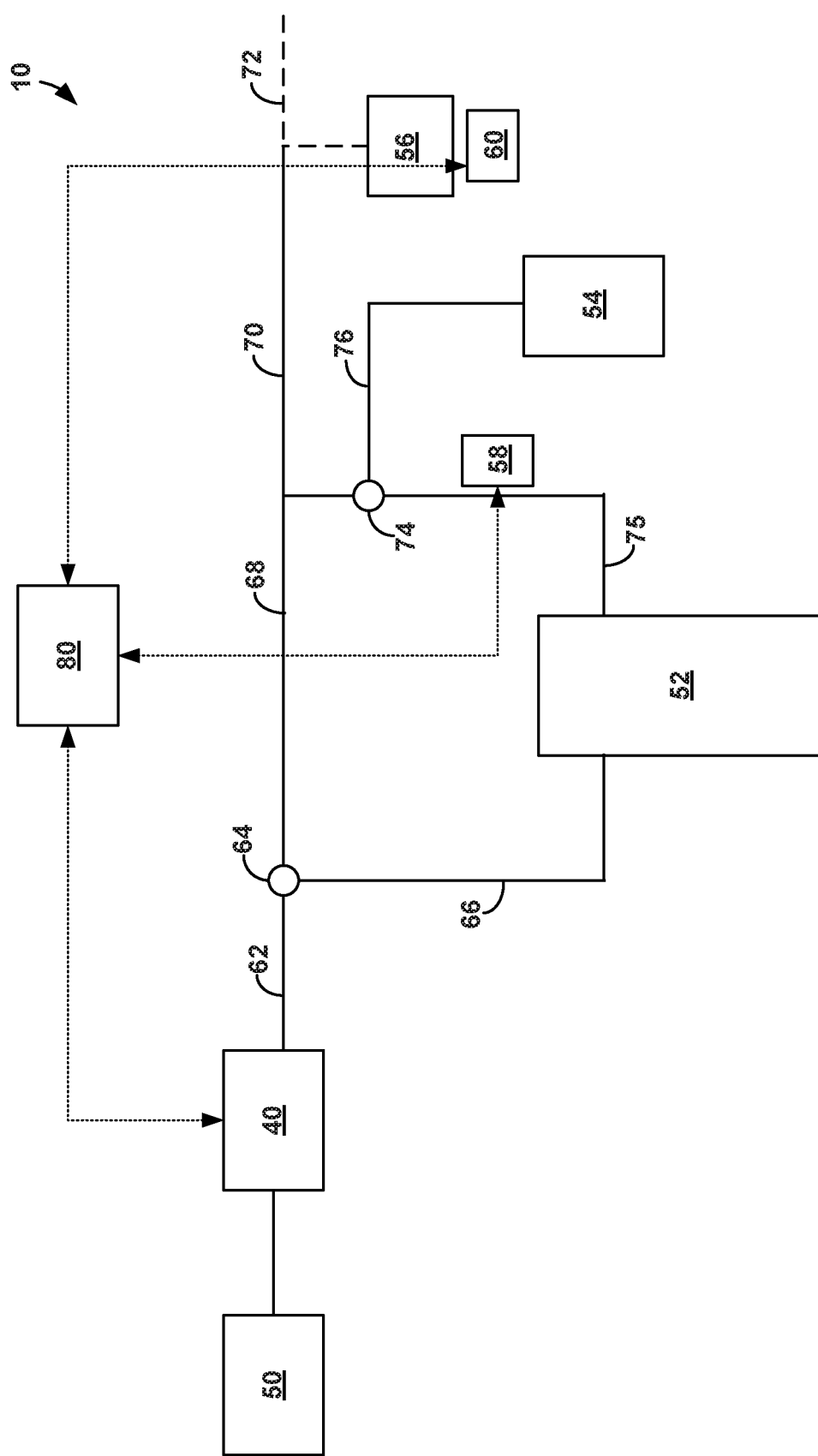
FIG. 6 is a block diagram illustrating an example arrangement of components that can included in the system of FIGS. 1-5 to generate radioactive eluate and detect radioactive emissions.

FIG. 6 is a block diagram illustrating an example arrangement of components that can included in system 10 to generate radioactive eluate and detect radioactive emissions. In the example, system 10 includes an eluant reservoir 50, previously-described pump 40, a radioisotope generator 52, a waste container 54, an eluate-receiving container 56, a beta detector 58, and a gamma detector 60. One or more fluid tubing lines can connect the various components of system 10 together.

For example, in the configuration of FIG. 6, pump 40 receives eluant from eluant reservoir 50, pressurizes the eluant, and discharges pressurized eluant into an eluant line 62. A first diverter valve 64 controls the flow of eluant to one of a radioisotope generator inlet line 66 and a radioisotope generator bypass line 68. Eluant flowing through radioisotope generator bypass line 68 bypasses radioisotope generator 52 and can flow directly into an infusion tubing line 70. Infusion tubing line 70 can be in fluid communication with either eluate-receiving container 56 (e.g., during a quality control procedure) or a patient catheter 72 (e.g., during a patient infusion procedure). A second multi-way valve 74 controls a flow of eluate generated by elution within radioisotope generator 52 and received from a radioisotope generator discharge line 75 to either the infusion tubing line 70 or a waste line 76. Waste line 76 can be connected to waste container 54.

During operation, radioisotope generator 52 can generate radioactive eluate via elution. For example, radioisotope generator 52 may be a strontium-rubidium generator containing Sr-82 bound on a support material, such as stannic oxide or tin oxide. Rb-82 is a daughter decay product of Sr-82 and binds less strongly to the support material than the strontium. As pressurized eluant from eluant reservoir 50 is passed through the radioisotope generator, the eluant may release Rb-82 so as to generate a radioactive eluate. For example, when the eluant is a saline (NaCl) solution, sodium ions in the saline can displace Rb-82 in the generator so as to elute a Rb-82 chloride solution.

In other examples, radioisotope generator 52 can generate different types of decay products besides Rb-82. The type of daughter decay product produced by radioisotope generator 52 can be controlled by selecting the type of radioisotope loaded onto the generator support material. Example types of radioisotope generators that can be used as radioisotope generator 52 include, but are not limited to, $^{99}$Mo/$^{99m}$Tc (parent molybdenum-99 bound on a support material to produce daughter decay product technetium-99m); $^{90}$Sr/$^{90}$Y (parent strontium-90 bound on a support material to produce daughter decay product yttrium-90); $^{188}$W/$^{188}$Re (parent tungsten-188 bound on a support material to produce daughter decay product rhenium-188); and $^{68}$Ge/$^{68}$Ga (parent germanium-68 bound on a support material to produce daughter decay product gallium-68). Yet other types of radioisotope generators that can be used as radioisotope generator 52 include: $^{42}$Ar/$^{42}$K; $^{44}$Ti/$^{44}$Sc; $^{52}$Fe/$^{52m}$Mn; $^{72}$Se/$^{72}$As; $^{83}$Rb/$^{83m}$Kr; $^{103}$Pd/$^{103m}$Rh; $^{109}$Cd/$^{109m}$Ag; $^{113}$Sn/$^{113m}$In; $^{118}$Te/$^{118}$Sn; $^{132}$Te/$^{132}$I; $^{137}$Cs/$^{137m}$Ba; $^{140}$Ba/$^{140}$La; $^{134}$Ce/$^{134}$La; $^{144}$Ce/$^{144}$Pr; $^{140}$Nd/$^{140}$Pr; $^{166}$Dy/$^{166}$Ho; $^{167}$Tm/$^{167m}$Er; $^{172}$Hf/$^{172}$Lu; $^{178}$W/$^{178}$Ta; $^{191}$Os/$^{191m}$Ir; $^{194}$Os/$^{194}$Ir; $^{226}$Ra/$^{222}$Rn; and $^{225}$Ac/$^{213}$Bi.

To measure the radioactivity of one or more radioisotopes in the radioactive eluate generated via elution in system 10, the system may include multiple detectors configured to receive and measure different radioactive emissions produced by the radioactive eluate. For example, as shown in the example of FIG. 6, system 10 may include a beta detector 58 and a gamma detector 60. Beta detector 58 can be positioned downstream of radioisotope generator 52 to measure beta emissions emitted by radioactive eluate produced by the generator. Gamma detector 60 can also be positioned downstream of radioisotope generator 52 to measure gamma emissions emitted by the radioactive eluate produced by the generator.

The specific locations of beta detector 58 and gamma detector 60 can vary. However, in the example of FIG. 6, beta detector 58 is positioned between an outlet of radioisotope generator 52 and second multi-way valve 74, which is upstream of waste container 54 and infusion tubing 70 along the fluid pathway from the radioisotope generator. By contrast, gamma detector 60 is positioned downstream of the outlet of the radioisotope generator 52 and beta detector 58. For example, gamma detector 60 may be positioned downstream of the second multi-way valve 74 along the fluid pathway of infusion tubing 70.

In operation, beta detector 58 can measure beta emissions emitted by radioactive eluate generated by and discharged from radioisotope generator 52. In some examples, beta detector 58 is positioned in close proximity to radioisotope generator discharge line 75 such that the beta detector can detect beta emissions emitted from radioactive eluate present in the discharge line. The radioactive eluate may be flowing through the radioisotope generator discharge line 75 toward infusion tubing 70 and/or waste line 76. Alternatively, the radioactive eluate may be supplied to the radioisotope generator discharge line 75 and held static (non-flowing) while the beta detector 58 measures beta emissions emitted from the radioactive eluate. In yet other configurations, an eluate-receiving reservoir may be provided in fluid communication with radioisotope generator discharge line 75, for example via an additional multi-way valve, and beta detector 58 positioned to measure beta emissions from the radioactive eluate supplied to the eluate-receiving reservoir. In any configuration, beta detector 58 may measure beta emissions from radioactive eluate generated by the generator in order to detect and/or quantify one or more radioisotopes present in the radioactive eluate.

System 10 also includes a gamma detector 60. In operation, gamma detector 60 can measure gamma emissions emitted by radioactive eluate generated by and discharged from radioisotope generator 52. For example, radioactive eluate generated by radioisotope generator 52 may be discharged through radioisotope generator discharge line 75, diverter valve 74, infusion tubing 70, and supplied to eluate-receiving container 56. Gamma detector 60 may be positioned in close proximity to eluate-receiving container 56 in order to detect gamma emissions emitted by the portion of radioactive eluate delivered to the receiving container. For example, a clinician may attach an outlet of infusion tubing 70 to an inlet of eluate-receiving container 56 in order to supply radioactive eluate to the receiving container. Upon subsequently controlling pump 40 to generate radioactive eluate that is supplied to the eluate-receiving container 56, gamma detector 60 may measure gamma emissions emitted by the radioactive eluate.

While FIG. 6 illustrates one example location for gamma detector 60, other locations may be used. For example, gamma detector 60 may be positioned in close proximity to a tubing line downstream of radioisotope generator 52, such as radioisotope generator discharge line 75 and/or infusion tubing 70. In these examples, gamma detector may measure gamma emissions emitted by radioactive eluate flowing through the tubing line or a static (non-flowing) portion of radioactive eluate held within the tubing line. Independent of the specific location of the gamma detector within system 10, gamma detector 60 may measure gamma emissions from radioactive eluate generated by the radioisotope generator 52 in order to detect and/or quantify one or more radioisotopes present in the radioactive eluate.

For example, gamma emissions measured by gamma detector 60 may be used to detect and/or quantify one or more contaminating radioisotopes in radioactive eluate generated by radioisotope generator 52, while beta emissions measured by beta detector 58 may be used to detect and/or quantify one or more radioisotopes in the radioactive eluate targeted for patient infusion. In some examples, beta detector 58 measures beta emissions from radioactive eluate flowing through radioisotope generator discharge line 75 toward eluate-receiving container 56. Once the radioactive eluate has passed beta detector 58 and filled eluate-receiving container 56, either partially or fully, gamma detector 60 may measure gamma emissions from that portion of radioactive eluate supplied to the receiving container. In these applications, gamma detector 60 may measure gamma emissions from a portion of radioactive eluate also emitting beta emissions which were detected by beta detector 58 as the radioactive eluate flowed towards the eluate-receiving container 56. In other operational configurations, beta detector 58 and gamma detector 60 may not measure radioactive emissions from the same portion or volume of radioactive eluate but may measure radioactive emissions from different portions of radioactive eluate.

Radioisotope generator system 10 in the example of FIG. 6 also includes a controller 80. Controller 80 may be communicatively coupled (e.g., via a wired or wireless connection) to the various pump(s), valves, and other components of system 10, including beta detector 58 and gamma detector 60, so as to send and receive electronic control signals and information between controller 80 and the communicatively coupled components. For example, controller 80 may receive data generated by beta detector 58 indicative of the magnitude of beta emissions detected by the detector. Controller 80 may further receive data generated by gamma detector 60 indicative of the amount and type (e.g., spectral distribution) of gamma emissions detected by the detector. Controller 80 may further process the data to determine an activity of different isotopes in the eluate from which beta detector 58 and gamma detector 60 detected beta emissions and gamma emissions, respectively. Controller 80 may also manage the overall operation of radioisotope generator system 10, including initiating and controlling patient dosing procedures, controlling the various valves and pump(s) in the system, receiving and processing signals from beta detector 58 and gamma detector 60, and the like.

In operation, beta detector 58 can detect beta emissions emanating from radioactive eluate positioned in front of the detector. Beta detector 58 can include a variety of components to detect and process beta emission signals. In some configurations, beta detector 58 is implemented using a solid-state detector element such as a PIN photodiode. In these configurations, the solid-state detector element can directly convert impinging radioactive energy into electrons in the semiconductor material of the detector. The electrons can then be amplified into a usable signal (e.g., received by controller 80). In some examples, beta detector 58 includes a scintillator, which converts impinging radioactive energy into light pulses, which is then captured by an attached photon-to-electron converter such as a photomultiplier tube or avalanche photodiode. The choice of the scintillator can determine the sensitivity and the countrate performance. For example, beta detector 58 may be implemented using a plastic scintillator when high sensitivity and high countrate performance are desired.

During operation, gamma detector 60 can detect gamma ray emissions emanating from a portion of eluate positioned in close proximity to the detector, e.g., statically positioned in eluate-receiving container 56. Gamma detector 60 may include a variety of different components to detect and process gamma ray radiation signals, such as a pulse sorter (e.g., multichannel analyzer), amplifiers, rate meters, peak position stabilizers, and the like. In one example, gamma detector comprises a scintillation detector. In another example, gamma detector comprises a solid-state semiconductor detector.

The specific type of gamma detector selected for detector 60 can vary based on a variety of factors such as, e.g., the required resolution of the detector, the physical requirements for practically implementing the detector in a system (e.g., cooling requirements), the expected sophistication of the personnel operating the detector, and the like. In some applications, gamma detector 60 is a scintillator-type detector, such as a comparatively low-resolution alkali halide (e.g., NaI, CsI) or bismuth germanate (e.g., $Bi_4Ge_3O_{12}$, or BGO). In other applications, gamma detector 60 incorporates a higher-Z metallic species. An example is lutetium oxyorthosilicate, $Lu_2(SiO_4)O(Ce)$ or LSO, which, though slightly better in resolution than BGO, may have limited applicability because of its relatively high intrinsic radiation. As another example, gamma detector 60 may be a cerium-doped lanthanum, such as $LaCl_3(Ce)$ or $LaBr_3(Ce)$.

In other applications, gamma detector 60 is a solid-state semiconductor-type detector, such as a planar germanium detector. For instance, as another example, gamma detector 60 may be a solid-state semiconductor-type telluride detector, such as cadmium-telluride or cadmium-zinc-telluride semiconductor detector. Gamma detector 60 may be operated at room (ambient) temperature or may be cooled below room temperature (e.g., by a cooling device incorporated into radioisotope generator system 10) to increase the resolution of detector.

Gamma detector 60 can generate gamma ray spectroscopy data. For example, the detector may include a passive material that waits for a gamma interaction to occur in the detector volume. Example interactions may be photoelectric effects, Compton effects, and pair production. When a gamma ray undergoes a Compton interaction or pair production, for instance, a portion of the energy may escape from the detector volume without being absorbed so that the background rate in the spectrum is increased by one count. This count may appear in a channel below the channel that corresponds to the full energy of the gamma ray.

A voltage pulse produced by gamma detector 60 can be shaped by a multichannel analyzer associated with the detector. The multichannel analyzer may take a small voltage signal produced by the detector, reshape it into a Gaussian or trapezoidal shape, and convert the signal into a digital signal. The number of channels provided by the multichannel analyzer can vary but, in some examples, is selected from one of 512, 1024, 2048, 4096, 8192, or 16384 channels. The choice of the number of channels may depend on the resolution of the system, the energy range being studied, and the processing capabilities of the system.

Data generated by gamma detector 60 in response to detecting gamma ray emissions may be in the form of a gamma ray spectrum that includes peaks. The peaks may correspond to different energy levels emitted by the same or different isotopes within an eluate sample under analysis. These peaks can also be called lines by analogy to optical spectroscopy. The width of the peaks may be determined by the resolution of the detector, with the horizontal position of a peak being the energy of a gamma ray and the area of the peak being determined by the intensity of the gamma ray and/or the efficiency of the detector.

During operation (either a patient infusion procedure, a quality control procedure, a calibration procedure, or other operating procedure), controller 80 may receive data generated by beta detector 58 and/or gamma detector 60 indicative of beta emissions and gamma emissions detected by the respective detectors. Controller 80 may process the data to determine an activity of one or more radioisotopes in the radioactive eluate from which beta detector 58 and/or gamma detector 60 detected beta emissions and/or gamma emissions, respectively. Controller 80 may manage operation of system 10 based on the determined activity of the one or more radioisotopes.

For example, when radioisotope generator 52 is implemented using a strontium-rubidium radioisotope generator, controller 80 may receive data from beta detector 58 indicative of beta emissions measured from radioactive eluate flowing through radioisotope generator discharge line 75. Controller 80 may not be able to resolve different radioisotopes from the beta emissions measured by beta detector 58 but may instead be programmed to assume that all such beta emissions are attributable to radioactive Rb-82 present in the radioactive eluate, since Rb-82 may be expected to be the predominant radioactive species present. Accordingly, with reference to data stored in memory, controller 80 may determine an activity of Rb-82 present in the radioactive eluate supplied from radioisotope generator 52 based on a cumulative magnitude of beta emissions measured by beta detector 58.

Controller 80 may further receive in such examples data from gamma detector 60 indicative of gamma emissions measured from a portion of radioactive eluate supplied to eluate-receiving container 56. Controller 80 may determine which species of one or more other radioisotopes are present in the radioactive eluate and/or an activity level of those species based on the received data from the gamma detector. For example, controller 80 may determine which species of radioisotopes and/or an activity of those radioisotopes are present in the radioactive eluate based on the amount and type (e.g., spectral distribution) of gamma emissions detected by gamma detector 60. For instance, controller 80 may determine an activity of Sr-82 and/or Sr-85 present in the radioactive eluate, if any, which can be contaminants to the Rb-82 radioisotope intended for patient infusion procedure.

Controller 80 may control operation of system 10 based on the measured activity of the radioisotope intended for patient infusion (for example Rb-82) and/or based on the measured activity of one or more radioisotopes species that are contaminants to such radioisotope (for example, Sr-82 and/or Sr-85). Controller 80 may compare the activity of one or more individual isotopes to one or more thresholds stored in memory and control operation of system 10 based on the comparison. Controller 80 may take a variety of actions when a threshold is exceeded. As one example, controller 80 may initiate a user alert (e.g., a visual, textual, mechanical (e.g., vibratory), audible user alert), e.g., by controlling user interface 16 to deliver the alert. As another example, controller 80 may shut down pump 40 so as to cease generating eluate. As yet another example, controller 80 may control second multi-way valve 74 to divert elute from infusion tubing 70 to waste line 76.

As noted above, system 10 may include a waste container 54 and an eluate-receiving container 56. Waste container 54 and eluate-receiving container 56 may each be structures configured to receive and hold liquid received from upstream tubing. In different examples, waste container 54 and/or eluate-receiving container 56 may be reservoirs permanently formed in shielding assembly 28 (FIGS. 4 and 5) or maybe removable from the shielding assembly. For example, waste container 54 and/or eluate-receiving container 56 may be a vessel (e.g., bottle, vial, canister, or other receptacle) configured to receive radioactive eluate, each of which is removable from shielding assembly 28.

In general, waste container 54 is intended to receive radioactive eluate produced upon activation of system 10, as pump 40 pumps eluant through radioisotope generator 52 toward waste container 54. For example, in operation, pump 40 may pump eluant through radioisotope generator 52 while controller 80 controls second multi-way valve 74 to direct radioactive eluate toward waste container 54. Upon determining that the radioactive eluate produced by radioisotope generator 52 has reached a threshold level of activity, controller 80 may control second multi-way valve 74 to direct the radioactive eluate to infusion tubing 70 (and to patient catheter 72 or eluate-receiving container 56 coupled thereto) instead of toward waste container 54. Controller 80 may determine that the radioactive eluate produced by radioisotope generator 52 has a threshold level of activity based on the beta emissions measured by beta detector 58, e.g., and threshold information stored in memory associated with the controller. In different examples, waste container 54 may be sized to hold a volume of liquid received from radioisotope generator 52 of at least 100 mL, such as at least 250 mL, or greater than or equal to 500 mL. As one example, waste container 54 may be sized to hold from 250 mL to 1 L.

In contrast to waste container 54 which is intended to receive radioactive eluate produced by radioisotope generator 52 that is designated as waste, eluate-receiving container 56 can receive patient-infusible radioactive eluate produced the radioisotope generator. Eluate-receiving container 56 may receive and hold a portion of the radioactive eluate produced by the radioisotope generator (e.g., after controller 80 has actuated multi-way valve 74 to redirect the radioactive eluate being produced from waste line 76 to infusion tubing 70). While eluate-receiving container 56 is being filled with radioactive eluate and/or after the eluate-receiving container has filled, gamma detector 60 may measure gamma emissions emanating from the radioactive eluate. In some examples, beta detector 58 measures beta emissions from radioactive eluate flowing through radioisotope generator discharge line 75 as the eluate flows to eluate-receiving container 56, whereupon gamma detector 60 measures gamma omissions from that same portion of eluate whose beta emissions were previously measured by the beta detector.

Controller 80 may determine an activity of one or more radioisotopes present in the radioactive eluate received by an eluate-receiving container 56 based on the gamma emissions measured by gamma detector 60. If controller 80 determines that an activity of one or more radioisotopes present in the radioactive eluate exceeds an allowable limit (e.g., with reference to thresholds stored in a memory associate with the controller) the controller may alert the user, for example via user interface 16. Additionally or alternatively, controller 80 may prevent a subsequent patient infusion procedure until it is determined that a radioisotope generator 52 (or replacement thereof) can produce radioactive eluate that does not contain one or more radioisotopes that exceed allowable limit. In this way, gamma detector 60 may be positioned to evaluate the quality of radioactive eluate produced by radioisotope generator 52 and help ensure that the radioactive eluate produced by the radioisotope generator (e.g., eluate that will subsequently be produced during one or more subsequent elutions of the generator) is safe for patient infusion.

Although eluate-receiving container 56 can have a number of different configurations, in some examples, the eluate-receiving container is sized smaller than waste container 54. For example, eluate-receiving container 56 may be sized to receive and hold a volume of liquid less than 500 mL, such as less than 250 mL or less than 100 mL. In one example, eluate-receiving container is sized to hold from 10 mL to 100 mL. Further, while eluate-receiving container 56 can be implemented using a variety of different types of containers, in some examples, the eluate-receiving container is fabricated of glass or plastic, such as a glass vial or bottle, or a plastic syringe or container. Such a structure may be useful in that the glass vial may limit the extent to which gamma emissions are blocked or attenuated by the eluate-receiving container, or may be more uniform, allowing gamma detector 60 to adequately detect gamma emissions emitted by the radioactive eluate delivered to the container.

In practice, eluate-receiving container 56 may be reused for multiple quality control procedures or may be disposable after each quality control procedure. For instance, in some applications, an operator may select a new, previously unused, eluate-receiving container and insert the container into an appropriate compartment of shielding assembly 28. After performing the quality control procedure, the operator can remove the eluate-receiving container, discard the contents of the container appropriately, and then discard the container itself. Typically, waste container 54 is a reusable structure, for example fabricated from metal glass or other compatible material, that may be removed and emptied from shielding assembly 28 periodically but is not discarded after use.

Figure 7A:
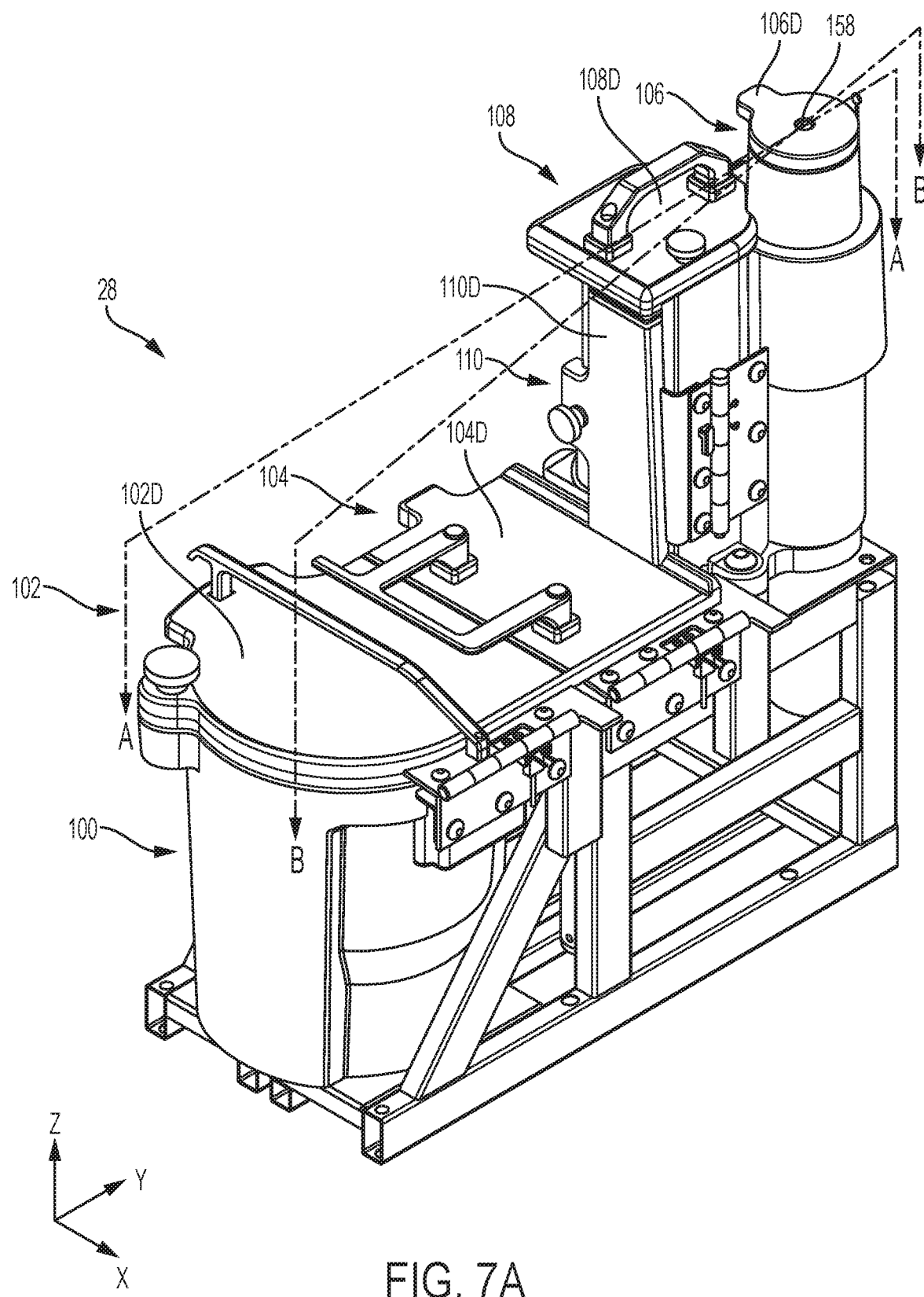
FIGS. 7A and 7B are perspective views of an example configuration of the shielding assembly from FIGS. 4 and 5 shown removed from the cart frame for purposes of illustration.
Figure 7B:
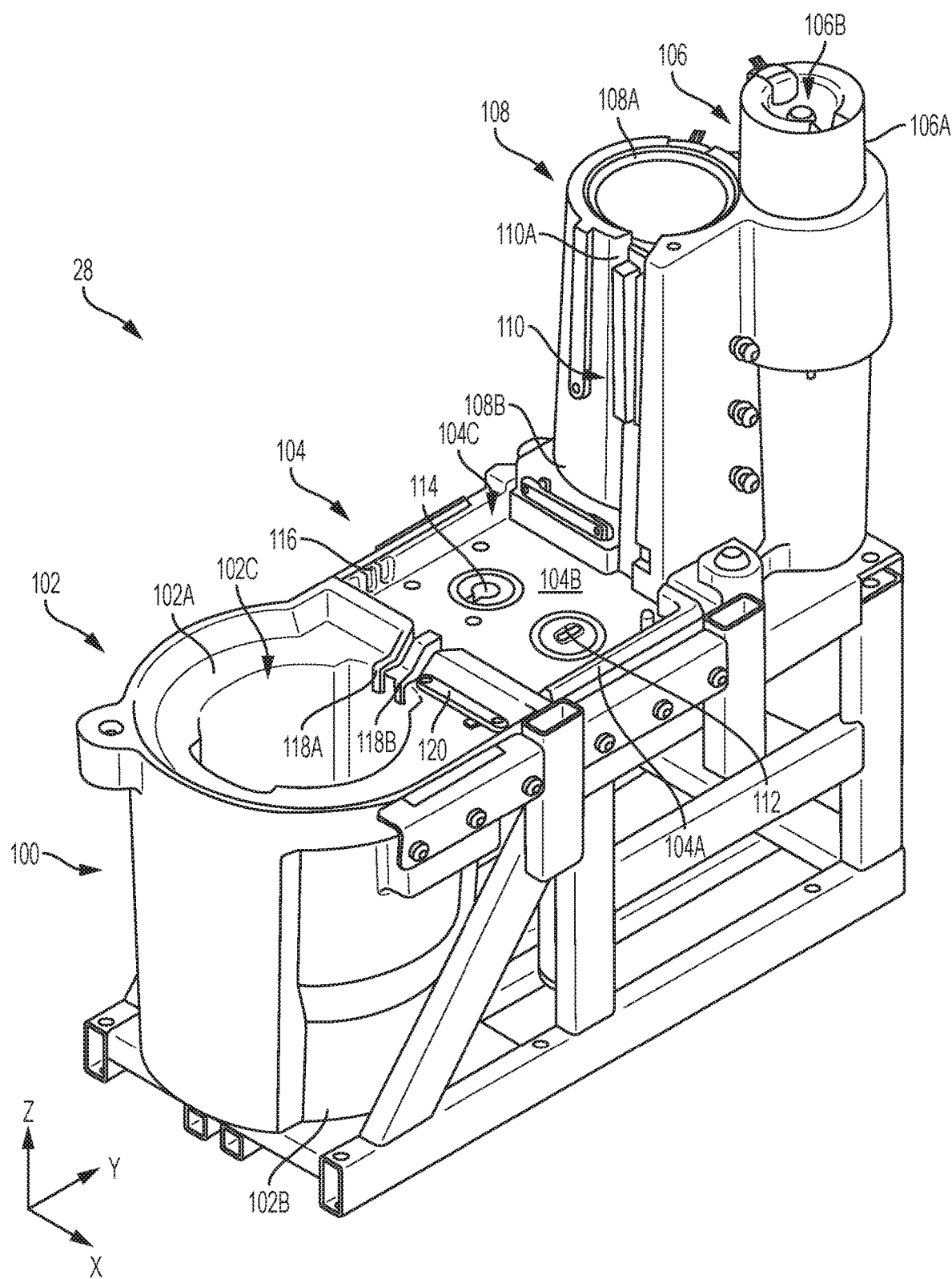

As discussed above with respect to FIGS. 4 and 5, system 10 may include a shielding assembly 28. Shielding assembly 28 can house various components of system 10 exposed to and/or in contact with radioactive eluate. FIGS. 7A and 7B are perspective views of an example configuration of shielding assembly 28 from FIGS. 4 and 5, shown removed from cart frame 30 for purposes of illustration. FIG. 7A illustrates shielding assembly 28 with doors attached, while FIG. 7B illustrates the shielding assembly with doors removed to show an example arrangement of internal features.

In general, shielding assembly 28 may be formed of one or more materials that provide a barrier to radioactive radiation. The type of material or materials used to fabricate the shielding assembly and the thicknesses of those materials may vary, for example, depending on the type and size of radioisotope generator 52 used in the system and, correspondingly, the amount of radiation shielding needed. In general, the thickness and/or configuration of the radiation shielding material used to form shielding assembly 28 may be effective to attenuate radiation emanating from inside of the shielding assembly to a level which is safe for operating personnel to work around system 10. For example, when a new strontium-rubidium generator is installed in shielding assembly 28, it may contain 200 millicuries of radiation. Shielding assembly 28 may block that radiation so the radiation level outside of the shielding assembly does not exceed that which is allowable for operating personnel surrounding the shielding assembly.

In some examples, shielding assembly 28 is fabricated from lead or lead alloys or other high density materials. Shielding assembly 28 may have a wall thickness greater than 25 millimeters, such as greater than 50 millimeters. For example, shielding assembly 28 may have a wall thickness ranging from 50 millimeters to 250 millimeters, such as from 65 millimeters to 150 millimeters. Further, as discussed in greater detail below, shielding assembly 28 may include different compartments specifically arranged relative to each other to effective shield radiation sources from radiation sensitive components.

With reference to FIGS. 7A and 7B, shielding assembly 28 can have at least one sidewall 100 that provides a barrier to radioactive radiation and defines a compartment configured to receive one or more components of system 10. In some examples, shielding assembly 28 defines only a single compartment, e.g., containing at least radioisotope generator 52 (FIG. 6). In other examples, including the example illustrated in FIGS. 7A and 7B, shielding assembly 28 has a plurality of compartments each separated from each other by at least one wall of radiation shielding material. For example, shielding assembly 28 may include a first compartment 102 configured to receive radioisotope generator 52, a second compartment 104 configured to receive beta detector 58, and a third compartment 106 configured to receive gamma detector 60. Shielding assembly 28 can include one or more additional compartments, such as a fourth compartment 108 configured to receive waste container 54 and/or a sidewall compartment 110 configured to receive one or more fluid tubing lines.

In general, the different compartments of shielding assembly 28 may be configured to position the different components received in each respective compartment at a desired location relative to each other. For example, first compartment 102 that is configured to receive radioisotope generator 52 may be positioned at a location upstream of second compartment 104 and third compartment 106. As a result, radioactive eluate generated by radioisotope generator 52 can flow downstream to beta detector 58 and/or gamma detector 60 in order to measure an activity of one or more radioactive species that may be present in the radioactive eluate. As another example, when gamma detector 60 is located downstream of beta detector 58, second compartment 104 that is configured to receive the beta detector can be positioned at a location upstream of third compartment 106 that is configured to receive gamma detector 60.

Positioning radioisotope generator 52 relative to beta detector 58 and/or gamma detector 60 via shielding assembly 28 can be useful to help properly shield the detectors from radioactive radiation emitted by the generator. As discussed above, radioisotope generator 52 can contain a radioactive material, for example strontium-82, which emits radioactive radiation. Nuclear decay of the radioactive material contained in radioisotope generator 52 can produce a decay product, or isotope, that is released into eluant pumped through the generator for injection into a patient undergoing a diagnostic imaging procedure. Since radioisotope generator 52 provides the source of nuclear material for the entire radioisotope generator system, the magnitude of radioactive admissions emitted by the generator, and more particularly radioactive material contained on and/or in the generator, may provide the strongest radioactive admissions signal in the system. As a result, if radioisotope generator 52 is not properly shielded from beta detector 58 and/or gamma detector 60, the detectors may be overwhelmed by detection of radioactive emissions emitted from the generator itself as opposed to radioactive emissions from the radioactive eluate generated by the generator, which may be desirably measured. Accordingly, shielding assembly 28 can be configured to help shield beta detector 58 and gamma detector 60 from radioisotope generator 52 while still allowing radioactive eluate produced by the generator to flow from one compartment to another compartment, for example, to allow the beta detector and the gamma detector to detect emissions from the eluate.

In some examples, radioisotope generator 52, beta detector 58, and gamma detector 60 are each positioned in different planes both horizontally and vertically. For example, shielding assembly 28 may be divided into an infinite number of infinitesimally thick planes extending in the X-Y direction indicated on FIGS. 7A and 7B and positioned at different vertical elevations in the Z-direction indicated on the figures (horizontal planes). Similarly, shielding assembly 28 may be divided into an infinite number of infinitesimally thick planes extending in the Z-X direction indicated on FIGS. 7A and 7B and positioned at different locations along the length of the assembly in the Y-direction indicated on the figures (vertical planes). Radioisotope generator 52, beta detector 58, and gamma detector 60 may be arranged relative to each other so they are each in a different horizontal plane and/or a different vertical plane. When so arranged, there may be at least one horizontal plane and/or at least one vertical plane that intersects a respective one of radioisotope generator 52, beta detector 58, and gamma detector 60 but does not intersect the other two components. Such an arrangement may help maximize a distance between radioisotope generator 52 and beta detector 58 and/or gamma detector 60, for example, to increase an amount of shielding present between the radioisotope generator and one or both detectors.

In some configurations, gamma detector 60 is positioned at a higher elevation (e.g., in the positive Z-direction indicated on FIGS. 7A and 7B) than the elevation at which radioisotope generator 52 is positioned. Additionally or alternatively, gamma detector 60 may be positioned at a location that is a laterally offset (e.g., in the X-direction and/or Y-direction indicated on FIGS. 7A and 7B) relative to radioisotope generator 52. Offsetting gamma detector 60 relative to radioisotope generator 52 both vertically and laterally may be useful to help maximize an amount of shielding material present between the gamma detector and the radioisotope generator.

Each compartment of shielding assembly 28 may define a cavity that partially or fully surrounds a respective component received in the compartment, e.g., to partially or fully surround the component with radioactive shielding material. In the example of FIGS. 7A and 7B, first compartment 102 is defined by a sidewall 102A and a base or bottom wall 102B. The sidewall 102A may extend vertically upwardly (in the positive Z-direction indicated on FIGS. 7A and 7B) from the base wall 102B and define an opening 102C (on FIG. 7B) through which radioisotope generator 52 can be inserted.

Second compartment 104 may also include a sidewall 104A and a base or bottom wall 104B. The sidewall 104A may extend vertically upwardly (in the positive Z-direction indicated on the figures) from the base wall 104B to form a cavity bound collectively by the sidewall 104A and the base wall 104B. In some examples, the sidewall 104A may also extend vertically downwardly (in the negative Z-direction indicated on the figures) from the base wall 104B to form an additional cavity on the bottom side of the base wall bound by the sidewall 104A and, on the top side, by base wall 104B. Independent of whether sidewall 104A extends vertically above and/or below base wall 104B, in configurations in which second compartment 104 includes base wall 104B, an opening 112 may be formed through the base wall 104B. The opening may be a region extending through the thickness of base wall 104B that is devoid of radiation shielding material. When so configured, beta detector 58 may be positioned on one side of base wall 104B at opening 112 and/or extending through the opening. For example, beta detector 58 may be positioned under base wall 104B and surrounded by a portion of sidewall 104A extending vertically downwardly from the base wall.

In instances in which beta detector 58 is positioned on one side of base wall 104B (e.g., on underside of the base wall as discussed above), a tubing line can be positioned on the opposite side of the base wall. For example, a tubing line that is part of an infusion tubing circuit may be positioned in second compartment 104, for example with the tubing line positioned over opening 112. In the configuration of FIGS. 7A and 7B, sidewall 104A defines an opening 104C (on FIG. 7B) through which a tubing line (e.g., which may be part of an infusion tubing circuit) can be installed in the compartment. Installing the tubing line in the second compartment 104 can position the tubing line to extend over opening 112 and the beta detector 58 positioned under the opening and/or extending upwardly through the opening. As a result, when radioactive eluate is supplied to and/or through the tubing line, the radioactive eluate may be positioned in and/or pass through the portion of the tubing line extending over opening 112. Beta detector 58 can detect beta emissions emanating from the radioactive eluate in the portion of the tubing positioned over opening 112, for example, while passing through base wall 104B via the opening.

When the second compartment 104 is intended to receive an infusion tubing circuit that includes one or more tubing lines arranged as discussed with respect to FIG. 6, the portion of the infusion tubing circuit positioned in the compartment may include a portion of radioisotope generator discharge line 75, a portion of waste line 76, second multi-way valve 74, and a portion of infusion tubing 70. To enable second multi-way valve 74 to be operatively connected to a control device (e.g., motor) through shielding assembly 28, second compartment 104 may also include a second opening 114 (e.g., as illustrated on FIG. 7B) formed through the base wall 104B. The second opening 114 may be sized and positioned to enable second multi-way valve 74 to be operatively connected to a control device positioned outside of the shielding assembly. During use, an operator may install a portion of an infusion tubing circuit through opening 104C into second compartment 104 such that sidewall 104A and base wall 104B collectively bound the portion of the inserted infusion tubing circuit with the material that provides a barrier to radioactive radiation. The second multi-way valve 74 can be operatively connected with the control device through second opening 114, and a portion of the infusion tubing circuit, such as radioisotope generator discharge line 75, can be positioned to extend over opening 112 to enable beta detector 58 to detect beta emissions through the opening and the portion of tubing positioned there over.

As noted above, shielding assembly 28 in the example of FIGS. 7A and 7B also includes a third compartment 106. Third compartment 106 may be defined by a sidewall 106A that forms an opening 106B. Third compartment 106 can be configured (e.g., sized and/or shaped) to receive gamma detector 60. In addition, the third compartment 106 may be configured to be placed in fluid communication with the infusion tubing 70, when the infusion tubing is installed in shielding assembly 28. During operation, such as a quality control procedure, radioactive eluate generated by radioisotope generator 52 positioned in first compartment 102 can flow through one or more tubing lines of the infusion tubing circuit to gamma detector 60 in third compartment 106. Radioactive eluate so delivered to the third compartment 106 can emit gamma emissions that can be detected by the gamma detector 60 in the compartment.

In some examples, third compartment 106 is configured (e.g., sized and/or shaped) to receive an eluate-receiving container through opening 106B. For example, after gamma detector 60 is installed in third compartment 106, the eluate-receiving container may be positioned in the compartment adjacent to and/or over the gamma detector. Infusion tubing line 70 can then be placed in fluid communication with the eluate-receiving container such that, when eluant is pumped through the radioisotope generator, eluate generated by the generator can flow towards the eluate-receiving container and partially or fully fill the container. Once suitably filled, a static (non-flowing) portion of radioactive eluate can be positioned in third compartment 106 along with gamma detector 60. The static portion of radioactive eluate can emit gamma emissions that can be detected by gamma detector 60, for example to determine an activity of one or more radioisotopes present in the radioactive eluate.

In some examples, including the example illustrated in FIGS. 7A and 7B, shielding assembly 28 includes one or more additional compartments besides first compartment 102, second compartment 104, and third compartment 106. For example, shielding assembly 28 may include fourth compartment 108 that is configured to receive and hold a waste container (e.g., waste container 54 from FIG. 6). Fourth compartment 108 may include a sidewall 108A and a base wall 108B. The sidewall 108A of the fourth compartment can extend vertically from the base wall 108B to define an opening 108C through which waste container 54 can be inserted into the compartment. The sidewall 108A and base wall 108B can collectively bound a space configured to receive and hold the waste container. When waste container 54 is installed in fourth compartment 108, waste line 76 may be placed in fluid communication with the waste container.

To enable the various tubing lines of the radioisotope generator system to extend from one compartment to an adjacent compartment, shielding assembly 28 may include additional tubing pathways and/or tubing compartments to facilitate routing of the tubing lines. In the example of FIGS. 7A and 7B, shielding assembly 28 includes a sidewall compartment 110. The sidewall compartment 110 in this example is defined by a recessed cavity formed in sidewall 108A of fourth compartment 108. In particular, in the illustrated arrangement, sidewall compartment 110 extends vertically (in the Z-direction indicated on FIG. 7B) along the exterior surface of sidewall 108A defining the fourth compartment 108 configured to receive waste container 54. Sidewall compartment 110 can be configured to receive one or more portions of tubing, such as at least a portion of infusion tubing 70 and at least a portion of waste line 76.

When installed, waste line 76 may extend from second multi-way valve 74 positioned over opening 114 in second compartment 104 through sidewall compartment 110 to fourth compartment 108. Similarly, infusion tubing 70 may extend from second multi-way valve 74 positioned over opening 114 in second compartment 104 through sidewall compartment 110 and subsequently out of the sidewall compartment. In different configurations, infusion tubing 70 may or may not exit shielding assembly 28 before returning to the shielding assembly by having an outlet of infusion tubing 70 positioned in third compartment 106, for example in fluid communication with an eluate-receiving container positioned in the third compartment.

Shielding assembly 28 may include additional tubing pathways formed in or through one or more sidewalls to find the compartments of the assembly in order to facilitate routing of tubing between adjacent compartments. For example, the sidewall 104A defining second compartment 104 may include an eluant tubing pathway 116 formed through the sidewall. As another example, the sidewall 102A defining first compartment 102 may include an eluate tubing pathway 118A and a generator discharge tubing pathway (which may also be referred to as an eluate tubing pathway) 118B. When so configured, eluant line 62 (FIG. 6) can enter shielding assembly 28 via eluant tubing pathway 116 and further extend from the second compartment 104 into the first compartment 102 via eluant tubing pathway 118A. Eluate line 62 can be connected with pump 40 on one end (e.g., outside of shielding assembly 28, in configurations where the pump is located outside of the shielding assembly) and with radioisotope generator 52 in first compartment 102 on an opposite end. Radioactive eluate produced via the generator can discharge via radioisotope generator discharge line 75 and can flow out of first compartment 102 via radioisotope generator discharge line 75 positioned in eluate tubing pathway 118B.

To secure eluant line 62 in eluant tubing pathway 118A and radioisotope generator discharge line 75 in eluate tubing pathway 118B, respectively, shielding assembly 28 may include a tube lock 120. Tube lock 120 may be a structure which is movable over eluant tubing pathway 118A and eluate tubing pathway 118B to secure or lock each tube in a respective pathway. This can prevent one or more of the tubes from inadvertently coming out of its respective pathway and being crushed when the door enclosing first compartment 102 or second compartment 104 is closed.

As briefly discussed above, when shielding assembly 28 is configured with multiple compartments, the compartments may be arranged relative to each other to help shield beta detector 58 and/or gamma detector 60 from radioactive emissions emanating from radioisotope generator 52 itself. This can allow one or both detectors to detect radioactive emissions associated with radioactive eluate generated by the generator rather than radioactive emissions associated with the generator itself. In applications where the radioisotope generator system includes both a beta detector and a gamma detector, the gamma detector may be more sensitive to background radiation from the radioisotope generator than the beta detector. That is, the gamma detector may be more prone to being saturated by being exposed to gamma emissions emanating from the radioisotope generator itself than the beta detector. For these and other reasons, the gamma detector may be positioned in such a way relative to the radioisotope generator so as to try and minimize exposure to gamma radiation from the radioisotope generator, for example, by maximizing an amount of shielding material positioned between the gamma detector and radioisotope generator.

In general, the amount of shielding material positioned between gamma detector 60 and radioisotope generator 52 may be increased by positioning one or more compartments of shielding assembly 28 between first compartment 102 and third compartment 106 rather than positioning the compartments directly adjacent to each other. In some examples, shielding assembly 28 is configured so that at least one compartment is positioned between first compartment 102 and third compartment 106 (e.g., along the length of the shielding assembly in the Y-direction indicated on FIGS. 7A and 7B and/or vertically in the Z-direction indicated on the figures). For example, second compartment 104 may be positioned between first compartment 102 that is configured to receive radioisotope generator 52 and third compartment 106 that is configured to house gamma detector 60. As a result, the sidewall 102A defining first compartment 102, the sidewall 104A defining the second compartment 104, and the sidewall 106A defining the third compartment, in each case formed of material that provides a barrier to radioactive radiation, can be located between the radioisotope generator 52 and gamma detector 60, when installed in shielding assembly 28. Thus, the amount of shielding material present between radioisotope generator 52 and gamma detector 60 may be the combined thicknesses of the sidewalls.

In configurations where shielding assembly 28 includes more than three compartments, such as illustrated in the example of FIGS. 7A and 7B, one or more of the other compartments may also be positioned between first compartment 102 and third compartment 106. In the illustrated example, fourth compartment 108 is also positioned between the first compartment 102 and third compartment 106. In this arrangement, both second compartment 104 and fourth compartment 108 (as well as sidewall compartment 110) are located between first compartment 102 and third compartment 106. As a result, the sidewall 102A defining first compartment 102, the sidewall 104A defining the second compartment 104, the sidewall 108A defining the fourth compartment 108, and the sidewall 106A defining the third compartment, in each case formed of material that provides a barrier to radioactive radiation, can be located between the radioisotope generator 52 and gamma detector 60, when installed in shielding assembly 28. Again, the amount of shielding material present between radioisotope generator 52 and gamma detector 60 may be the combined thicknesses of the sidewalls, providing increased shielding protection as opposed to if fewer sidewalls or a lesser thickness of sidewall material was located between the components.

Independent of whether shielding assembly 28 includes one or more compartments between first compartment 102 and third compartment 106, offsetting the location of gamma detector 60 in third compartment 106 relative to the location of radioisotope generator 52 in first compartment 102 (e.g., horizontally and/or vertically) may be useful to increase the amount of shielding material present between the gamma detector and radioisotope generator. Offsetting the two components relative to each other in three-dimensional space can increase the amount of shielding material positioned between the components, thereby increasing the amount of radiation blocked by the shielding material.

In practice, a radiation path may be defined from radioisotope generator 52 to gamma detector 60 when the components are installed in shielding assembly 28. The radiation path may be a linear path or route taken by that portion of the radioactive emissions (e.g., beta particles and/or gamma rays) emitted by the radioisotope generator that travel to the gamma detector (e.g., can be detected by the gamma detector if not otherwise blocked). The radiation path may be the shortest linear distance between radioisotope generator 52 and gamma detector 60 (e.g., the active surface of the gamma detector that detectors gamma rays). Depending on the configuration of the radioisotope generator system, the shortest linear distance may be from the top of radioisotope generator 52 to the top of gamma detector 60, which is configured to detect radioactive emissions emanating from radioactive eluate received in the third compartment 106.

The shielding material forming the one or more sidewalls 100 of shielding assembly 28 can block radiation along the radiation path from the radioisotope generator to the gamma detector, for example to prevent gamma detector 60 from detecting background radiation from radioisotope generator 52 above a desired level. This can be useful to help ensure that gamma detector 60 accurately measures the radioactivity of radioactive eluate generated by the generator and conveyed to third compartment 106 and does not erroneously measure radioactive active emissions emitted by the generator itself as being as being attributable to the radioactive eluate.

Figure 7C:
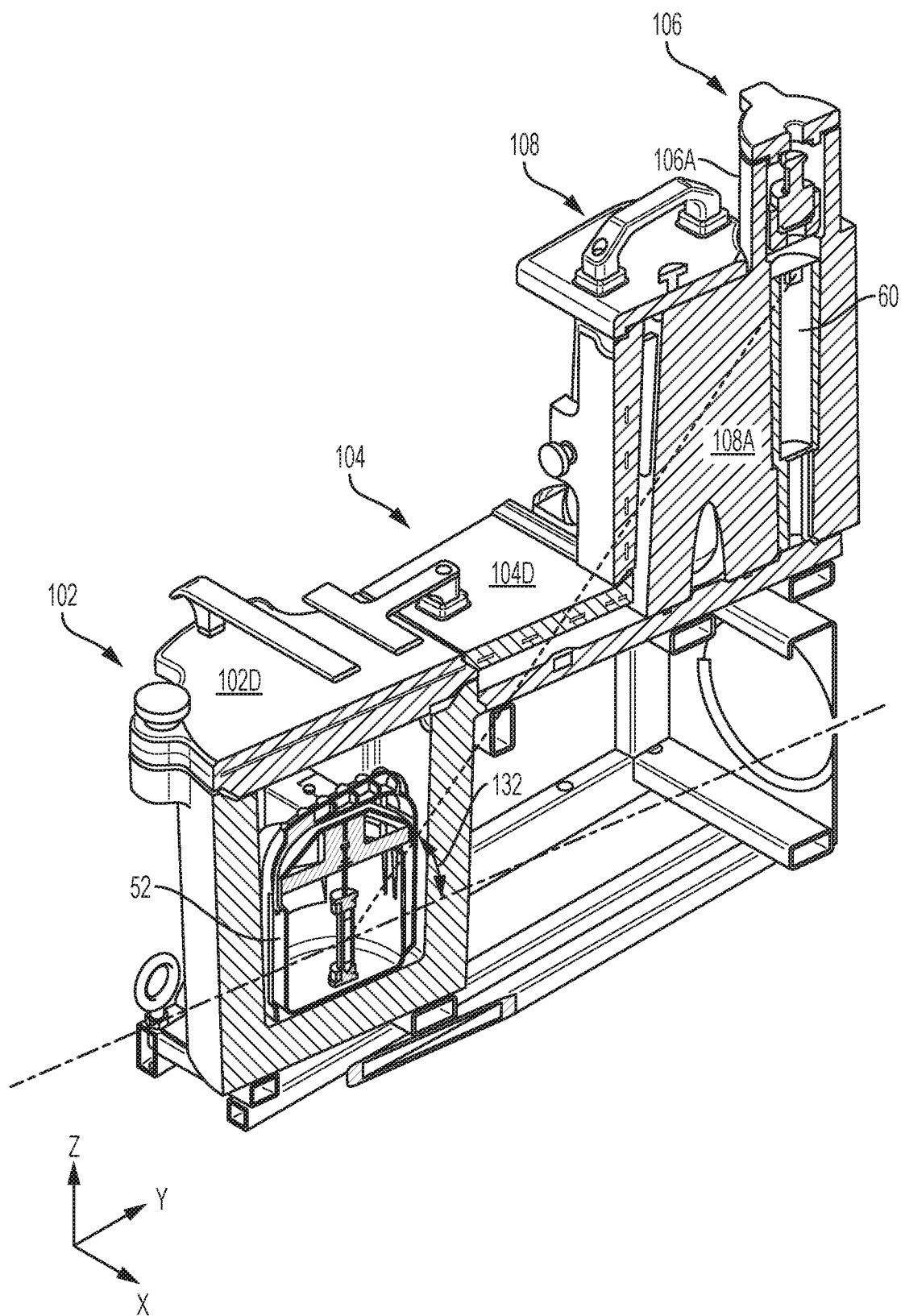
FIG. 7C is a perspective view of the example shielding assembly from FIGS. 7A and 7B shown sectionalized along the A-A sectional line indicated on FIG. 7A.
Figure 7D:
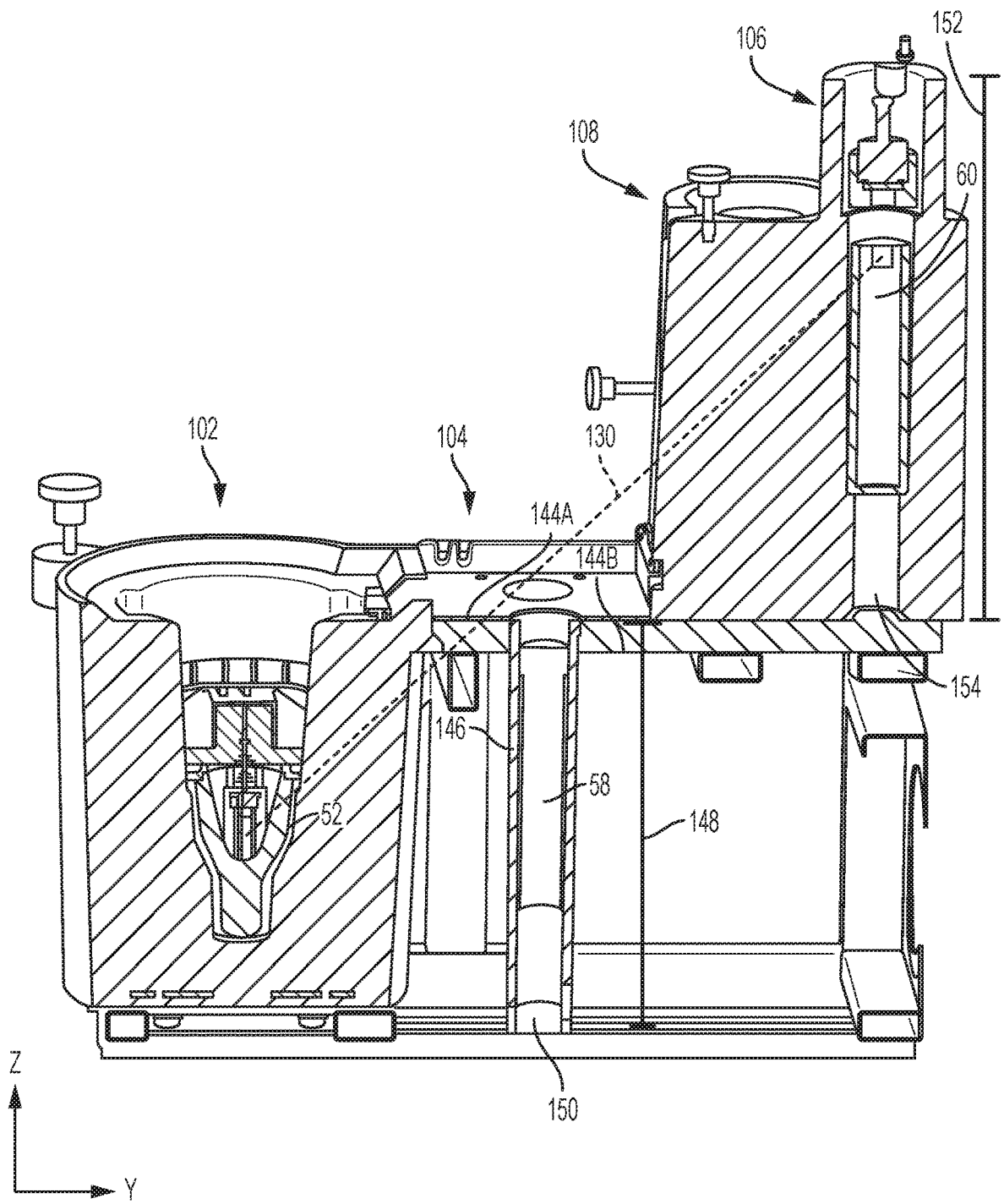
FIG. 7D is a side view of the example shielding assembly from FIGS. 7A and 7B shown sectionalized along the B-B sectional line indicated on FIG. 7A.

FIG. 7C is a perspective view of shielding assembly 28 from FIGS. 7A and 7B shown sectionalized along the A-A sectional line indicated on FIG. 7A, while FIG. 7D is a side view of shielding assembly 28 from FIGS. 7A and 7B shown sectionalized along the B-B sectional line indicated on FIG. 7A. FIG. 7D illustrates shielding assembly 28 without doors attached for purposes of illustration. As shown in this example, a radiation path 130 is defined from radioisotope generator 52 in first compartment 102 to gamma detector 60 in third compartment 106. Radiation path 130 passes through at least a portion of the first compartment 102 (e.g., sidewall 102A of the compartment) and at least a portion of third compartment 106 (e.g., sidewall 106A of the compartment). When shielding assembly 28 includes one or more other compartments positioned between first compartment 102 and third compartment 106, radiation path 130 may or may not also pass through portions of those one or more other compartments.

For example, in the illustrated configuration, radiation path 130 passes through first compartment 102, second compartment 104, and fourth compartment 108, before passing into the third compartment 106. Depending on the arrangement of the different compartments, radiation path 130 may pass through a side wall and/or base wall defining each compartment. In the example of FIGS. 7C and 7D, radiation path 130 extends from radioisotope generator 52 in first compartment 102 through sidewall 102A, through sidewall 104A which is shared and coextensive with sidewall 102A, through sidewall 108A, and finally through sidewall 106A before reaching the active surface of gamma detector 60 that detects gamma emissions. In effect, radiation path 130 defines an axis extending from and/or through radioisotope generator 52 and gamma detector 60 that transects (e.g., cuts across) the second compartment 104 and fourth compartment 108 between first compartment 102 and third compartment 106. Because gamma radiation emitted from radioisotope generator 52 needs to travel through each of these surfaces that provide a barrier to radioactive radiation before reaching gamma detector 60, the amount of gamma radiation reaching the detector is reduced as compared to if less shielding material were provided between the radioisotope generator and the gamma detector. In turn, this reduces the amount of background radiation, or amount of ambient radiation, that gamma detector 60 may detect even when radioactive eluate is not supplied to third compartment 106.

In some examples, third compartment 106 and/or gamma detector 60 located in the compartment is positioned at a different elevation with respect to ground than first compartment 102 and/or radioisotope generator 52 positioned in the compartment. This may increase the amount of shielding material positioned along radiation path 130, for example, by extending the length of the path as opposed to if the gamma detector 60 is at the same elevation as radioisotope generator 52. By positioning third compartment 106 and/or gamma detector 60 at a different elevation relative to first compartment 102 and/or radioisotope generator 52, the length of radiation path 130 can be increased without needing to increase the overall footprint of the radioisotope generator system, as may otherwise be needed to increase the length of the radiation path without changing elevation.

In different examples, third compartment 106 and/or gamma detector 60 may be located at a higher elevation or a lower elevation with respect to ground relative to first compartment 102 and/or radioisotope generator 52. In the illustrated example, third compartment 106 and gamma detector 60 contained therein are both positioned at a higher elevation with respect to ground than first compartment 102 and radioisotope generator 52 contained therein. Positioning third compartment 106 at a higher elevation than the first compartment 102 may be useful to provide an ergonomically efficient arrangement. In practice, radioisotope generator 52 may be a comparatively heavy component that is replaced on a comparatively infrequent basis. Positioning radioisotope generator 52 close to ground can be helpful so the operator does not need to lift radioisotope generator 52 to a high height when replacing it. By contrast, an eluate-receiving container positioned in third compartment 106 may be replaced on a comparatively frequent basis, such as once per day. Further, the eluate-receiving container may be a comparatively light component that is easily lifted. Accordingly, positioning third compartment 106 at a higher elevation than first compartment 102 can be helpful, for example so that an operator does not need to bend over or bend over too far to replace the eluate-receiving container. In addition, positioning first compartment 102 at a lower elevation than third compartment 106 may lower the center of gravity of system 10, making the system more stable.

In some examples, radiation path 130 extends at a non-zero degree angle 132 with respect to ground to position radioisotope generator 52 and gamma detector 60 at different elevations. While angle 132 may vary, in some examples, the angle ranges from 30° to 75° with respect to ground. In other examples, the angle ranges from 30° to 40°, from 40° to 45°, from 45° to 50°, from 50° to 60°, or from 60° to 75°. In one particular example, the angle ranges from 43° to 47°. The angle may be positive if gamma detector 60 is at a higher elevation than radioisotope generator 52 or may be negative if gamma detector 60 is at a lower elevation the radioisotope generator 52.

When the third compartment 106 is positioned at a higher elevation with respect to ground than first compartment 102, the top surface of the opening 106C of the third compartment (e.g., rim of the compartment) may be higher than the top surface of the opening 102C of the first compartment (e.g., rim of the compartment). In some examples, the opening of the third compartment is at least 10 centimeters higher than the opening of the first compartment, such as at least 25 centimeters higher or at least 30 centimeters higher. For example, the opening of the third compartment may range from 10 centimeters to 100 centimeters higher than the opening of the first compartment, such as from 20 centimeters to 50 centimeters. Additionally or alternatively, the opening of the third compartment may be spaced horizontally (e.g., in the X and/or Y-direction indicated on FIG. 7C) from the opening of the first compartment, for example to increase the separation distance between the compartments and the amount of shielding material positioned there between. For example, the opening 106C of the third compartment may be spaced at least 20 centimeters from the opening of the first compartment, such as at least 35 centimeters. In some examples, the opening 106C of the third compartment is spaced from 20 centimeters to 50 centimeters from the opening of the first compartment. In each case, the horizontal distance between the openings of the compartments can be measured from the center of one compartment to the center of the other compartment.

Independent of the specific way in which first compartment 102 and radioisotope generator 52 contained therein are arranged relative to third compartment 106 and gamma detector 60 contained therein, shielding assembly 28 may provide a sufficient amount of radiation shielding material between the radioisotope generator and gamma detector. The amount of shielding material present between radioisotope generator 52 and gamma detector 60 may be effective to ensure that background radiation in the third compartment caused by the radioisotope generator is sufficiently low for the gamma detector to detect a desired level of radiation emitted by radioactive eluate in the third compartment, for example when the radioactive eluate is supplied to an eluate-receiving container in the compartment. In some examples, the desired level of radiation is less than 0.6 microcuries of Sr-82. For example, the desired level of radiation may be less than 0.5 microcuries of Sr-82, less than 0.4 microcuries of Sr-82, less than 0.3 microcuries of Sr-82, less than 0.2 microcuries of Sr-82, or less than 0.1 microcuries of Sr-82. In yet other applications, the desired level of radiation is less than 0.05 microcuries of Sr-82, less than 0.02 microcuries of Sr-82, or less than 0.01 microcuries of Sr-82. Since the activity of radioactive eluate in the eluate-receiving container (e.g., after decay of an initially-present short-lived radioisotope such as Rb-82) may be expected to be less than this level of radiation, gamma detector 60 may beneficially detect radiation levels below this level without interference of background radiation. While the total amount of radiation shielding material positioned along radiation path 130 may vary, in some examples, shielding assembly 28 has at least 20 centimeters of shielding material positioned on the pathway (e.g., such that the radiation path needs to travel through this length of material before reaching gamma detector 60), such as at least 30 centimeters of shielding material. For example, shielding assembly 28 may be configured to provide from 20 centimeters to 50 centimeters of shielding material on the pathway, such as from 30 centimeters to 40 centimeters of shielding material.

To increase the amount of shielding material located along radiation path 130, the compartments may be arranged so the radiation path crosses preferentially through sidewalls defining the compartments rather than the void space of the compartments themselves. That is, instead of configuring the compartments so that radiation path 130 passes preferentially through the open areas of the compartments, the compartments may be arranged relative to each other so that the radiation path passes through sidewall sections of the compartments.

Figure 7E:
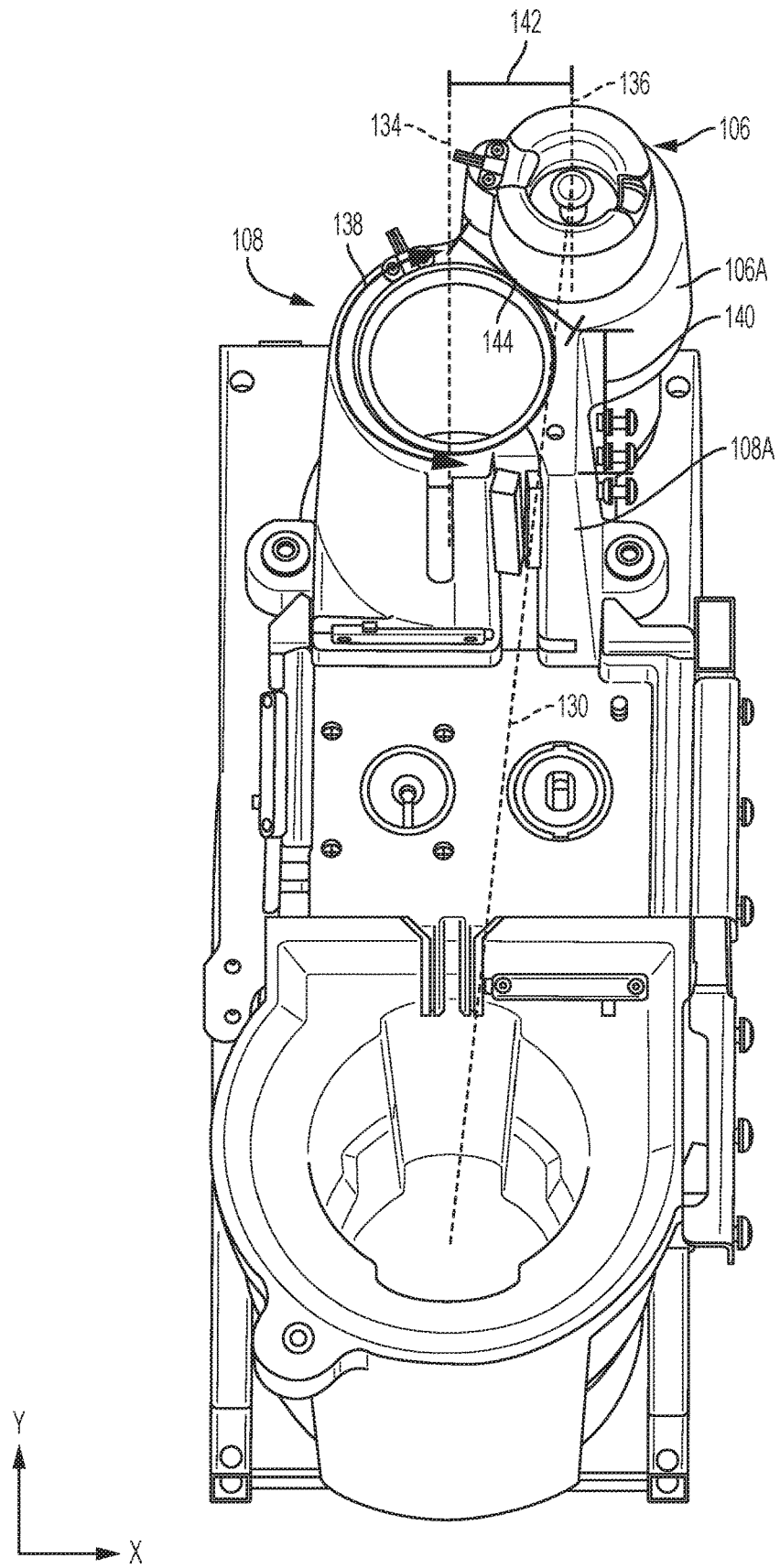
FIG. 7E is a top view of the example shielding assembly from FIGS. 7A and 7B illustrating an example arrangement of compartments in which a radiation path passes through one or more sidewall sections defining the compartments.

FIG. 7E is a top view of shielding assembly 28 from FIGS. 7A and 7B (shown with doors removed) illustrating an example arrangement of compartments in which radiation path 130 passes through one or more sidewall sections defining the compartments. For example, in the illustrated configuration, fourth compartment 108 is a laterally offset (in the X-direction indicated on FIG. 7E) from radiation path 130 such that the radiation path travels through sidewall 108A instead of the void space in the center of the compartment. This can help maximize radiation shielding provided by the fourth compartment, as compared to if the fourth compartment 108 is centered about it the radiation path. Since radiation path 130 may be dictated by the position of a gamma detector 60 and radioisotope generator 52, fourth compartment 108 can be laterally offset from the radiation path by controlling the position of third compartment 106 (which contains gamma detector 60) and first compartment 102 (which contains radioisotope generator 52) relative to the fourth compartment.

In some examples, third compartment 106 is arranged relative to fourth compartment 108 such that an axis 134 bisecting fourth compartment 108 (e.g., that is parallel to the length of shielding assembly 28 in the Y-direction indicated on FIG. 7E) is offset from an axis 136 bisecting third compartment 106 (e.g., that is also parallel to the length of shielding assembly 28). Each axis may bisect a respective compartment by dividing the compartment into two equally sized halves. The axis 136 bisecting third compartment 106 may be offset relative to the fourth compartment 108 such that the axis is co-linear with a section of sidewall 108A of the fourth compartment. In the illustrated configuration, fourth compartment 108 includes a section of sidewall 138 that is arcuate shaped and a section of sidewall 140 that is planar or linear. The arcuate section of sidewall 138 and the linear section of sidewall 140 may be contiguous with each other and, in combination, form sidewall 108A. With this arrangement, the linear section of sidewall 140 is coaxial with axis 136 that bisects third compartment 106. As a result, radiation emissions traveling along radiation path 130 in the illustrated configuration must travel through substantially the entire length of the linear section of sidewall 140 before reaching gamma detector 60, which may increase the likelihood of the radiation being blocked before reaching the gamma detector.

In some examples, the compartments of shielding assembly 28 are arranged relative to each other such that radiation path 130 travels through a greater length of shielding material than void space (e.g., for some or all of the compartments). For example, in FIG. 7E the compartments are arranged so that radiation path 130 travels through a length of shielding material defining sidewall 108A (e.g., linear section of sidewall 140) that is greater than a length the radiation path travels through the void space or cavity formed by sidewall 108A. As illustrated, radiation path 130 does not travel through any length of void space defining fourth compartment 108. However, if third compartment 106 were moved so that axis 136 is closer to axis 134, the radiation path may cross through a portion of the void space defining the compartment. In this regard, while arranging third compartment 106 and/or fourth compartment 108 relative to each other to align radiation path 130 with one or more sidewall sections can be helpful to increase the amount of radiation shielding, it should be appreciated that the shielding assembly in accordance with the disclosure is not limited to this example arrangement of components. In other configurations, for example, third compartment 106 and fourth compartment 108 may be aligned so that axis 134 is coaxial with axis 136.

In configurations where the third compartment 106 and fourth compartment 108 are offset from each other, the axis 134 bisecting the fourth compartment may be offset from the axis 136 bisecting the third compartment by a distance 142. For example, the compartments may be offset relative to each other by a distance of at least 2 centimeters, such as at least 4 centimeters, a distance ranging from 2 centimeters to 10 centimeters, or a distance ranging from 4 centimeters to 6 centimeters. When the third compartment 106 and fourth compartment 108 are offset relative to each other, radiation path 130 may pass through an offset side of the fourth compartment rather than directly through the center of the compartment. That is, radiation path 130 may not bisect the bisect the compartment which may cause the radiation path to cross the largest void space of the compartment but may instead be offset preferentially to one side of the compartment or the other side of the compartment relative to the bisecting axis. In some examples, fourth compartment is offset relative to radiation path 130 such that the radiation path passes through less than 10 centimeters devoid of shielding material inside of the container, such as less than 5 centimeters devoid of shielding material. Where radiation path 130 crosses the void space of fourth compartment 108 between side wall surfaces, the length of the chord formed between where the radiation path intersects the two sidewall surfaces can be considered the length through which the radiation path passes that is devoid of shielding material.

While the third compartment 106 and fourth compartment 108 can have different positions and configurations as described herein, in the illustrated example of FIG. 7E, third compartment 106 is positioned laterally offset of and directly adjacent to fourth compartment 108. In this example, third compartment 106 and fourth compartment 108 share an adjoining section of sidewall 144. In some examples, one or more (e.g., all) of the compartments of shielding assembly 28 are formed is physically separate structures that are then join together to form a unitary shielding assembly. For example, third compartment 106 and fourth compartment 108 may be fabricated (e.g., cast, machined, molded) as separate structures and then placed in direct contact with each other to form shared sidewall 144. In other examples, one or more (e.g., all) of the compartments of shielding assembly 28 are formed together to provide a permanent and physically joined structure. For example, third compartment 106 and fourth compartment 108 may be fabricated together as a permanently joined structure.

While first compartment 102, third compartment 106, and fourth compartment 108 are illustrated as defining a substantially circular-shaped compartment and second compartment 104 is illustrated as defining a substantially rectangular-shaped compartment, the compartments can define other shapes. In general, each compartment can define any polygonal (e.g., square, hexagonal) or arcuate (e.g., circular, elliptical) shape, or even combinations of polygonal and arcuate shapes. Accordingly, while each compartment of shielding assembly 28 is described herein as being defined by a sidewall, it should be appreciated that the sidewall may be a single contiguous sidewall or may have multiple individual sidewall sections which, collectively, define the sidewall. The specific shape of each compartment may vary based on the size and shape of the component of components intended to be inserted into the compartment.

With further reference to FIG. 7D, base wall 104B of second compartment 104 may define a top surface 144A and a bottom surface 144B opposite the top surface. When beta detector 58 is positioned below top surface 144A (and optionally below bottom surface 144B), second compartment 104 may include an extension portion 146 extending downwardly from the base wall 102B to protect beta detector 58 along its length. Extension portion 146 can be configured (e.g., sized and/or shaped) to receive beta detector 58. Extension portion 146 may have a height 148 (e.g., in the Z-direction indicated on FIG. 7D) greater than the length of beta detector 58. In some examples, extension portion 146 has a height 148 greater than or equal to the height of first compartment 102, e.g., such that the extension portion extends downwardly to the same position or below that to which first compartment 102 extends.

To facilitate installation and removal of beta detector 58 as well as electrical communication between the beta detector and a controller that controls the infusion system (e.g., via wiring), an opening may be formed in extension portion 146. In some examples, the bottom end 150 of extension portion 146 is open or devoid of material. When so configured, beta detector 58 may be inserted into and removed from the extension portion via the open bottom end. Additionally, electrical communication between beta detector 58 and a controller communicatively coupled to the beta detector may be provided via one or more cables that extend from the controller to the beta detector through the open bottom end of extension portion 146.

With continued reference to FIG. 7D, third compartment 106 may have a height 152 (e.g., in the Z-direction indicated on FIG. 7D) greater than the length of beta detector 58. In some examples, third compartment 106 has a height 152 greater than or equal to the height of fourth compartment 108. In some examples, third compartment 106 extends from a location that is coplanar with base wall 104B of second compartment 104 vertically upwardly. For example, third compartment 106 may extend vertically upwardly to an elevation equal to or higher than the opening of fourth compartment 108. In other configurations, third compartment 106 may extend below a location that is coplanar with base wall 104B.

Independent of the specific height of third compartment 106, the compartment may have an opening to facilitate installation and removal of gamma detector 60. The opening may also provide access for electrical communication between the gamma detector and a controller that controls the infusion system (e.g., wiring). In some examples, the bottom and 154 of third compartment 106 is open or devoid of material. When so configured, gamma detector 60 may be inserted into and removed from third compartment 106 via the open bottom end.

In other configurations, third compartment 106 may have an opening in sidewall 106A through which gamma detector 60 can be inserted and removed. In these configurations, third compartment 106 may include a side pocket or cavity to receive a gamma detector. In yet other configurations, gamma detector 60 may be inserted through the open top end of third compartment 106 rather than through a separate access port. When gamma detector 60 includes open bottom and 154, however electrical communication between gamma detector 60 and a controller communicatively coupled to the gamma detector may be provided via one or more cables that extend from the controller to the gamma detector through the open bottom and of third compartment 106.

The specific dimensions of the compartments of shielding assembly 28 may vary, for example, based on the size and configuration of components used in the system. In some examples, the thickness of sidewall 102A ranges from 35 millimeters to 100 millimeters, the thickness of sidewall 104A ranges from 80 millimeters to 140 millimeters, and the combined thickness of sidewall 106A and sidewall 108A ranges from 125 millimeters to 175 millimeters. The foregoing dimensions are provided for purposes of illustration, and it should be appreciated that the shielding assembly in accordance with the disclosure is not necessarily limited in this respect.

To enclose the openings defined by the compartments of shielding assembly 28, each compartment may have a corresponding door. Each door may be opened by an operator to insert and/or remove components and closed to provide an enclosed barrier to radioactive radiation and components contained therein. Each door may be formed of the same or of different material used to form the least one sidewall 100 of shielding assembly 28 and may provide a barrier to radioactive radiation. With reference to FIG. 7A, each compartment of shielding assembly 28 is illustrated as including a door.

Specifically, in the illustrated configuration, first compartment 102 is enclosed by a door 102D, second compartment 104 is enclosed by a door 104D, third compartment 106 is enclosed by a door 106D, fourth compartment 108 is enclosed by a door 108D, and sidewall compartment 110 is enclosed by a sidewall door 110D. Each door can be selectively opened to provide access to the respective compartment enclosed by the door. Each door can further be selectively closed to cover the opening providing access to the respective compartment with radiation shielding material.

In the example of FIG. 7A, first compartment 102, second compartment 104, third compartment 106, and fourth compartment 108 each define an opening that is oriented upwards with respect to gravity (e.g., defines an opening in the X-Y plane that can be accessed in the Z-direction indicated on the figure). In such an example, first door 102D second door 104D, third door 106D, and fourth door 108D may each open upwardly with respect to gravity to access a corresponding compartment enclosed by the door. This can allow an operator to insert and remove components from a respective one of the compartments by moving the door upwardly or downwardly in the vertical direction. In other configurations, however, the opening defined by one or more of the compartments may not open upwardly with respect to gravity. For example, one or more (e.g., all) of the compartments may have a permanently enclosed top surface formed of radiation shielding material and may define an opening through a sidewall forming the compartment. In these examples, a door used to provide selective access to the opening formed in the sidewall may open laterally rather than upwardly with respect to gravity. Other opening arrangements and door configurations for shielding assembly 28 can also be used in a shielding assembly in accordance with the disclosure, and the disclosure is not necessarily limited in this respect.

In some examples, one or more of the doors of shielding assembly 28 may include interlocks or overlapping door segments to prevent one or more of the doors from inadvertently being opened. For example, one door may have a portion that overlaps an adjacent door, preventing the adjacent door from being opened before the door providing the overlapping portion is first opened. As one example arrangement, sidewall door 110D may overlap second door 104D which, in turn may overlap first door 102D. As a result, second door 104D cannot be opened in such a configuration before sidewall door 110D is opened. Similarly, first door 102D cannot be opened in such a configuration before second door 104D is opened. In some configurations, fourth door 108D also overlaps sidewall door 110D such that the sidewall door cannot be opened before the fourth door is opened. In general, arranging one or more doors to overlap with each other can be useful to help prevent inadvertent opening of one or more of the compartments of shielding assembly 28. For example, first compartment 102 may contain the greatest source of radioactive radiation when the radioisotope generator 52 is installed in the compartment. For this reason, shielding assembly 28 may be arranged so at least door 102D is overlapped by adjacent door, helping to prevent an operator from inadvertently opening the compartment containing the largest source of radiation.

The third compartment 106 containing the gamma detector 60 and/or an eluate-receiving container 56 may also include a door 106D. Door 106D can be opened to install eluate-receiving container 56 over gamma detector 60 and closed to enclose the eluate-receiving container in the compartment for receiving radioactive eluate from the radioisotope generator. To place the eluate-receiving container positioned in third compartment 106 in fluid communication with the radioisotope generator, an infusion tubing line may extend into the compartment and be in fluid communication with the eluate-receiving container. In some examples, sidewall 106A of the third compartment 106 has an opening or channel formed therein through which infusion tubing 70 passes to place eluate-receiving container 56 in fluid communication with the radioisotope generator. In other examples, door 106D may include an opening through which infusion tubing 70 can pass and be coupled to the eluate-receiving container.

In the example of FIG. 7A, third door 106D includes an opening 158 that is configured (e.g., sized and/or shaped) to receive infusion tubing 70. When assembled, infusion tubing 70 can extend out of shielding assembly 28 (e.g., through an opening in the sidewall of the fourth compartment 108 or sidewall compartment 110) and then reenter the shielding assembly through opening 158. A distal or terminal end of infusion tubing 70 may project into the third compartment 106 through opening 158 in door 106D and be in fluid communication with eluate-receiving container 56 contained therein.

Figure 7F:
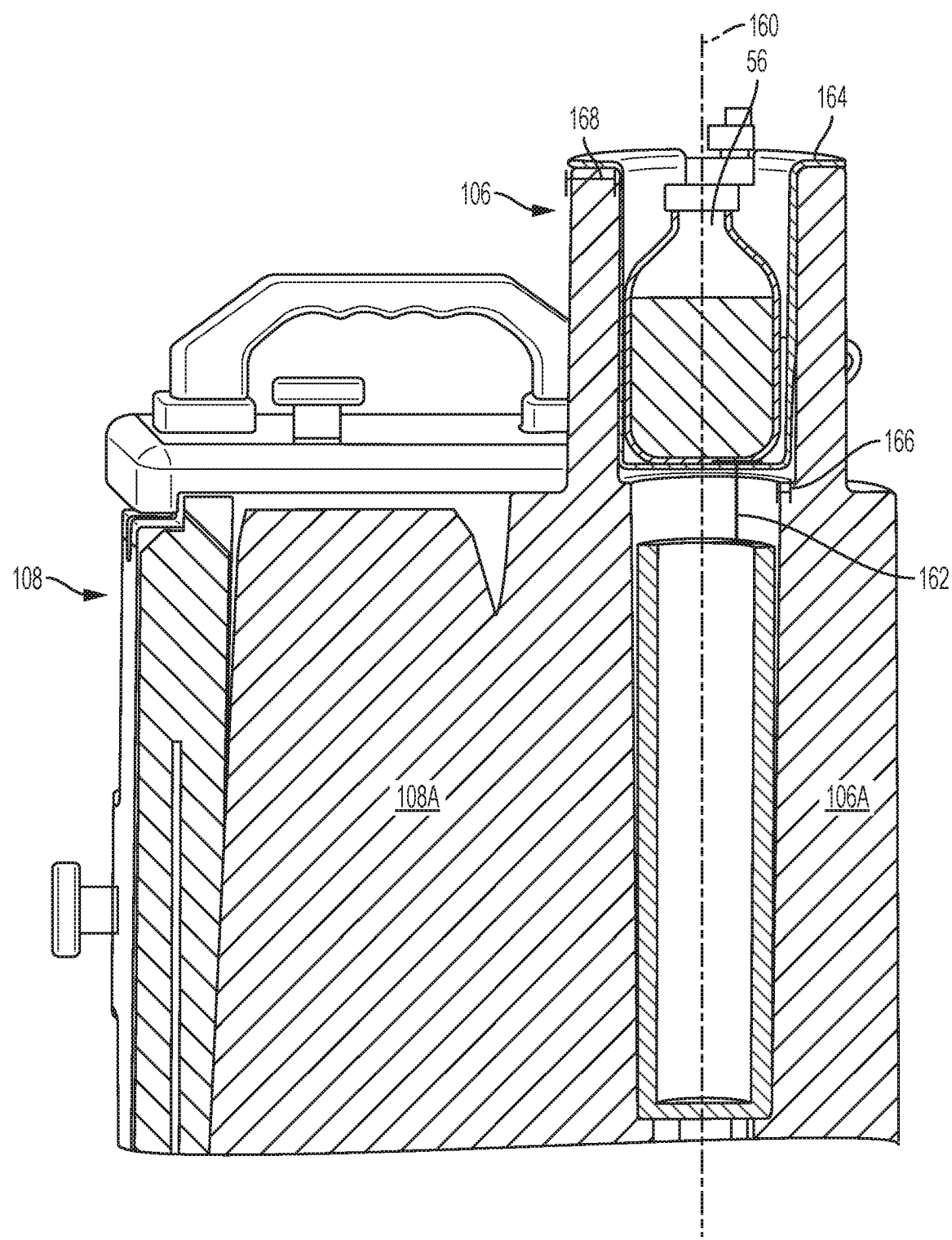
FIG. 7F is exploded view of a portion of the example shielding assembly from FIG. 7D showing an example arrangement of an eluate-receiving container relative to a gamma detector.

Eluate-receiving container 56 can have a variety of different configurations and be arranged in a number of different ways relative to gamma detector 60 in third compartment 106. FIG. 7F is an exploded view of a portion of shielding assembly 28 from FIG. 7D showing an example arrangement of eluate-receiving container 56 to gamma detector 60. As shown in this example, eluate-receiving container 56 is positioned in third compartment 106 at a location that is vertically above the gamma detector 60 (e.g., in the Z-direction indicated on FIG. 7E). In particular, in the illustrated arrangement, eluate-receiving container 56 and gamma detector 60 are arranged coaxially along their lengths about axis 160.

In general, ensuring that eluate-receiving container 56 is appropriately and repeatably positionable relative to gamma detector 60 can help ensure that gamma emissions measured by gamma detector 60 are accurate and appropriately calibrated. If eluate-receiving container 56 is positioned too close to gamma detector 60, small changes in the separation distance between the two components (e.g., as eluate-receiving container 56 is removed and reinserted into third compartment 106) can lead to measurement inconsistencies by the gamma detector. By contrast, if eluate-receiving container 56 is positioned too far away from gamma detector 60, it may be challenging for the gamma detector to accurately detect low level gamma emissions.

In some examples, eluate-receiving container 56 is received in third compartment 106 such that a bottom-most surface of the container is spaced a distance from the top of gamma detector 60. For example, a bottom-most surface of eluate-receiving container 56 may be positioned a distance 162 from gamma detector. The separation distance 162 may range from 5 millimeters to 100 millimeters, such as from 8 millimeters to 65 millimeters, or from 10 millimeters to 30 millimeters. In some examples, the separation distance 162 is defined relative to the overall length of eluate-receiving container 56. For example, the separation distance 162 may range from 0.1 to 1.5 times the overall length of eluate-receiving container 56, such as from 0.2 to 0.5 times the overall length of the eluate-receiving container. For instance, in the example where eluate-receiving container 56 has a length of approximately 80 millimeters and the separation distance is 0.25 times the overall length of the container, separation distance 162 can be approximately 20 millimeters.

In some examples, eluate-receiving container 56 is positionable inside of third compartment 106 without having an intermediate structure positioned between the container and gamma detector 60. Third compartment 106 may have an interior ridge, rim, or other support structure on which eluate-receiving container 56 can be positioned or otherwise supported to hold the container in the compartment above the gamma detector 60. In other examples, an insert 164 may be positioned in third compartment 106 between eluate-receiving container 56 and gamma detector 60. The insert 164 may serve different functions, such as a liquid collection barrier for radioactive eluate inadvertently spilled out of eluate-receiving container 56 and/or a positioning structure to position eluate-receiving container 56 in compartment 106 at a controlled location relative to gamma detector 60.

When used, insert 164 may be permanently mounted in third compartment 106 or may be insertable into and removable from the compartment. For example, insert 164 may be a structure that has a closed bottom end and is removable from third compartment 106 (via the open top end of the compartment). Insert 164 can collect radioactive eluate (or its decay product) that is inadvertently spilled and prevent the liquid from falling on gamma detector 60.

To retain insert 164 in third compartment 106, sidewall 106A may have an inwardly extending support means (a support means that extends towards a center of the compartment). In different examples, the support means may be a shoulder, a ridge, and/or a different inwardly protruding element. In the illustrated example, sidewall 106A has an inwardly extending ridge 166 on which a bottom surface of insert 164 may rest (or, in instances where insert 164 is not used, a bottom of eluate-receiving container 56 may rest). Additionally or alternatively, insert 164 may have a collar 168 extending outwardly from its body that is configured to rest on the rim defining the opening of third compartment 106. Independent of the specific features utilized to retain insert 164 in third compartment 106, the insert may hold the eluate-receiving container 56, when the inserted therein, at a fixed position and orientation with respect to gamma detector 60. This can help ensure repeatable measurements using gamma detector 60.

As discussed above with respect to FIG. 6, system 10 can be used to generate radioactive eluate that is infused (injected) into a patient, e.g., during a diagnostic imaging procedure. In practice, system 10 may operate in multiple modes of operation, one of which is a patient infusion mode. System 10 may deliver radioactive eluate to a patient during the patient infusion mode. System 10 may also generate radioactive eluate in one or more other modes in which the eluate is not delivered to a patient, e.g., to help ensure the safety, quality, and/or accuracy of radioactive eluate supplied during a subsequent patient infusion.

As one example, system 10 may be subject to periodic quality control (QC) checks where the system is operated without having infusion tubing 70 connected to a patient line 72. During a quality control mode of operation, radioactive eluate produced by system 10 may be analyzed to determine the radioactivity of one or more species of radioisotopes present in the radioactive eluate. If the activity level of one or more radioisotopes exceeds a predetermined/threshold limit, system 10 may be taken out of service to prevent a subsequent patient infusion procedure until the activity level of one or more radioisotopes in the radioactive eluate produced using the system are back within allowable limits.

For example, when the radioisotope generator 52 is implemented as a strontium-rubidium radioisotope generator, radioactive eluate produced using the generator may be evaluated to determine if radioactive strontium is releasing from the generator as eluant flows across and/or through the generator. Since strontium has a longer half-life than Rb-82, the amount of strontium infused into a patient with radioactive eluate is typically minimized. The process of determining the amount of strontium present in the radioactive eluate may be referred to as breakthrough testing since it may measure the extent to which strontium is breaking through into the radioactive eluate.

As another example, system 10 may be subject to periodic constancy checks in which the system is again operated without having infusion tubing 70 connected to patient line 72. During a constancy evaluation mode of operation, activity measurements made using beta detector 58 may be evaluated, e.g., cross checked, to determine whether the system is producing accurate and precise measurements. If activity measurements made using beta detector 58 deviate from measurements made using a validating apparatus, e.g., by more than a predetermined/threshold amount, the system be recalibrated to help ensure efficacious and accurate operation of system 10.

Figure 8:
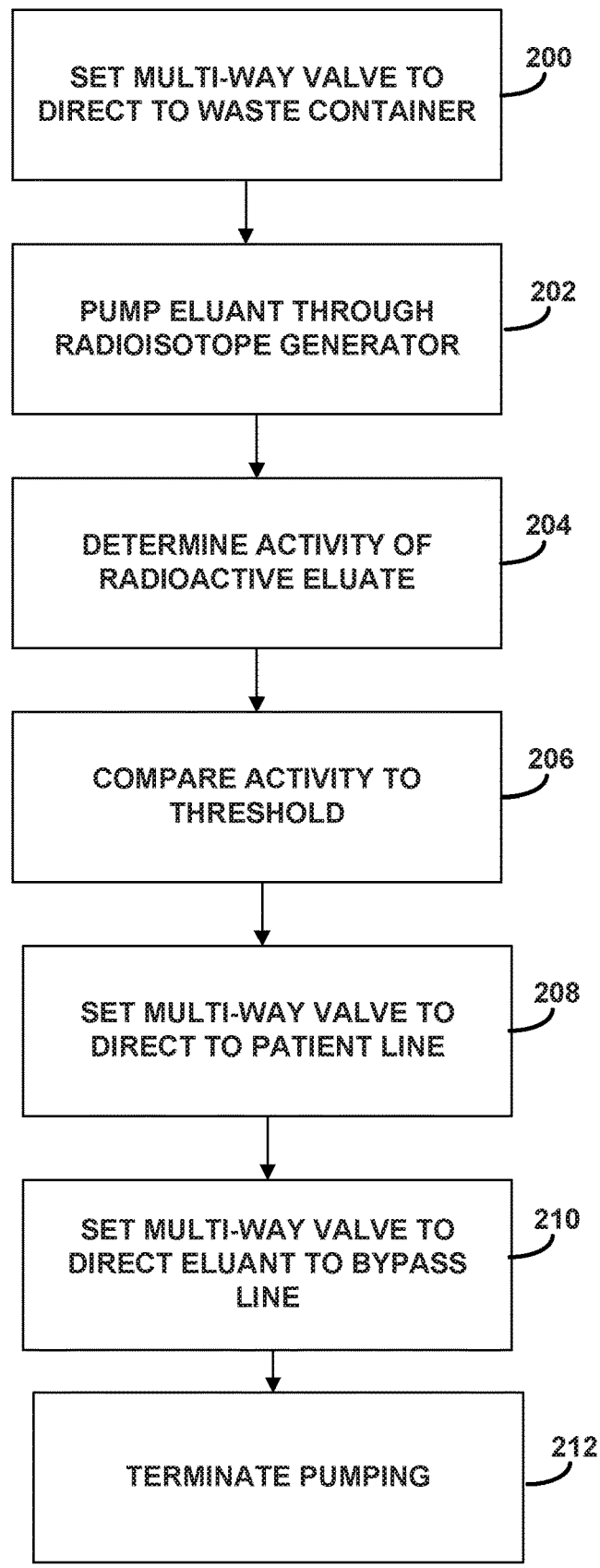
FIG. 8 is a flow diagram of an example technique that may be used to perform a patient infusion procedure to infuse radioactive liquid into a patient.

FIG. 8 is a flow diagram of an example technique that may be used to perform a patient infusion procedure to infuse radioactive liquid into a patient, e.g., during a diagnostic imaging procedure. For example, the technique of FIG. 8 may be used by system 10 to generate radioactive eluate and infuse the radioactive eluate into a patient. The technique of FIG. 8 will be described with respect to system 10, and more particularly the arrangement of exemplary components described with respect to FIG. 6 above, for purposes of illustration. However, it should be appreciated that the technique may be performed by systems having other arrangements of components and configurations, as described herein.

To initiate a patient infusion procedure, an operator may interact with system 10 to set the parameters of the infusion and to initiate the infusion procedure. System 10 may receive parameters for the infusion via user interface 16, via a remote computing device communicatively coupled to system 10, or through yet other communication interfaces. Example parameters that may be set include, but are not limited to, the total activity to be dosed to a patient, the flow rate of radioactive eluate to be dosed to the patient, and/or the volume of radioactive eluate to be dosed to the patient. Once the appropriate parameters establishing the characteristics of the infusion procedure are programmed and stored, system 10 may begin generating radioactive eluate that is infused into the patient.

As shown in the example of FIG. 8, a patient infusion procedure may start by controlling second multi-way valve 74 to place radioisotope generator discharge line 75 in fluid communication with waste container 54 via waste line 76 (200). If second multi-way valve 74 is initially positioned so radioisotope generator discharge line 75 is in fluid communication with waste container 54, controller 80 may control system 10 to proceed with the infusion procedure without first actuating the valve. However, if second multi-way valve 74 is positioned so radioisotope generator discharge line 75 is in fluid communication with infusion tubing 70, controller 80 may control second multi-way valve 74 (e.g., by controlling an actuator associated with the valve) to place the radioisotope generator discharge line in fluid communication with the waste container. In some examples, controller 80 receives a signal from a sensor or switch associated with second multi-way valve 74 indicating the position of the valve and, correspondingly, which line radioisotope generator discharge line 75 is in fluid communication with through the valve.

In addition to or in lieu of controlling second multi-way valve 74, controller 80 may check the position of first multi-way valve 64 and/or control the valve to change the position of the valve before proceeding with the patient infusion procedure. For example, if first multi-way valve 64 is positioned to direct eluant through bypass line 68, controller 80 may control the valve (e.g., by controlling an actuator attached to the valve) to place eluant line 62 in fluid communication with the radioisotope generator inlet line 66. In some examples, controller receives a signal from a sensor or switch associated with first multi-way valve 64 indicating the position of the valve and, correspondingly, which line eluant line 62 is in fluid communication with the valve.

With first multi-way valve 64 positioned to direct eluant through radioisotope generator inlet line 66 and second multi-way valve 74 positioned to direct radioactive eluate from radioisotope generator discharge line 75 to waste container 54, controller 80 can control pump 40 to pump eluant from eluant reservoir 50. Under the operation of controller 80, pump 40 can pump eluant from eluant reservoir 50 through radioisotope generator 52, and thereby generate the radioactive eluate via elution through the generator. In different examples, pump 40 may pump eluate at a constant flow rate or a flowrate that varies over time. In some examples, pump 40 pumps eluant at a rate ranging from 10 milliliters/minute to 100 mL/minute, such as a rate ranging from 25 mL/minute to 75 mL/minute. Radioactive eluate generated typically flows at the same rate as the rate at which pump 40 pumps eluant.

As eluant flows through radioisotope generator 52, a radioactive decay product of a parents radioisotope bound in the generator may release and enter the flowing eluant, thereby generating the radioactive eluate. The type of eluant used may be selected based on the characteristics of the parent radioisotope and support material used for radioisotope generator 52. Example eluants that may be used include aqueous-based liquids such as saline (e.g., 0.1-1 M NaCl). For example, in the case of a strontium-rubidium radioisotope generator, a Normal (isotonic) saline may be used as an eluant to elute Rb-82 that has decayed from Sr-82 bound on a support material.

Radioactive eluate generated by radioisotope generator 52 can be conveyed to beta detector 58, allowing the radioactivity level (also referred to as activity) of the eluate to be determined based on measurements made by the beta detector (204). In some configurations, radioactive eluate is supplied to tubing or a reservoir positioned proximate to beta detector 58, allowing the beta detector to measure beta emissions emanating from a stopped and static volume of fluid positioned in front of the detector. In other configurations, beta detector 58 can detect beta emissions emanating from radioactive eluate flowing through tubing positioned proximate to the detector. For example, beta detector 58 may detect beta emissions emanating from radioactive eluate as the eluate flows through radioisotope generator discharge line 75 to waste container 54. Controller 80 may receive a signal from beta detector 58 indicative of the beta emissions measured by the beta detector.

Controller 80 may determine the activity of the radioactive eluate based on the beta emissions measured by beta detector 58. For example, controller 80 may compare a magnitude of the beta emissions measured by beta detector 58 to calibration information stored in memory relating different beta emission levels to different radioactive eluate activity levels. Controller 80 can then determine the activity of the radioactive eluate with reference to the calibration information and the beta emissions measured by beta detector 58 for the current radioactive eluate flowing through radioisotope generator discharge line 75. With all measurements made by system 10, controller 80 may account for radioactive decay between the radioisotope generator and a respective detector as the radioactive eluate travels through one or more tubing lines.

Because beta emissions from different radioisotopes are not easily distinguishable from each other, controller 80 may not be able to resolve what portion of the measured activity is attributable to one radioisotope as opposed to one or more other radioisotopes that may be present in the radioactive eluate. In instances where the radioactive decay product present in the radioactive eluate is assumed to be the predominant radioisotope species, controller 80 may set the measured activity of the radioactive eluate as the activity corresponding to the radioactive decay product. For example, in the case of a strontium rubidium radioisotope generator, the activity of radioactive eluate determined using beta detector 58 may be assumed to be the activity of Rb-82 present in the radioactive eluate. This is because the activity of any other radioisotopes that are present in the radioactive eluate may be assumed to be significantly (e.g., orders of magnitude) smaller than the activity of Rb-82 present in the radioactive eluate.

In some examples, pump 40 continuously pumps eluant through radioisotope generator and radioactive eluate is delivered to waste container 54 until the activity level of the radioactive eluate reaches a threshold level. Radioactive eluate generated by radioisotope generator 52 after the generator has been inactive for a period of time may initially have a lower activity than radioactive eluate generated during continued elution of the generator. For example, the activity of bolus radioactive eluate produced using generator 52 may follow an activity curve that varies based on the volume of eluant passed through the generator and the time since the start of the elution. As additional eluant is flowed through the radioisotope generator and time progresses, the activity may decrease from the peak activity to an equilibrium.

In some examples, radioactive eluate generated by radioisotope generator 52 is supplied to waste container 54 until the radioactive eluate reaches a minimum threshold activity value. The minimum threshold activity value can be stored in a memory associated with controller 80. In operation, controller 80 can compare the current activity of the radioactive eluate produced using generator 52 to the activity stored in memory (206). Controller 80 may determine when to actuate second multi-way valve 74 to direct radioactive eluate from waste container 54 to infusion tubing 70, and correspondingly patient line 72, based on the comparison (208).

Since the peak activity of radioactive eluate generated by radioisotope generator 52 may vary over the service life of the generator, the minimum activity threshold may be set relative to one or more previous elution/infusion procedures performed by the radioisotope generator system. For example, for each elution performed by system 10, controller 80 may store in a memory associated with the controller a peak radioactivity detected during that elution, e.g., as measured via beta detector 58. During a subsequent elution, controller 80 may reference the peak radioactivity, which may also be considered a maximum radioactivity, measured during a prior elution. Controller 80 may use that maximum radioactivity from the prior run as a threshold for controlling the radioisotope generator during the subsequent run. In some examples, the threshold is a percentage of the maximum radioactivity measured during a prior elution run, such as an immediate prior elution run. The immediate prior elution run may be the elution run performed before the current elution run being controlled without any intervening elution having been performed between the two evolutions. For example, the threshold may be an activity value falling within a range from 5% to 15% of the magnitude of maximum radioactivity detected during a prior elution run, such as from 8% to 12% of the magnitude of maximum activity, or approximately 10% of the magnitude of the maximum activity. In other examples, the threshold may not be determined based on a prior radioactivity measurement measured using system 10 but may instead be a value stored in a memory associated with controller 80. The value may be set by a facility in charge of system 10, the manufacturer of system 10, or yet other party with control over system 10.

In the example of FIG. 8, controller 80 controls second multi-way valve 74 to divert radioactive eluate from waste container 54 to the patient via infusion tubing 70 and patient line 72 connected to the infusion tubing (210). Upon determining that the activity of radioactive eluate flowing through radioisotope generator discharge line 75 via beta detector 58 has reached the threshold (e.g., equals or exceeds the threshold), controller 80 may control second multi-way valve 74 (e.g., by controlling an actuator associated with the valve) to deliver the radioactive eluate to the patient. Pump 40 may continue pumping the eluant through radioisotope generator 52, thereby delivering radioactive eluate to the patient, until a desired amount of radioactive eluate has been delivered to the patient.

In some examples, the desired amount of radioactive eluate is a set volume of eluate programmed to be delivered to the patient. Controller 80 can determine the volume of radioactive eluate delivered to the patient, e.g., based on knowledge of the rate at which pump 40 pumps and the duration the pump has pumped radioactive eluate. Additionally or alternatively, system 10 may include one or more flow sensors providing measurements to controller 80 concerning the volume of eluant and/or volume of radioactive eluate flowing through one or more tubing lines of the system.

In some examples, controller 80 tracks the cumulative volume of radioactive eluate generated by radioisotope generator 52, e.g., from the time at which the generator is installed in the system 10. Controller 80 may track the volume of radioactive eluate generated during patient infusion procedures as well as other modes of operation where radioactive eluate is generated but may not be supplied to a patient, e.g., during QC testing. In some examples, controller 80 compares the cumulative volume of radioactive eluate generated by radioisotope generator 52 to an allowable limit and prevents at least any further patient infusion of radioactive eluate using the generator when the cumulative volume is determined to exceed (e.g., be equal to or greater than) the allowable limit. In these configurations, the cumulative volume delivered by the radioisotope generator can act as a control point for determining when the generator should be taken out of service. While the allowable limit can vary based on a variety of factors such as the size and capacity of the radioisotope generator, in some examples, the allowable limit is less than 250 L, such as less than 150 L, less than 100 L, less than 50 L, or less than 25 L. For example, the allowable limit may range from 5 L to 100 L, such as from 10 L to 60 L, from 15 L to 40 L, or from 17 L to 30 L. In one particular example, the allowable limit is 17 L. In another particular example, the allowable limit is 30 L. System 10 can have hardware and/or software locks that engage to prevent a subsequent patient infusion procedure once the allowable limit is reached. For example, controller 80 may prevent pump 40 from pumping eluant once the allowable limit has been exceeded.

In addition to or in lieu of controlling the desired amount of radioactive eluate based on the volume of eluate delivered to the patient, controller 80 may control the desired amount of radioactive eluate based on the cumulative amount of radioactivity delivered to the patient (e.g., adjusting for radioactive decay during delivery). Controller 80 may control pump 40 to deliver eluant to radioisotope generator 52, thereby delivering radioactive eluate to the patient, until the cumulative amount of radioactivity delivered to the patient reaches a set limit. Controller 80 can determine the cumulative amount of radioactivity delivered to the patient by measuring the activity of the radioactive eluate via beta detector 58 during the delivery of the radioactive eluate to the patient. When controller 80 determines that the set amount of radioactivity has been delivered to the patient, controller 80 may control pump 40 to cease pumping the eluant and/or control one or more valves in system 10 to redirect flow through the system.

In some examples, controller 80 controls first multi-way valve 64 to redirect eluant flowing through system 10 from radioisotope generator inlet line 66 to bypass line 68. Controller 80 may or may not control second multi-way valve 74 to place radioisotope generator discharge line 75 in fluid communication with the waste line 76 instead of infusion tubing line 70. Controller 80 may control pump 40 to pump eluant through bypass line 68 into infusion tubing 70 and patient line 72. Controller 80 may control the pump to pump a volume of eluant through the lines sufficient to flush residual radioactive eluate present in the lines from the lines into the patient. This may help remove residual sources of radioactivity from the environment surrounding the patient which may otherwise act as interference during subsequent diagnostic imaging. Independent of whether controller 80 controls system 10 to provide an eluant flush following delivery of radioactive eluate to the patient, controller 80 can terminate operation of pump 40 to terminate the patient infusion procedure (212).

As noted above, system 10 may be used to generate and deliver radioactive eluate in other applications in which infusion tubing 70 is not connected to a patient. As one example, system 10 may generate radioactive eluate that is subject to quality control evaluation during a quality control mode of operation. During the quality control mode of operation, radioactive eluate produced by system 10 may be analyzed to determine the radioactivity of one or more species of radioisotopes present in the radioactive eluate. In practice, when eluant is passed through a radioisotope generator containing a parent radioisotope bound on a support material, a daughter decay product radioisotope that binds less tightly to the support material than the parent radioisotope can release into the eluant to form the radioactive eluate. One or more other radioisotopes besides the daughter decay product intended to be eluted into the eluant may also enter the liquid. Periodic quality control evaluation of the radioactive eluate may be performed to determine the activity level of these one or more other radioisotopes to help ensure that the activity level does not exceed a determine limit.

For example, in the case of a strontium-rubidium radioisotope generator, when eluant is passed through the generator, Rb-82 may be generated as a radioactive decay product from Sr-82 contained in the radioisotope generator, thereby generating the radioactive eluate. The eluate may contain radioisotopes besides Rb-82, with the number and magnitude of the radioisotopes varying, e.g., based on the operational performance of the generator. For example, as the generator is used to generate doses of Rb-82, Sr-82 and/or Sr-85 may release from the generator and also enter the eluate. As another example, cesium-131 may enter the eluate in trace amounts. Accordingly, the total amount of radioactivity measured from the radioactive eluate may not be attributable to one particular radioisotope but may instead be the sum amount of radioactivity emitted by each of the different radioisotopes present in the eluate.

Figure 9:
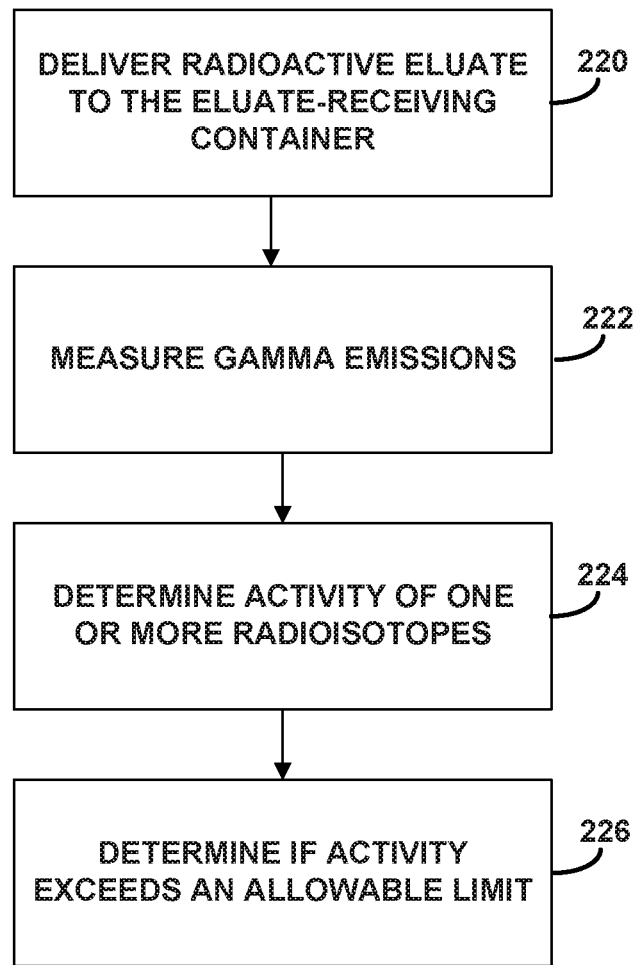
FIG. 9 is a flow diagram of an example technique that may be used to perform a quality control procedure.

During quality control evaluation, the activity of one or more radioisotopes present in the radioactive eluate (e.g., in addition to or in lieu of the decay product targeted for generation by the radioisotope generator) may be determined and compared to one or more allowable thresholds. FIG. 9 is a flow diagram of an example technique that may be used to perform a quality control procedure. For example, the technique of FIG. 9 may be used by system 10 to help ensure that radioactive eluate generated by radioisotope generator 52 meets the standards set for patient infusion. As with FIG. 8, the technique of FIG. 9 will be described with respect to system 10, and more particularly the arrangement of exemplary components described with respect to FIG. 6 above, for purposes of illustration. However, it should be appreciated that the technique may be performed by systems having other arrangements of components and configurations, as described herein.

In the technique of FIG. 9, controller 80 can control system 10 to deliver radioactive eluate to the eluate-receiving container 56 positioned proximate to a gamma detector 60 (220). To initiate the process, an operator may insert eluate-receiving container 56 into third compartment 106 of shielding assembly 28 and close third door 106D to enclose the container in the compartment. Before or after positioning third door 106D over the opening of the third compartment 106, the operator can insert the end of infusion tubing 70 into the eluate-receiving container 56 to place the infusion tubing in fluid communication with the eluate-receiving container. For example, the operator may insert eluate-receiving container 56 in the third compartment 106 of shielding assembly 28, position third door 106D over the opening of the compartment through which the eluate-receiving container was inserted, and then insert the terminal end of infusion tubing line 70 through opening 158 of the door. In some configurations, the terminal end of infusion tubing line 70 includes a needle such that inserting the infusion tubing line 70 through the opening in the third door involves inserting the needle through the opening. The eluate-receiving container 56 may or may not include a septum that is pierced by the needle on the terminal end of infusion tubing line 70 to place the infusion tubing line in fluid communication with the eluate-receiving container. Alternatively, the eluate-receiving container 56 in infusion tubing line 70 may be connected using a variety of different mechanical connection features such as threaded connectors, Luer lock connectors, or yet other types of mechanical joining features.

Independent of how infusion tubing line 70 is placed in fluid communication with eluate-receiving container 56, the resulting arrangement may place radioisotope generator 52 in fluid communication with the eluate-receiving container via second multi-way valve 74. That is, when arranged to perform a quality control elution, the outlet of infusion tubing 70 can be placed in communication with eluate-receiving container 56 and not in communication with patient line 72 or any patient connected to the patient line. When so arranged, radioactive eluate generated by radioisotope generator 52 can be supplied to eluate-receiving container 56 for evaluation by gamma detector 60 instead of being delivered to a patient during a patient infusion procedure.

Once system 10 is suitably arranged to allow eluate-receiving container 56 to receive radioactive eluate from radioisotope generator 52, controller 80 can control the system to generate radioactive eluate that is supplied to the eluate-receiving container. In some examples, controller 80 initiates a quality control elution in response to instructions received via user interface 16 by an operator to perform the quality control elution. For example, controller 80 may execute software that guides the operator through one or more steps to appropriately arrange the components of system 10 for the quality control elution and receives feedback (e.g., via sensors and/or the operator via the user interface) confirming that the components are appropriately arranged before generating radioactive eluate. Controller 80 can control system 10 to execute the quality control elution immediately after arranging the components of system 10 to perform the elution or at a delayed time after the components have been arranged for the quality control elution.

In instances where the quality control procedure takes a comparatively long time to execute, for example, an operator may set system 10 to perform a quality control elution at a time when the system is not typically used for patient infusion procedures. For example, system 10 may be set to perform a quality control procedure at a preset time in the day, such as over the midnight hour or in the evening. As examples, system may be set to perform the quality control elution at a time between 5 PM in the evening and 7 AM the next day, such as between 8 PM in the evening and 6 AM the next day, or between 12 PM and 4 AM the next day in the time zone where the system is located. The operator may install eluate-receiving container 56 and/or tubing in place the eluate-receiving container in fluid communication with the tubing prior to leaving the system unattended. Thereafter, system 10 operating under the control of controller 80 may execute the quality control procedure at a subsequent preprogrammed time. The quality control results may then be available to the operator when they return to the system.

Regardless of the time at which system 10 executes the quality control elution, controller 80 can control pump 40 to pump eluant through radioisotope generator 52, thereby generating the radioactive eluate that is supplied to the eluate-receiving container. In some examples, radioactive eluate generated by radioisotope generator 52 is supplied directly to eluate-receiving container 56 via infusion tubing 70 without diverting an initial portion of the radioactive eluate to waste container 54. In other examples, radioactive eluate generated by radioisotope generator 52 is initially directed to waste container 54 until a threshold level of activity is reached as determined via beta detector 58. Upon determining that radioactive eluate being generated by radioisotope generator 52 has reached a threshold level of activity, controller 80 can control second multi-way valve 74 to direct radioactive eluate flowing from radioisotope generator discharge line 75 to infusion tubing 70 (and eluate-receiving container 56 connected thereto) instead of to waste container 54.

For example, controller 80 may follow steps 200-208 discussed above with respect to FIG. 8 during a quality control elution to supply radioactive eluate to eluate-receiving container 56. Controller 80 can divert radioactive eluate initially generated by radioisotope generator 52 to waste container 54 until the activity of the radioactive eluate as determined via beta emissions measured by beta detector 58 reaches a threshold. Upon the activity of radioactive eluate generated by radioisotope generator 52 reaching the threshold, controller 80 can control multi-way valve 74 to direct the radioactive eluate to eluate-receiving container 56.

Pump 40 can continue supplying eluant to radioisotope generator 52 and thereby supply radioactive eluate to eluate-receiving container 56 until a desired amount of radioactive eluate is supplied to the container. In some examples, the desired amount of radioactive eluate is a pre-established volume of radioactive eluate, e.g., based on the size of eluate-receiving container 56. Controller 80 can control pump 40 to supply an amount of radioactive eluate to eluate-receiving container 56 sufficient to at least partially, and in some cases fully, fill the eluate-receiving container with radioactive eluate. In some embodiments, eluate-receiving container 56 may be filled to greater than 50% of its maximum volume with radioactive eluate, such as from 50% to 100% of its maximum volume, greater than 75% of its maximum volume, or from 60% to 90% of its maximum volume. The total volume to which eluate-receiving container 56 is filled during a quality control procedure, which may be referred to as a quality control (QC) threshold volume may be greater than 5 mL, such as from 5 mL to 100 mL or from 5 mL to 50 mL. As examples, the QC threshold volume may range from 10 mL to 20 mL, from 20 mL to 30 mL, from 30 mL to 40 mL, from 40 mL to 50 mL, from 50 mL to 75 mL, or from 75 mL to 100 mL. For example, in one specification application, the QC threshold volume is about 50 mL.

In addition to or in lieu of controlling the amount of radioactive eluate supplied to eluate-receiving container 56 based on volume, controller 80 may control the amount of radioactive eluate supplied to the container based on activity measurements made by beta detector 58. As radioactive eluate flows past the beta detector 58 to eluate-receiving container 56, the beta detector can measure the beta emissions emitted by the radioactive eluate. Controller 80 can receive a signal from beta detector 58 indicative of the beta emissions measured by beta detector 58 and may compare a magnitude of the beta emissions measured by the beta detector to calibration information stored in memory relating different beta emission levels to different radioactive eluate activity levels. Controller 80 may determine a cumulative amount of activity delivered to eluate-receiving container 56 based on the activity of the radioactive eluate measured by the beta detector and/or the flow rate of the radioactive eluate (e.g., adjusting for radioactive decay during delivery). Controller 80 can compare the cumulative amount of activity delivered to eluate-receiving container 56, which may be referred to as an accumulated radioactive dose supplied to the container, to one or more thresholds stored in a memory associated with the controller.

For example, controller 80 may compare the cumulative amount of activity supplied to eluate-receiving container 56 to a quality control (QC) threshold level stored in a memory associated with the controller. The QC threshold level may be programmed, e.g., by an operator or manufacturer of system 10. In some examples, the QC threshold level is greater than 5 mCi, such as greater than 15 mCi. For example, the QC threshold level may range from 5 mCi to 75 mCi, such as from 10 mCi to 60 mCi, from 15 mCi to 50 mCi, or from 20 mCi to 40 mCi. In one specific example, the threshold QC level is approximately 30 mCi. The threshold QC level can be the total activity of the radioactive eluate supplied to eluate-receiving container 56 as measured by beta detector 58 and as corrected for radioactive decay during delivery based on time and half-life. Where a single radioisotope is assumed to be the dominant source of radioactivity, the threshold level may be assumed to correspond to that radioisotope. In the example of a strontium-rubidium radioisotope generator where Rb-82 is expected to be the dominant source of activity in the radioactive eluate flowing past the beta detector 58, the threshold QC level activity may be designated as a threshold QC level of Rb-82.

Upon determining that the accumulated radioactive dose of radioactive eluate supplied to eluate-receiving container 56 has reached the QC threshold level, controller 80 can control pump 40 to cease pumping eluant through radioisotope generator 52. Accordingly, in these examples, the amount of activity delivered to eluate-receiving container 56 can act as a control point for determining how much volume of radioactive eluate to deliver to the container. Controller 80 may also monitor the volume of radioactive eluate delivered to eluate-receiving container 56 and control pump 40 to cease pumping if the eluate-receiving container will exceed its maximum capacity, even if the QC threshold level has not been reached. In these circumstances, controller 80 may issue a user alert via user interface 16 indicating an issue with the quality control testing.

In the technique of FIG. 9, gamma detector 60 measures gamma emissions emitted by radioactive eluate supplied to eluate-receiving container 56 (220). Gamma detector 60 can continuously measure gamma emissions, e.g., during filling of eluate-receiving container 56 and/or after the eluate-receiving container has suitably filled with radioactive eluate. Alternatively, gamma detector 60 may periodically sample gamma emissions, e.g., at one or more times after eluate-receiving container 56 has suitably filled with radioactive eluate.

In some examples, gamma detector 60 measures gamma emissions emanating from radioactive eluate in eluate-receiving container 56 at least upon the container being initially filled when the pump stopped pumping radioactive eluate to the container. Gamma detector 60 can measure gamma emissions emanating from radioactive eluate in eluate-receiving container at one or more times after the container has filled with radioactive eluate, in addition to or in lieu of measuring the gamma emissions upon the container being initially filled. For example, gamma detector 60 may measure gamma emissions emanating from radioactive eluate in eluate-receiving container 56 after a period of time sufficient for substantially all the initial daughter radioisotope (e.g., Rb-82) in the radioactive eluate to decay.

In some examples, the period of time sufficient for substantially all the initial daughter radioisotope to decay is at least 3 half-lives of the daughter radioisotope, such as at least 5 half-lives of the daughter radioisotope. In the case of Rb-82 which has a half-life of about 76 seconds, the period of time may be greater than 15 minutes, such as greater than 20 minutes, or greater than 30 minutes. For example, the period of time may range from 15 minutes to one hour, such as 25 minutes to 45 minutes. Controller 80 can control gamma detector 60 to measure gamma emissions emanating from radioactive eluate in the eluate-receiving container 56 after the period of time has passed from the filling of the eluate-receiving container. As noted above, gamma detector 60 may or may not continuously measure gamma emissions emanating from the radioactive eluate both before and after the period of time has passed.

The gamma emission energies measured by gamma detector 60 may vary depending on the type of radioisotope generator utilized for radioisotope generator 52 and, correspondingly, the gamma emission energies of specific radioisotopes produced by the generator. In some examples, gamma detector 60 is implemented as a wide range detector that detects a large gamma spectrum. In other examples, gamma detector is implemented as a narrow range detector or is windowed to detect a comparatively narrower gamma spectrum.

In some applications, such as when radioisotope generator 52 is implemented as a strontium-rubidium radioisotope generator, gamma detector 60 may be configured to measure gamma emissions at least in a range from 400 kilo-electron volts (keV) to 600 keV, such as from 450 keV to 550 keV, from 465 keV to 537 keV, or from 511 keV to 514 keV. In some examples, gamma detector 60 measures gamma emissions at least at a gamma emission energy of 511 keV and/or 514 keV. In general, the gamma emission energy ranges detected by gamma detector 60 may be set depending on the gamma emission energies of one or more radioisotopes of interest for measurement.

Gamma detector 60 can send, and controller 80 can receive, a signal indicative of the gamma emissions measured by the gamma detector. In the technique of FIG. 9, controller 80 determines the presence and/or activity of one or more radioisotopes present in the radioactive eluate based on the measured gamma emissions (224). Controller 80 may determine the amount of activity associated with a particular energy line of the gamma spectrum which corresponds to a particular radioisotope, thereby determining the activity of that radioisotope.

In general, activity may be reported in Becquerel (Bq) or Curie (Ci) and is a function of the composition of a particular radioisotope and the amount of the radioisotope in the radioactive eluate. To determine the amount of activity associated with a particular radioisotope, controller 80 may identify a region of interest of the gamma spectrum encompassing the energy line corresponding to that radioisotope and integrate the area under the peak for that energy line. The region of interest may be a region defined between two different energy lines that includes the peak of interest and bounds the region under which the peak area is integrated to determine corresponding activity.

In the case of a strontium-rubidium radioisotope generator, controller 80 may determine an activity of Sr-82 and/or Sr-85 and/or any other desired radioisotopes of interest. In some examples, controller 80 can determine an activity of Sr-82 by determining an activity associated with the 511 keV line of the gamma spectrum. In general, the activity of Sr-82 may not be measured directly via gamma emissions but may be measured by measuring the activity of Rb-82, which is the decay product of Sr-82 and can emit gamma emissions at the 511 keV energy line. In instances where the gamma spectrum is measured after a period of time sufficient for substantially all initial Rb-82 present in the radioactive eluate supplied from radioisotope generator 52 to decay, Rb-82 emissions measured at the 511 keV energy line may be assumed to be Rb-82 decayed from Sr-82 present in the radioactive eluate, thereby providing a measurement of the Sr-82 activity. Controller 80 can determine the net peak integral count in the region of interest encompassing the 511 keV line to determine the activity of Sr-82. Controller 80 may then store the determined activity of Sr-82 in a memory associated with the controller.

As another example, controller 80 can determine an activity of Sr-85 by determining an activity associated with the 514 keV line of the gamma spectrum. Controller 80 can determine the net peak integral count in the region of interest encompassing the 514 keV line to determine the activity of Sr-85. Controller 80 may then store the determined activity of Sr-85 in a memory associated with the controller.

In applications where both the activity of Sr-82 and Sr-85 are determined, controller can determine the respective activity of each radioisotope by gamma spectrum analysis as discussed above. Alternatively, controller 80 may determine the activity of one of Sr-82 or Sr-85 by gamma spectrum analysis as discussed above and determine the activity of the other strontium radioisotope with reference to a ratio stored in memory relating the activity of Sr-82 to the activity of Sr-85. The activity of Sr-82 may be related to the activity of strontium-85 by a known radioisotope ratio, which may be stored in memory associated with controller 80. Controller 80 can determine the activity of one radioisotope by multiplying the determined activity of the other radioisotope by the stored ratio. In some examples, controller 80 sums the determined activity of Sr-82 and the determined activity of Sr-85 to identify the total strontium activity in the radioactive eluate.

If desired, controller 80 can identify the amount of activity associated with other radioisotopes in the radioactive eluate based on the gamma emission data received from gamma detector 60. Controller 80 can identify region(s) of interest encompassing other gamma emission energy lines corresponding to the radioisotopes and determine a net peak integral count for each energy line. Each energy line may correspond to a particular radioisotope, and the correspondence between different energy lines and different radioisotopes may be stored in a memory associated with the controller. Additional details on gamma detector arrangements and gamma emission processing can be found in US Patent Publication No. US2015/0260855, entitled "REAL TIME NUCLEAR ISOTOPE DETECTION," the entire contents of which are incorporated herein by reference.

Activity measurements made for one or more radioisotopes in the radioactive eluate can be stored and/or used for variety of purposes in radioisotope generator system 10. In the example of FIG. 9, controller 80 determines if one or more of the radioisotopes exceeds an allowable limit (226). Controller 80 can compare the determined activity of a particular radioisotope to a threshold stored in memory associated with the controller. For example, controller 80 may compare a determined activity of Sr-82 to an allowable limit for Sr-82 stored in memory. As examples, the allowable limit for Sr-82 may be a Sr-82 level of less than 0.05 μCi per millicurie of Rb-82, such as less than 0.02 μCi per millicurie of Rb-82, about 0.02 μCi per millicurie of Rb-82, less than 0.01 μCi per millicurie of Rb-82, or about 0.01 μCi per millicurie of Rb-82. As another example, controller 80 may compare a determined activity of Sr-85 to an allowable limit for Sr-85 stored in memory. As examples, the allowable limit for Sr-85 may be a Sr-85 level of less than 0.5 μCi per millicurie of Rb-82, such as less than 0.2 μCi per millicurie of Rb-82, about 0.2 μCi per millicurie of Rb-82, less than 0.1 μCi per millicurie of Rb-82, or about 0.1 μCi per millicurie of Rb-82.

The Rb-82 activity level used to evaluate whether the determined activity of Sr-82 and/or Sr-85 exceeds an allowable limit may be a Rb-82 activity (e.g., maximum or minimum Rb-82 activity level) determined via the beta detector 58 or gamma detector 60. In one application, the Rb-82 activity level used to evaluate whether the determined activity of Sr-82 and/or Sr-85 exceeds an allowable limit is a fixed value, such as about 10 millicurie. In other examples, the fixed value of Rb-82 is in the range from 10 millicurie Rb-82 to 100 millicurie Rb-82, such as 20 millicurie, 30 millicurie, 40 millicurie, 50 millicurie, 60 millicurie, 70 millicurie, 80 millicurie, or 90 millicurie. In one embodiment, controller 80 determines strontium levels, as a ratio of Sr-82 (in μCO to Rb-82 (in mCi), with a true positive rate of at least 95% with a 95% confidence level, at 0.01 μCi Sr-82 per millicurie of Rb-82. In another embodiment, controller 80 determines detect strontium levels, as a ratio of Sr-85 (in μCO to Rb-82 (in mCi), with a true positive rate of at least 95% with a 95% confidence level, at 0.1 μCi Sr-85 per millicurie of Rb-82.

System 10 can take a variety of different actions if the determined activity of one or more radioisotopes during a quality control procedure is determined to exceed an allowable limit. In some examples, controller 80 may initiate a user alert (e.g., a visual, textual, mechanical (e.g., vibratory), audible user alert) such as via user interface 16, indicating that a measured radioisotope in the radioactive eluate produced using the radioisotope generator 52 has exceeded allowable limit. Additionally or alternatively, controller 80 may control system 10 to prevent a subsequent patient infusion procedure if it is determined that a radioisotope in the radioactive eluate has exceeded an allowable limit. System 10 can have hardware and/or software locks that engage to prevent a subsequent patient infusion procedure once the allowable limit is reached. For example, controller 80 may prevent pump 40 from pumping eluant once the allowable limit has been exceeded. In some examples, controller 80 electronically transmits a message indicating that a radioisotope in the radioactive eluate has exceeded allowable limit to an offsite location, e.g., for monitoring and/or evaluating the operation of the radioisotope generator.

System 10 may be used to generate and deliver radioactive eluate in yet other applications in which infusion tubing 70 is not connected to the patient, e.g., to help maintain the quality and accuracy of radioactive eluate generated by the system. As yet another example, system 10 may generate radioactive eluate as part of a constancy evaluation to evaluate the accuracy and/or precision of activity measurements being made by beta detector 58. Since beta detector 58 may be used to control the cumulative amount of activity delivered to a patient during a patient infusion procedure, ensuring that the detector is appropriately calibrated can help ensure accurate dosing of radioactive eluate.

FIGS. 10-16 describe exemplary calibration and quality control ("QC") test(s) that may be periodically performed on the infusion system, such as dose calibration using beta detector 58 and/or calibration of gamma detector 60 to help ensure the reliability of measurements made by the infusion system using one or both detectors. Each performance test may be used to evaluate the accuracy and/or precision of activity measurements made by the detector undergoing testing. Corrective action such as recalibration or system lockout may be taken if a test is found to fall outside of an acceptable limit. Any test or combination of tests described may be performed using beta detector 58, gamma detector 60, or both beta detector 58 and gamma detector 60 as part of a quality control and/or calibration protocol.

For example, QC test(s) performed using the beta detector 58 may include a dose calibration test, a dose linearity test, a dose repeatability test, a dose constancy test, and combinations thereof. QC test(s) performed using the gamma detector 60 may include a gamma detector calibration test, a gamma detector repeatability test, a gamma detector linearity test, and combinations thereof. In some examples, a column wash is performed on radioisotope generator 52 prior to executing a QC test or series of QC test. The column wash can involve pumping a fixed volume of eluant through radioisotope generator 52 and directing the resulting eluate to waste container 54. The fixed volume may range from 10 ml to 100 ml, such as from 25 ml to 75 ml, or from 35 ml to 65 ml. The column wash can push eluate that remained stationary in radioisotope generator 52 over time out of the generator and move the generator chemistry out of the equilibrium state and into the steady state. A column wash may be performed before any patient infusion procedure as well.

When calibrating gamma detector 60, a detector energy window calibration QC test may be performed with (e.g., prior to) any of the other QC test(s) to be performed on the detector. A source of radioisotope that has a gamma emission energy that is the same as or similar to the parent radioisotope contained in radioisotope generator 52 (e.g., strontium) can be positioned for gamma detector 60 to read gamma radiation emitted from the source. The source of radioisotope may have a gamma emission energy that is within plus or minus 30% of the gamma emission energy of the parent radioisotope contained in radioisotope generator 52, such as plus or minus 20%, plus or minus 10%, plus or minus 15%, plus or minus 5%, plus or minus 1%, or plus or minus 0.5%. Example sources of radioisotope that may be used include Sr-82, Sr-85, sodium-22, and cesium-137.

The radioisotope source can be introduced into third compartment 106. Operating under the control of controller 80, gamma detector 60 can read the gamma spectrum emitted by the calibration source. Controller 80 can calculate a difference between the calculated peak channel in the gamma spectrum and the expected peak channel. Controller 80 may determine if the determined difference deviates by more than a tolerable range. In various examples, the tolerable range may be plus or minus 20%, such as plus or minus 10%, or plus or minus 5%. Controller 80 may determine if the difference exceeds the tolerable range. Controller 80 may take a variety of actions if the determined difference exceeds the tolerable range. For example, controller 80 may issue a user alert (e.g., the user interface 16) informing an operator if the peak channel exceeds the tolerable range for the expected peak channel. Additionally or alternatively, controller 80 may initiate recalibration (e.g., by adjusting the voltage so the peak channel is aligned with expected peak channel).

As another example when calibrating gamma detector 60, background radiation may be measured by the gamma detector in the absence of a specific radioisotope source being introduced into third compartment 106. The background radiation may be measured after performing the detector energy window calibration but prior to performing any other QC test(s) or at other times during the QC protocol. For example, during a daily QC protocol, background radiation may be measured before performing other QC tests without performing a detector energy window calibration. The background radiation measurement may ensure that there are no gamma emitting sources external to system 10 emitting at a level that causes distortion or error of the gamma measurements made by gamma detector 60 during a QC test. Controller 80 may take a variety of actions if excessive background gamma radiation is detected, including those actions described herein.

QC test(s) may be performed using beta detector 58 and/or gamma detector 60 at appropriate frequencies to maintain the high quality operation of system 10. In some examples, a full QC protocol is performed following installation or replacement of a component (e.g., tubing line, radioisotope generator, detector), after a major repair is performed on the system (e.g., one performed by a representative of the manufacturer of system 10) and/or annually as part of a preventive maintenance plan. Such a full protocol may involve performing a gamma detector energy window calibration QC test, a background radiation test, a column wash, a gamma detector calibration test, a repeatability test, a gamma detector linearity test, a gamma detector constancy test, a dose constancy test, a dose linearity test, and/or a dose repeatability test.

A smaller QC protocol may be performed on a more frequent basis. Such a protocol may involve performing a background radiation test with the gamma detector, a column wash, dose constancy test using the beta detector along with parent radioisotope (e.g., strontium) level test using the gamma detector, and a gamma detector constancy test. Independent of the specific QC test or protocol set of tests performed, the tests may be performed at any desired frequency, such as a QC period ranging from every day to every 50 days, such as from 4 to 45 days, 4 to 10 days, 11 to 17 days, 18 to 24 days, 25 to 31 days, 32 to 38 days, or 39 to 45 days, or at approximately daily, 7 days, 14 days, 21 days, 28 days, 35 days, or 42 days. When performing any QC test described herein where eluate is passed through tubing, the test may be conducted at one or more flow rates (in which case the test may be repeated at multiple flow rates. The flow rates can range from 10 ml/min to 60 ml/min, such as 20 ml/min, 35 ml/min, or 50 ml/min, although other flow rates can be used depending on the configuration of the system and/or desire of the user.

Figure 10:
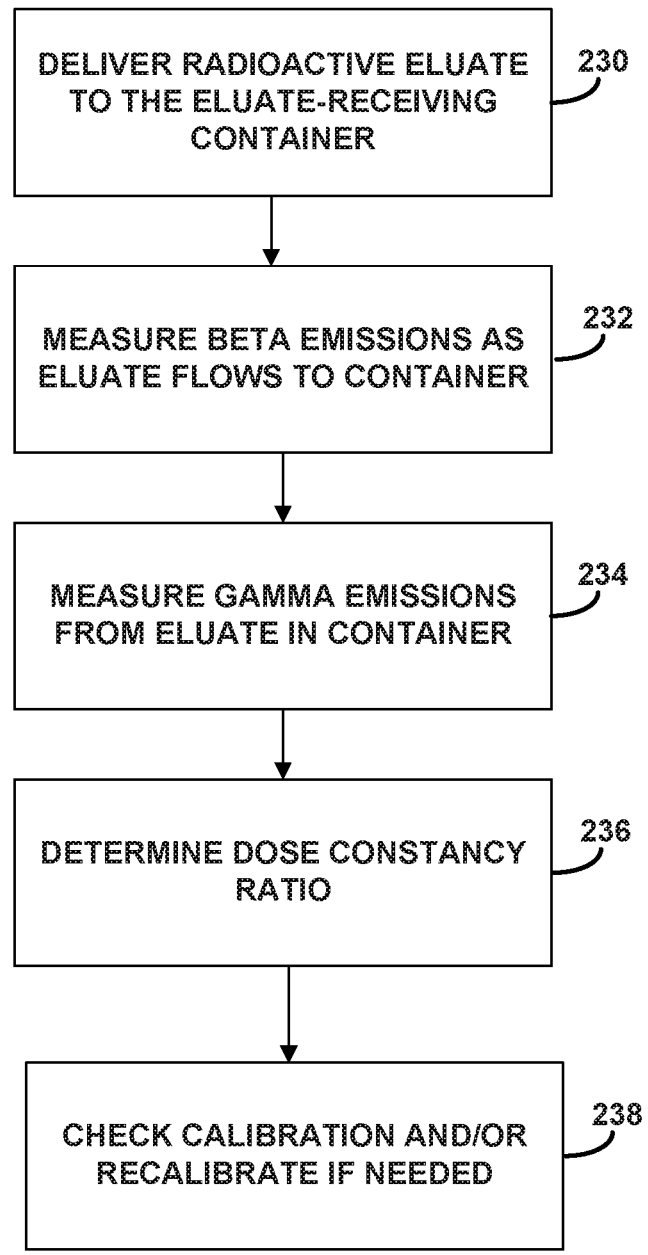
FIGS. 10-16 describe exemplary calibration and quality control test that may be periodically performed on an infusion system according to the disclosure.

FIG. 10 is a flow diagram of an example technique that may be used to perform a constancy check procedure. For example, the technique of FIG. 10 may be used by system 10 to evaluate dose constancy using beta detector 58.

To perform dose constancy, controller 80 can control system 10 to deliver radioactive eluate to the eluate-receiving container 56 positioned proximate gamma detector 60 (230). The process of initiating the constancy evaluation and delivering radioactive eluate to eluate-receiving container 56 can follow that described above with respect to FIG. 9 in connection with the quality control evaluation procedure. For example, to initiate the process, an operator may insert eluate-receiving container 56 into third compartment 106 of shielding assembly 28 and place infusion tubing 70 in fluid communication with the eluate-receiving container, as discussed above.

Once system 10 is suitably arranged to allow eluate-receiving container 56 to receive radioactive eluate from radioisotope generator 52, controller 80 can control the system to generate radioactive eluate that is supplied to the eluate-receiving container. In some examples, controller 80 initiates a constancy elution in response to instructions received via user interface 16 by an operator to perform the constancy elution. For example, controller 80 may execute software that guides the operator through one or more steps to appropriately arrange the components of system 10 for the constancy elution and receives feedback (e.g., via sensors and/or the operator via the user interface) confirming that the components are appropriately arranged before generating radioactive eluate. Controller 80 can control system 10 to execute the constancy elution immediately after arranging the components of system 10 to perform the elution or at a delayed time after the components have been arranged for the constancy eluate, as discussed above with respect to the quality control procedure in connection with FIG. 9.

Controller 80 may follow steps 200-208 discussed above with respect to FIG. 8 during a quality control elution to supply radioactive eluate to eluate-receiving container 56. Controller 80 can divert radioactive eluate initially generated by radioisotope generator 52 to waste container 54 until the activity of the radioactive eluate as determined via beta emissions measured by beta detector 58 reaches a threshold. Upon the activity of radioactive eluate generated by radioisotope generator 52 reaching the threshold, controller 80 can control multi-way valve 74 to direct the radioactive eluate to eluate-receiving container 56.

Pump 40 can continue supplying eluant to radioisotope generator 52 and thereby supply radioactive eluate to eluate-receiving container 56 until a desired amount of radioactive eluate is supplied to the container. When controller 80 controls pump 40 to supply radioactive eluate to eluate-receiving container 56 until a desired amount of radioactive eluate is supplied to the container, the controller can determine the cumulative amount of radioactivity delivered to the eluate-receiving container by measuring the activity of the radioactive eluate via beta detector 58 during the delivery of the radioactive eluate to the container. Controller 80 can also account for radioactive decay between beta detector 58 and eluate-receiving container 56 (e.g., between the time when the activity is measured by beta detector 58 and the time when the activity is measured by gamma detector 60). Alternatively, the desired amount of radioactive eluate may be a pre-established volume of radioactive eluate and/or a cumulative amount of activity (e.g., corresponding to a QC threshold) delivered to eluate-receiving container 56, as also discussed above with respect to FIG. 9.

As radioactive eluate flows past the beta detector 58 to eluate-receiving container 56, the beta detector can measure the beta emissions emitted by the radioactive eluate (232). Controller 80 can receive a signal from beta detector 58 indicative of the beta emissions measured by beta detector 58 and may compare a magnitude of the beta emissions measured by the beta detector to calibration information stored in memory relating different beta emission levels to different radioactive eluate activity levels. Controller 80 may determine a cumulative amount of activity delivered to eluate-receiving container 56, which may be referred to as an accumulated radioactive dose supplied to the container, based on the activity of the radioactive eluate measured by the beta detector and/or the flow rate of the radioactive eluate.

Upon determining a suitable amount of radioactive eluate has been supplied to eluate-receiving container 56, e.g., that the accumulated radioactive dose supplied to eluate-receiving container has reached a threshold level, controller 80 can control pump 40 to cease pumping the eluant through radioisotope generator 52. When radioactive eluate stops being introduced into eluate-receiving container 56, the filling of the container may be designated as being complete. This can establish an end of filling time utilized from which subsequent activity may be benchmarked.

In the technique of FIG. 10, gamma detector 60 measures gamma emissions emitted by radioactive eluate supplied to eluate-receiving container 56 (234). Gamma detector 60 can continuously measure gamma emissions, e.g., during filling of eluate-receiving container 56 and/or after the eluate-receiving container has suitably filled with radioactive eluate. Alternatively, gamma detector 60 may periodically sample gamma emissions, e.g., at one or more times after eluate-receiving container 56 has suitably filled with radioactive eluate.

In some examples, gamma detector 60 measures gamma emissions emanating from radioactive eluate in eluate-receiving container 56 within a constancy window, which may be a time window measured from the end of the filling of eluate-receiving container 56. For example, gamma detector 60 may measure gamma emissions emanating from radioactive eluate in eluate-receiving container 56 within a constancy time window ranging from 0 seconds from the end of the filling of the eluate-receiving container to 1800 seconds after the end of the filling, such as from 500 seconds to 1500 seconds from the end of the filling, from 700 seconds to 1000 seconds from the end of the filling, or from 793 seconds to 807 seconds from the end of the filling of the eluate-receiving container. Gamma detector 60 can measure gamma emissions emanating from radioactive eluate in eluate-receiving container continuously during the duration of the constancy time window or at one or more times within the constancy time window.

Gamma detector 60 can send, and controller 80 can receive, a signal indicative of the gamma emissions measured by the gamma detector. Controller 80 can further determine the activity of Rb-82 in the eluate-receiving container based on the gamma emissions measured by gamma detector 60, thereby providing an accumulated constancy gamma activity measurement. Controller 80 may determine the amount of activity associated with a 511 keV energy line and/or 776 keV energy line of the gamma spectrum which corresponds to Rb-82. For example, controller 80 may determine the net peak integral count in a region of the gamma spectrum encompassing the 511 keV line and/or 776 keV line to determine the activity of Rb-82. Controller 80 may then store the determined activity of Rb-82 in a memory associated with the controller.

In the technique of FIG. 10, controller 80 compares the activity of Rb-82 determined using beta detector 58 to the activity of Rb-82 determined using gamma detector 60, e.g., by calculating a constancy ratio (236). For example, controller 80 may calculate a constancy ratio based on the accumulated radioactive dose (or beta emission counts) measured by beta detector 58 and supplied to eluate-receiving container 56 and the accumulated constancy gamma activity (or gamma emission counts) measured by gamma detector 60. The constancy ratio may be calculated at least by dividing the accumulated radioactive dose by the accumulated constancy gamma activity.

In some examples, controller 80 further compares the determined constancy ratio to one or more thresholds stored in memory associated with the controller. For example, controller 80 may compare the determined constancy ratio to a reference constancy ratio stored in memory. Controller 80 may determine if the determined constant ratio deviates from the reference conference ratio by more than a tolerable range. In various examples, the tolerable range may be plus or minus 20% of the reference constancy ratio, such as plus or minus 10% of the reference constancy ratio, or plus or minus 5% of the reference constancy ratio. Controller 80 may determine if the constancy ratio exceeds the tolerable range for the reference constancy ratio. Controller 80 may take a variety of actions if the determined constancy ratio exceeds the tolerable range for the reference constancy ratio.

In some examples, controller 80 issues a user alert (e.g., the user interface 16) informing an operator if the determined constancy ratio exceeds the tolerable range and/or the reference constancy ratio. Additionally or alternatively, controller 80 may initiate a calibration check and/or dose recalibration of the system (238). In some examples, controller 80 initiates calibration check and/or dose calibration by executing software to automatically perform such check or calibration or by guiding the operator through steps to perform such check or calibration. To perform a dose calibration, a controller associated with system 10 may generate and store in memory one or more coefficients or other calibration information that is subsequently used by the system to process data generated by beta detector 58 corresponding to the amount of activity measured by the detector.

In some examples, a dose recalibration is performed using a dose calibrator external to and separate from system 10. The dose calibrator may itself be calibrated using a primary standard. Controller 80 may guide an operator via user interface 16 by providing instructions to the operator for generating a sample of radioactive eluate. The sample of radioactive eluate can then be transported to the separate dose calibrator and the activity of Rb-82 in the sample determined using the dose calibrator. Controller 80 may receive the determined activity of Rb-82 from the dose calibrator (e.g., by being wired or wirelessly connected to the dose calibrator and/or by operator entry of the information via user interface 16). Controller 80 can store the determined activity of Rb-82 from the dose calibrator in memory and/or use the information to modify calibration settings used by system 10 to process data generated by beta detector 58 corresponding to the activity of radioactive eluate flowing through system 10.

As another example, controller 80 may use the activity of Rb-82 determined using gamma detector 60 to modify calibration settings used by system 10 to process data generated by beta detector 58. For example, controller 80 may store the activity of Rb-82 determined using gamma detector 60 in memory and/or use the information to modify calibration settings used by system 10 to process data generated by beta detector 58 corresponding to the activity of radioactive eluate flowing through system 10.

Figure 11:
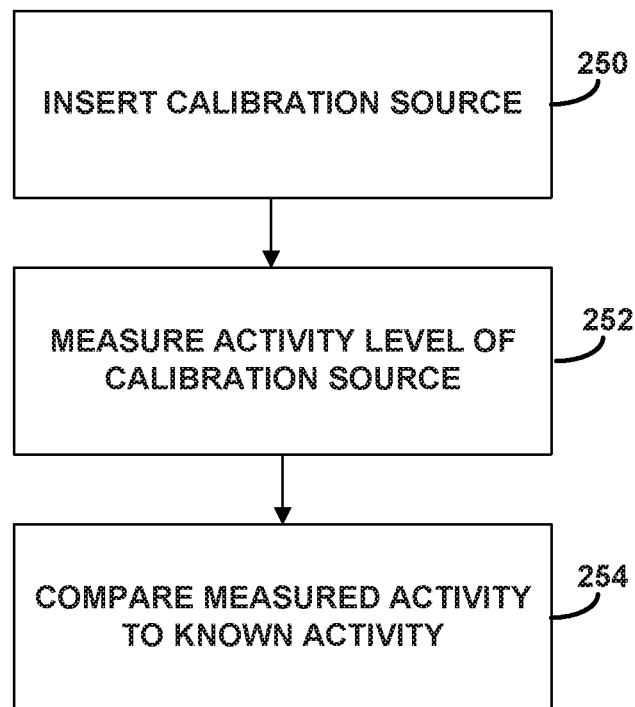

FIG. 11 is a flow diagram of an example technique that may be used to check the accuracy of activity measurements made by gamma detector 60. For example, the technique of FIG. 11 may be used by system 10 to evaluate whether gamma detector 60 is providing accurate and/or precise activity measurements of the radioactive eluate generated by radioisotope generator 52.

To perform a calibration and accuracy test on gamma detector 60, the gamma detector may be exposed to a calibration source having a known (or otherwise expected) level of activity (250). The calibration source may be placed in third compartment 106 adjacent gamma detector 60 and statically held in the third compartment for a period of time sufficient for the gamma detector to measure the activity of the calibration source. For example, when the calibration source is a solid material, eluate-receiving container 56 can be removed from third compartment 106 and the calibration source can be placed in the compartment. Alternatively, if the calibration material is in a liquid state, the calibration material can be pumped into eluate-receiving container 56 that is placed in the third compartment.

Typical calibration sources that may be used to evaluate the accuracy of gamma detector 60 are NIST (National Institute of Standards and Technology) traceable radioisotope standards. The calibration source may be selected to have an activity level similar to that observed by gamma detector 60 during typical operation of system 10. For example, the calibration source may have an activity level ranging from 0.01 µCi to 2 mCi, such as from 0.05 to 1 mCi, from 0.1 µCi to 100 µCi, from 1 µCi to 75 µCi, from 25 µCi to 65 µCi, from 0.1 µCi to 30 µCi, from 1 µCi to 15 µCi, or from 8 µCi to 12 µCi. The calibration source may have a known (or otherwise expected) activity level to which the activity level detected by gamma detector 60 can be compared.

Example isotopes that can be used as a calibration source to evaluate the accuracy of gamma detector 60 include, but are not limited to, Na-22, Cs-131, Ga-68, and Ge-68. The calibration source may be stored in a shielded well or transport container separate from shielding assembly 28. The calibration source may be stored in its shielded housing on or near system 10 and removed from its shielded housing and inserted into third compartment 106 to perform an accuracy test. Alternatively, the calibration source may be brought from an external site, for example in a shielded housing, for periodic calibration testing.

Controller 80 may execute software that guides the operator through one or more steps to appropriately arrange the calibration source in third compartment 106 of system 10 for the accuracy test. Controller 80 can further control gamma detector 60 to measure the activity level of the calibration source received in third compartment 106 (252). Controller 80 can control gamma detector 60 to measure the activity level of the calibration source concurrent with or immediately after inserting the calibration source in the compartment or at a delayed time after the source has been placed in the compartment, as discussed above with respect to the quality control procedure in connection with FIG. 9.

After detecting gamma radiation emanating from the calibration source having the known activity, controller 80 may identify a gamma radiation spectrum region of interest from which the activity of the sample is determined. In the case of a Na-22 calibration source, the region of interest can encompass the 511 keV peak in a gamma ray spectrum generated from the sample. Controller 80 can determine the net peak integral count for the region of interest to determine the amount of activity measured by gamma detector 60 at the energy line.

In the technique of FIG. 11, controller 80 compares the measured activity of the calibration source to a known activity of the calibration sample (254). System 10 may be informed of the known activity of the calibration source, e.g., by entering the known activity via user interface 16. The activity of the calibration source received by controller 80 can then be stored in a memory associated with the controller. Controller 80 can account for the decay of the activity of the calibration source using the known half-life of the radionuclide. Controller 80 can compare the determined activity of the calibration source as measured by gamma detector 60 to the known activity stored in memory. Controller 80 may determine if the determined activity deviates from the known activity by more than an acceptable threshold. In some examples, the acceptable threshold may be within plus or minus 10% of the known activity, such as within plus or minus 5% of the known activity, within plus or minus 3% of the known activity, within plus or minus 2% of the known activity, or within plus or minus 1% of the known activity.

Controller 80 may take a variety of actions if the determined activity of the calibration source measured by gamma detector 60 exceeds the acceptable threshold of the known activity of the calibration source. In some examples, controller 80 issues a user alert (e.g., via user interface 16) informing an operator of the determined activity exceeds the acceptable threshold. Additionally or alternatively, controller 80 may calculate and/or store calibration data (e.g., a calibration ratio) relating the measured activity of the calibration source measured using gamma detector 60 to the known activity of the calibration source. Controller 80 can subsequently use this calibration information during operation to adjust activity measurements made using gamma detector 60.

Figure 12:
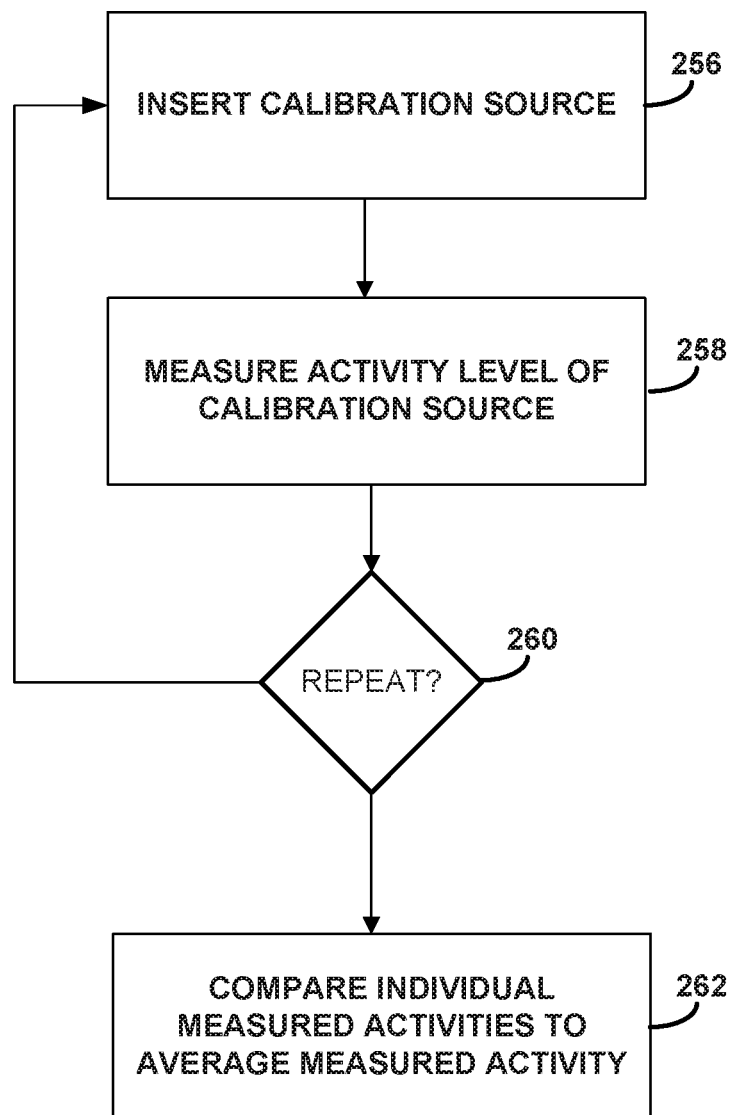

FIG. 12 is a flow diagram of another example technique that may be used to evaluate the repeatability or precision of activity measurements made by gamma detector 60. The technique of FIG. 12 may be used by system 10 to evaluate whether gamma detector 60 is providing consistent and repeatable activity measurements across multiple sample acquisitions of a sample at the same activity level.

In the technique of FIG. 12, a repeatability test may be performed on gamma detector 60 by repeatedly exposing the gamma detector to the same calibration source having a known level of activity (256). The calibration source used to perform the repeatability test may be selected from any of those discussed above with respect to the accuracy test described in connection with FIG. 11. The calibration source may be placed adjacent (e.g., near and/or in front of) gamma detector 60, e.g., by inserting the calibration source in third compartment 106 of shielding assembly 28. The calibration source may be held statically in front of gamma detector 60 for a period of time sufficient for the gamma detector to measure the activity of the calibration source.

After detecting gamma radiation emanating from the calibration source having the known activity, controller 80 may determine the activity of the calibration source (258) as discussed above. The calibration source can be removed from third compartment 106, held outside of the compartment for a period of time, and reinserted back into the compartment (260). That is, the calibration source may be inserted into and removed from the third compartment multiple times. Alternatively, the calibration source may be left in third compartment 106 and the activity of the calibration source measured multiple times. Operating under the control of controller 80, gamma emissions emitted by the calibration source can be measured and the activity of the calibration source determined. For example, the gamma emissions emitted by the calibration source can be measured each time the calibration source is inserted into third compartment 106 and/or multiple times while the calibration source remains in the third compartment. As a result, the activity of the calibration source can be repeatedly determined to evaluate the consistency with which gamma detector 60 measures a sample at the same activity level.

In the technique of FIG. 12, the activity of the calibration source may be measured at least twice, such as at least 3 times, at least 5 times, or at least 10 times. For example, the activity of the calibration source may be measured from 2 times to 20 times, such as from 5 times to 15 times.

After repeatedly measuring the activity of the calibration source a desired number of times, the technique of FIG. 12 includes comparing each measured activity to an average of multiple of the measured calibration activities (262). In some examples, controller 80 determines an average (e.g., mean, median) measured activity of the calibration sample based on all of the measurements made during the test. Controller 80 may further compare each individual measured activity determined during the test to the average measured activity and determine if any one measured activity deviates from the average measured activity by more than acceptable threshold. In some examples, the acceptable threshold may be within plus or minus 10% of the average measured activity, such as within plus or minus 5% of the average measured activity, or within plus or minus 2% of the average measured activity.

If controller 80 determines that any one of the plurality of measured activities exceeds the average measured activity by more than the acceptable threshold, the controller may take action to indicate that gamma detector 60 is not producing sufficiently repeatable results. In some examples, controller 80 issues a user alert (e.g., via user interface 16) informing an operator that gamma detector 60 is not producing sufficiently repeatable results.

Figure 13:
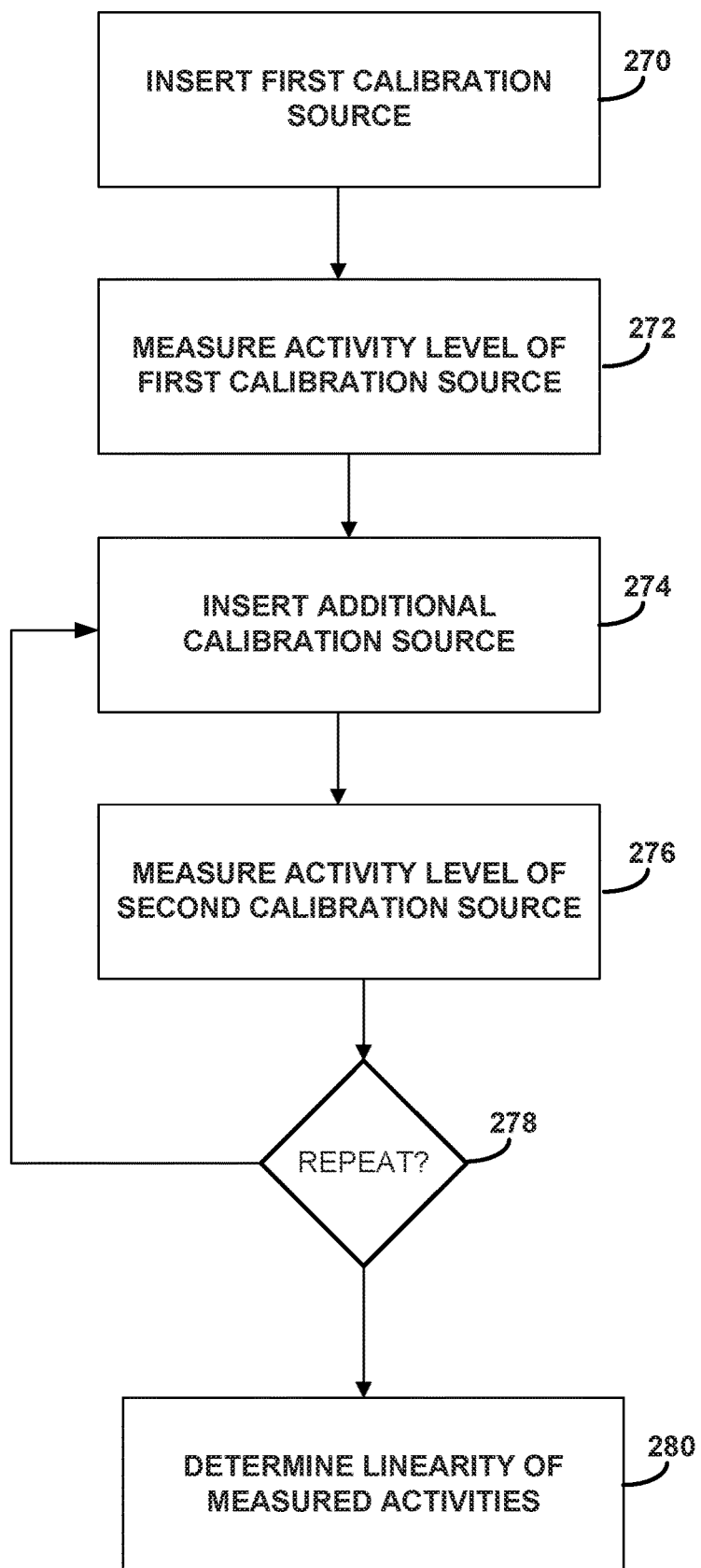

FIG. 13 is a flow diagram of an example technique that may be used to evaluate the linearity of activity measurements made by gamma detector 60. Evaluation of detector linearity can determine if gamma detector 60 is providing a response that is linearly related to the activity of the sample being measured over the activity range expected to be observed by gamma detector 60 during operation.

To evaluate the linearity of gamma detector 60, one or more (e.g., multiple) calibration sources each having a known activity can be placed in front of gamma detector 60. Each individual calibration source (or single calibration source, if only one is used) can be selected to have a half-life effective to provide sufficient measurable decay over the time span of measurement. If multiple calibration sources are used, the multiple sources can be selected so each specific calibration source has a different activity level than each other calibration source, providing a range of activities over which gamma detector 60 measures gamma emissions. The linearity of the activities measured by gamma detector 60 can be evaluated to determine the linearity of the detector.

The particular activities of the calibration sources used to evaluate the linearity of gamma detector 60 may be selected to cover the range of activities expected to be observed by the gamma detector during normal operation. For example, where system 10 is implemented so gamma detector 60 measures a comparatively high level of daughter radioisotope and also measures a comparatively low level of parent radioisotope in a sample under evaluation, the calibration sources may be selected to cover the range from the high radioisotope activity level to the low radioisotope level. In some examples, the activity of the calibration sources used to measure the linearity of gamma detector 60 may range from 0.01 µCi to 2 mCi, such as from 0.05 to 1 mCi, from 0.1 µCi to 100 µCi, 0.05 µCi to 50 µCi, or 0.1 µCi to 30 µCi.

The calibration sources used to perform the gamma detector linearity test may be selected from any of those discussed above with respect to the accuracy test described in connection with FIG. 11. In some examples, the same type of calibration source (e.g., Na-22) at different activity levels is used to test the linearity of gamma detector 60. In other examples, multiple different types of calibration sources at different activity levels are used to test the linearity of gamma detector 60. For example, one type of calibration source at different activity levels may be used to test the comparatively low end of the activity range and another type of calibration source at different activity levels may be used to test the comparatively high end of the activity range. For example, a solid calibration source (e.g., Na-22) may be used to evaluate the low end of the linearity range and a liquid calibration source (e.g., daughter radioisotope such as Rb-82 generated by generator 52) may be used to evaluate the high end of the linearity range.

In the example of FIG. 13, a calibration source having a first activity level can be placed in front of gamma detector 60, e.g., by inserting the calibration source in third compartment 106 of shielding assembly 28 (270). The calibration source may be held statically adjacent to gamma detector 60 for a period of time sufficient for the gamma detector to measure the activity of the calibration source. After detecting gamma radiation emanating from the calibration source having the first activity level, controller 80 can measure the activity level of the calibration source (272) as discussed above and store the measured activity in a memory associated with the controller.

A calibration source having a second activity level different than the first activity can be placed in front of gamma detector 60, e.g., by inserting the calibration source in third compartment 106 of shielding assembly 28 (274). Again, the calibration source may be held statically in front of gamma detector 60 for a period of time sufficient for the gamma detector to measure the activity of the calibration source.

After detecting gamma radiation emanating from the calibration source having the second activity level, controller 80 can measure the activity level of the calibration source (274) as discussed above and store the measured activity in a memory associated with the controller.

One or more additional calibration sources each having a different activity level than each other, and than the first and second calibration sources already measured by gamma detector 60, may also be placed in front of the gamma detector (278). Gamma detector 60 may measure the activity of the additional calibration source(s) and store the measured activity in a memory associated with the controller. In some examples, at least three calibration sources are used having different activity levels over an expected activity range that gamma detector 60 is expected to measure during operation. In some other examples at least five calibration sources having different activity levels are used.

After measuring the activity levels of a suitable number of calibration sources, the technique of FIG. 13 involves linearly regressing the data and determining an R-squared value for the measured activity values. R-squared is a statistical measure of how close the data are to a fitted regression line. Controller 80 may determine an R-squared value for the measured activity values of the different calibration sources. Controller 80 may further compared the determined R-squared value to a threshold stored in memory. In some examples, the threshold may require the R-squared value be greater than 80%, such as greater than 90%, greater than 95%, or greater than 98%. If controller 80 determines that the R-squared value is below the required threshold, the controller may take action to indicate that gamma detector 60 is not producing sufficiently linear results. In some examples, controller 80 issues a user alert (e.g., via user interface 16) informing an operator that gamma detector 60 is not producing sufficiently linear results.

As noted, the calibration sources used to measure the linearity of gamma detector 60 may range in activity level from the comparatively high activity levels associated with a daughter radioisotope (e.g., Rb-82) to comparatively low activity levels associated with a parent radioisotope and/or contaminant radioisotope (e.g., Sr-82, Sr-85). In some examples, system 10 operating under the control of controller 80 is configured to perform multiple gamma detector linearity tests, including one covering the high range of activity levels expected to be observed by gamma detector 60 and one covering the low range of activity levels expected to be observed by the gamma detector.

In some applications when so configured, controller 80 may control system 10 to generate radioactive eluate via radioisotope generator 52 to provide a radioisotope source for testing one of the linearity ranges (e.g., the comparatively high activity range). Controller 80 may follow steps 200-208 discussed above with respect to FIG. 8 during a quality control elution to supply radioactive eluate to eluate-receiving container 56. Controller 80 can divert radioactive eluate initially generated by radioisotope generator 52 to waste container 54 until the activity of the radioactive eluate as determined via beta emissions measured by beta detector 58 reaches a threshold. Upon the activity of radioactive eluate generated by radioisotope generator 52 reaching the threshold, controller 80 can control multi-way valve 74 to direct the radioactive eluate to eluate-receiving container 56.

Gamma detector 60 can measure gamma emissions emitted by radioactive eluate supplied to eluate-receiving container 56. Gamma detector 60 can continuously measure gamma emissions, e.g., during filling of eluate-receiving container 56 and/or after the eluate-receiving container has suitably filled with radioactive eluate. Gamma detector 60 may periodically sample gamma emissions, e.g., at one or more times after eluate-receiving container 56 has suitably filled with radioactive eluate.

The linearity of gamma detector 60 may be tested across a range of activity levels associated with the daughter radioisotope in the radioactive eluate supplied to the eluate-receiving container, e.g., as the daughter radioisotope decays to progressively lower activity levels. To perform the gamma detector linearity testing across this range, activity levels measured by gamma detector 60 across multiple pre-determined periods following the end of elution may be used to evaluate linearity. In some embodiments of the present invention, the multiple pre-determined periods can range from 500 seconds to 1600 seconds, from 600 seconds to 1300 seconds, from 700 seconds to 1200 seconds, or from 750 seconds to 1100 seconds. For example, gamma detector 60 may make a first activity measurement within a time range from 600 to 950 seconds following the end of elution, such as from 700 to 800 seconds, from 725 to 775 seconds, or at approximately 750 seconds. Gamma detector 60 may make a second activity measurement at a later time within a range from 650 to 1000 seconds following the end of elution, such as from 750 to 850 seconds, from 775 to 825 seconds, or at approximately 800 seconds. Gamma detector 60 may make a third activity measurement at a yet later time within a range from 950 to 1250 seconds following the end of elution, such as from 1050 to 1150 seconds, from 1075 to 1125 seconds, or at approximately 1100 seconds. Activity measurements at different time periods including earlier or later times (and/or additional measurements within the overall time) may be made and included as part of the linearity calculation as needed.

In either case, the resulting measured activity levels of radioactive eluate in eluate-receiving container 56 made by gamma detector 60 can be evaluated for linearity. Controller 80 may linearly regress the data and determine an R-squared value for the measured activity values at the different times. Controller 80 may further compared the determined R-squared value to a threshold stored in memory, as discussed above.

To measure the linearity of gamma detector 60 across a comparatively low range of activity levels associated with the parent radioisotope and/or contaminants in the radioactive eluate delivered to the eluate-receiving container, external calibration sources (e.g., Na-22) may be inserted into third compartment 106. The external calibration sources may range in activity level from approximately 0.1 μCi to approximately 10 μCi, which may correspond to the range of parent radioisotope activity levels that may be observed by gamma detector 60 during operation. The linearity of activity measurements made using the external calibration sources may be regressed and an R-squared value calculated, as discussed above. Controller 80 may further compared the determined R-squared value to a threshold stored in memory, as further discussed above.

Figure 14:
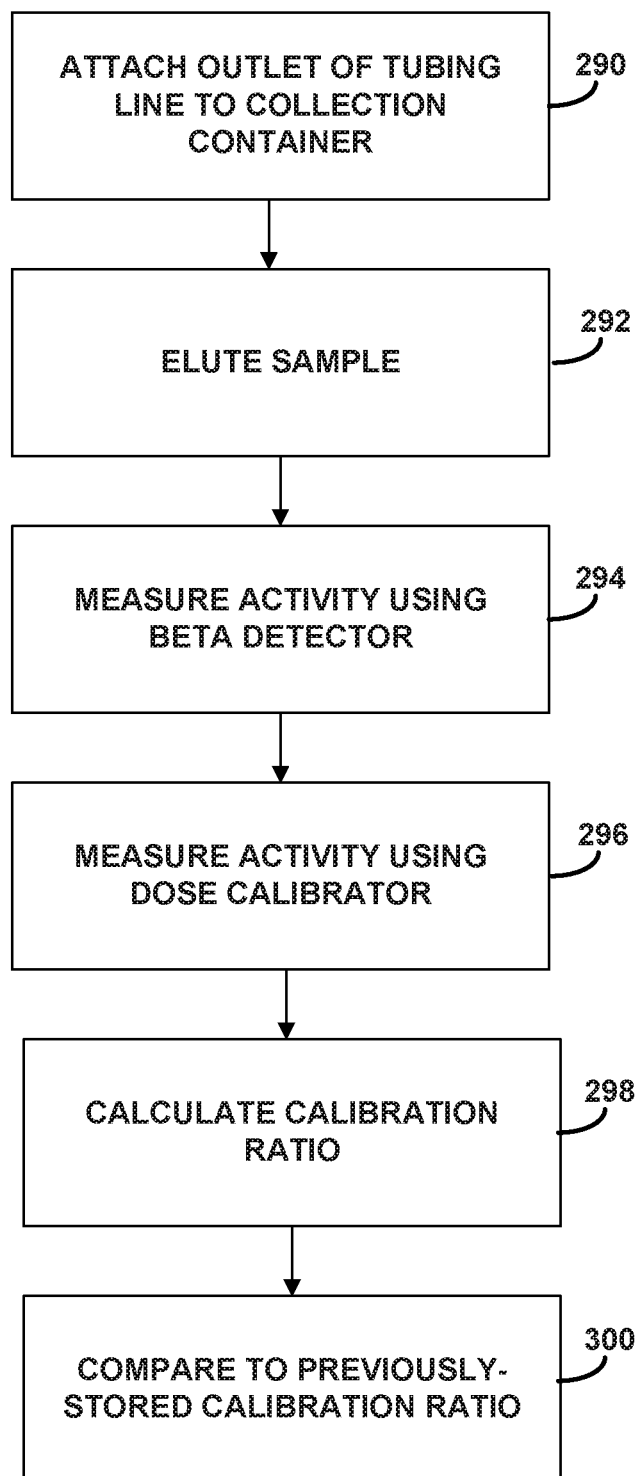

FIG. 14 is a flow diagram of an example technique that may be used to perform a dose calibration using beta detector 58. To perform a calibration according to the example technique, an outlet of infusion tubing line 70 can be attached to an eluate collection container. Eluate-receiving container 56 may be used as the eluate collection container during calibration, or an eluate collection container having a different configuration can be used. For example, the eluate collection container attached to infusion tubing line 70 may be configured to be inserted into third compartment 106 of shielding assembly 28, into another shielded container, and/or directly into a dose calibrator configured to measure the activity of the contents therein.

To perform calibration, controller 80 can control system 10 to deliver radioactive eluate to the eluate collection container (292). The process of initiating the calibration and delivering radioactive eluate to the eluate collection container can follow that described above with respect to FIG. 9 in connection with the quality control evaluation procedure. For example, to initiate the process, an operator may attach infusion tubing line 70 to the eluate collection container and interact with system 10 (e.g., via user interface 16) to elute a sample of radioactive Rb-82 to the container. The eluate collection container may or may not be inserted into a dose calibrator prior to initiating elution.

In some examples, infusion tubing line 70 extends from system 10 to an eluate collection container positioned in a dose calibrator located off board the mobile cart (e.g., on a counter or table adjacent to the cart). In other configurations, system 10 may include an onboard dose calibrator that is contained on the mobile cart and is movable therewith. In either case, controller 80 may receive data generated by the dose calibrator via wired or wireless communication with the dose calibrator and/or via user entry using user interface 16. In some examples, the eluate collection container is positioned in third compartment 106 of shielding assembly 28 and gamma detector 60 is used to generate data for dose calibration.

Once system 10 is suitably arranged to allow the eluate collection container to receive radioactive eluate from radioisotope generator 52, controller 80 can control the system to generate radioactive eluate that is supplied to the eluate collection container. In some examples, controller 80 initiates a calibration elution in response to instructions received via user interface 16 by an operator to perform the calibration elution. For example, controller 80 may execute software that guides the operator through one or more steps to appropriately arrange the components of system 10 for the calibration elution and receives feedback (e.g., via sensors and/or the operator via the user interface) confirming that the components are appropriately arranged before generating radioactive eluate. Controller 80 can control system 10 to execute the calibration elution immediately after arranging the components of system 10 to perform the elution or at a delayed time after the components have been arranged for the calibration elution, as discussed above with respect to the quality control procedure in connection with FIG. 9.

Controller 80 may follow steps 200-208 discussed above with respect to FIG. 8 during a quality control elution to supply radioactive eluate to eluate collection container. Controller 80 can divert radioactive eluate initially generated by radioisotope generator 52 to waste container 54 until the activity of the radioactive eluate as determined via beta emissions measured by beta detector 58 reaches a threshold. Upon the activity of radioactive eluate generated by radioisotope generator 52 reaching the threshold, controller 80 can control multi-way valve 74 to direct the radioactive eluate to eluate collection container. Alternatively, controller 80 may deliver an initial eluted volume of eluate to the eluate collection container without first diverting to waste container 54.

Pump 40 can continue supplying eluant to radioisotope generator 52 and thereby supply radioactive eluate to the eluate collection container until a desired amount of radioactive eluate is supplied to the container. As radioactive eluate flows past the beta detector 58 to the eluate collection container, the beta detector can measure the beta emissions emitted by the radioactive eluate. Controller 80 can determine an activity of the eluate (294), for example by receiving a signal from beta detector 58 indicative of the beta emissions measured by beta detector 58 and may compare a magnitude of the beta emissions measured by the beta detector to calibration information stored in memory relating different beta emission levels to different radioactive eluate activity levels. Controller 80 may determine a cumulative amount of activity delivered to eluate collection container, based on the activity of the radioactive eluate measured by the beta detector and/or the flow rate of the radioactive eluate.

In the technique of FIG. 14, the activity of the eluate delivered to the eluate collection container is also measured by a dose calibrator. The activity of the eluate received by the collection container may be measured continuously from filling of the container through completion of the calibration measurement or at one or more discrete time periods during calibration. For example, the activity of the eluate in the container may be measured following the end of elution, when pump 40 ceases pumping eluant through radioisotope generator 52 to generate eluate or controller 80 controls multi-way valve 74 to direct the radioactive eluate to waste container 54 instead of the eluate collection container. In some examples, the activity of the eluate in the eluate collection container is measured at least once between 1 minute following the end of elution and 10 minutes following the end of elution, such as between 2 minutes following the end of elution and 7 minutes following the end of elution. In different examples, the activity of the eluate may be measured at 2:30, 3:45, or 5:00 minutes after the end of elution.

Controller 80 of system 10 (or another controller) can calculate a calibration ratio based on the cumulative activity of the eluate supplied to the eluate collection container measured by beta detector 58 and the corresponding activity measured by the dose calibrator (e.g., along with the time the activity is measured). The controller may calculate a ratio by dividing the activity measured by the external dose calibrator by the cumulative activity measured by beta detector 58. Controller may adjust the activity measured by the dose calibrator to account for radioactive decay between the time of elution and when the activity measurement was made using information indicative of the amount of time that passed between the end of elution and when the activity measurement was made. The controller may store the calibration ratio in a memory associated with the controller for reference and adjustment of activity measurements made by beta detector 58 during subsequent use.

In some examples, controller 80 compares the calculated calibration ratio to a previously calculated calibration ratio stored in memory (300). The prior calibration ratio may be that which was generated during the calibration test performed immediately prior to the calibration being currently performed. Controller 80 may determine whether the newly-calculated calibration ratio deviates from the previously calculated calibration ratio by more than acceptable threshold. In some examples, system 10 requires the newly-calculated calibration ratio to be within plus or minus 10% of the previously calculated calibration ratio, such as within plus or minus 5% of the previously calculated calibration ratio, within plus or minus 2% of the previously calculated calibration ratio, or within plus or minus 1% of the previously calculated calibration ratio.

If the newly-calculated calibration ratio deviates from the previously calculated calibration ratio by more than the acceptable threshold controller 80 may take action to indicate the discrepancy. In some examples, controller 80 issues a user alert (e.g., via user interface 16) instructing the user to repeat the calibration process. If, after multiple rounds of the performing the calibration procedure, the newly-calculated calibration ratio continues to deviate from the previously calculated calibration ratio (the ratio that was last accepted by the system), controller 80 may issue a user alert instructing the user to contact maintenance personnel, such as a manufacturer representative. Controller 80 may further prohibit continued use of the system and/or a patient infusion procedure until the system has been evaluated by an authorized representative. Controller 80 may provide such a response after at least two rounds of attempted calibration, such as from 2 rounds to 8 rounds, or from 3 rounds to 5 rounds.

In some examples, the calibration technique of FIG. 14 is performed multiple times at different flow rates, and different calibration ratios corresponding to each flow rate are stored in a memory associated with the controller. For example, the calibration technique may be performed once at a comparatively low flow rate, e.g., ranging from 5 ml/min to 35 ml/min, such as from 15 ml/min to 25 ml/min, or at 20 ml/min. The calibration technique may also be performed at a comparatively high flow rate, e.g., ranging from 25 ml/min to 100 ml/min, such as from 40 ml/min to 60 ml/min, or at 50 ml/min. Controller 80 may execute software that guides a user to perform the multiple iterations of calibration and further control pump 40 to pump at the different flow rates during calibration.

Figure 15:
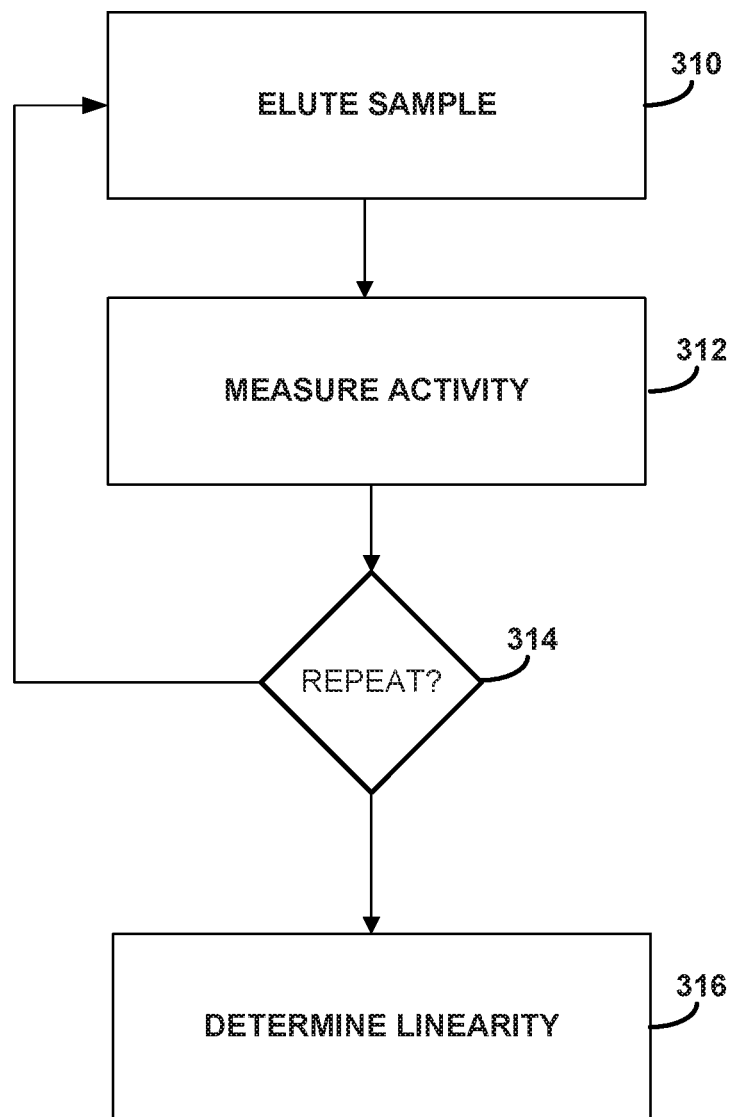

FIG. 15 is a flow diagram of an example technique that may be used to evaluate dose linearity using beta detector 58. Evaluation of dose linearity can determine if beta detector 58 is providing a response that is linearly related to the activity of the sample being measured over the activity range expected to be observed by beta detector 58 during operation.

One embodiment involves evaluating beta detector linearity where multiple calibration sources each having a known activity are placed over beta detector 58. The multiple calibration sources can be selected so each specific calibration source has a different activity level than each other calibration source, providing a range of activities over which beta detector 58 measures beta emissions. The linearity of the activities measured by beta detector 58 can be evaluated to determine the linearity of beta detector 58.

The specific activities of the calibration sources used to evaluate dose linearity using beta detector 58 may be selected to cover the range of activities expected to be observed by the beta detector during normal operation. For example, where system 10 is implemented so beta detector 58 measures a comparatively high level of daughter radioisotope, the calibration sources may be selected to cover the range of daughter radioisotope activity levels expected to be observed during operation. In some examples, the activity of the calibration sources used to measure dose linearity using beta detector 58 may range from 5 mCi to 100 mCi, such as from 10 mCi to 50 mCi, or 15 mCi to 30 mCi.

Another embodiment involves evaluating dose linearity using beta detector 58 where liquid calibration sources are used by flowing the liquid calibration sources through the tubing line positioned adjacent beta detector 58. For example, controller 80 may control system 10 to generate radioactive eluate via radioisotope generator 52 to provide a radioisotope source for testing the dose linearity using beta detector 58 (310). It is appreciated that dose linearity covers contributions from more system components than beta detector linearity.

Controller 80 may follow steps similar to steps 200-208 discussed above with respect to FIG. 8 during a quality control elution to supply radioactive eluate to eluate-receiving container 56. Controller 80 can divert radioactive eluate generated by radioisotope generator 52 and flowing past beta detector 58 during the dose linearity test to waste container 54. Beta detector 58 can measure beta emissions emitted by radioactive eluate flowing through the tubing line positioned adjacent the beta detector (312).

Controller 80 can control system 10 to generate radioactive eluate having different activity levels of daughter radioisotope to perform the dose linearity test (314). The activity of the eluate generated by system 10 may vary during the course of elution as the activity ramps up to a peak bolus and then attenuates to an equilibrium state. In some examples, at three different activity levels of eluate are measured by beta detector 58 during dose linearity testing. One of the activity levels may range from 10 mCi to 20 mCi, such as 15 mCi. A second of the activity levels may range from 20 mCi to 40 mCi, such as 30 mCi. A third of the activity levels may range from 50 mCi to 100 mCi, such as 60 mCi. Additional or different activity levels may be used for dose linearity testing.

Beta detector 58 may measure the activity of the calibration sources and/or eluate samples at different activity levels and the measured activity can be stored in a memory associated with controller 80. After measuring the activity levels of a suitable number of calibration sources and/or samples, the technique of FIG. 15 involves linearly regressing the data and determining an R-squared value for the measured activity values (316). R-squared is a statistical measure of how close the data are to a fitted regression line. Controller 80 may determine an R-squared value for the measured activity values of the different calibration sources. Controller 80 may further compare the determined R-squared value to a threshold stored in memory. In some examples, the threshold may require the R-squared value be greater than 80%, such as greater than 90%, greater than 95%, or greater than 98%. If controller 80 determines that the R-squared value is below the required threshold, the controller may take action to indicate that beta detector 58 is not producing sufficiently linear results. In some examples, controller 80 issues a user alert (e.g., via user interface 16) informing an operator that beta detector 58 is not producing sufficiently linear results.

In some examples where eluate samples having different activity levels are used for dose linearity testing, the testing process may be performed multiple times at different flow rates. For example, the dose linearity testing technique may be performed once at a comparatively low flow rate, e.g., ranging from 5 ml/min to 35 ml/min, such as from 15 ml/min to 25 ml/min, or at 20 ml/min. The dose linearity testing technique may also be performed at a comparatively high flow rate, e.g., ranging from 25 ml/min to 100 ml/min, such as from 40 ml/min to 60 ml/min, or at 50 ml/min. Controller 80 may execute software that guides a user to perform the multiple iterations of the dose linearity testing and further control pump 40 to pump at the different flow rates during testing.

Figure 16:
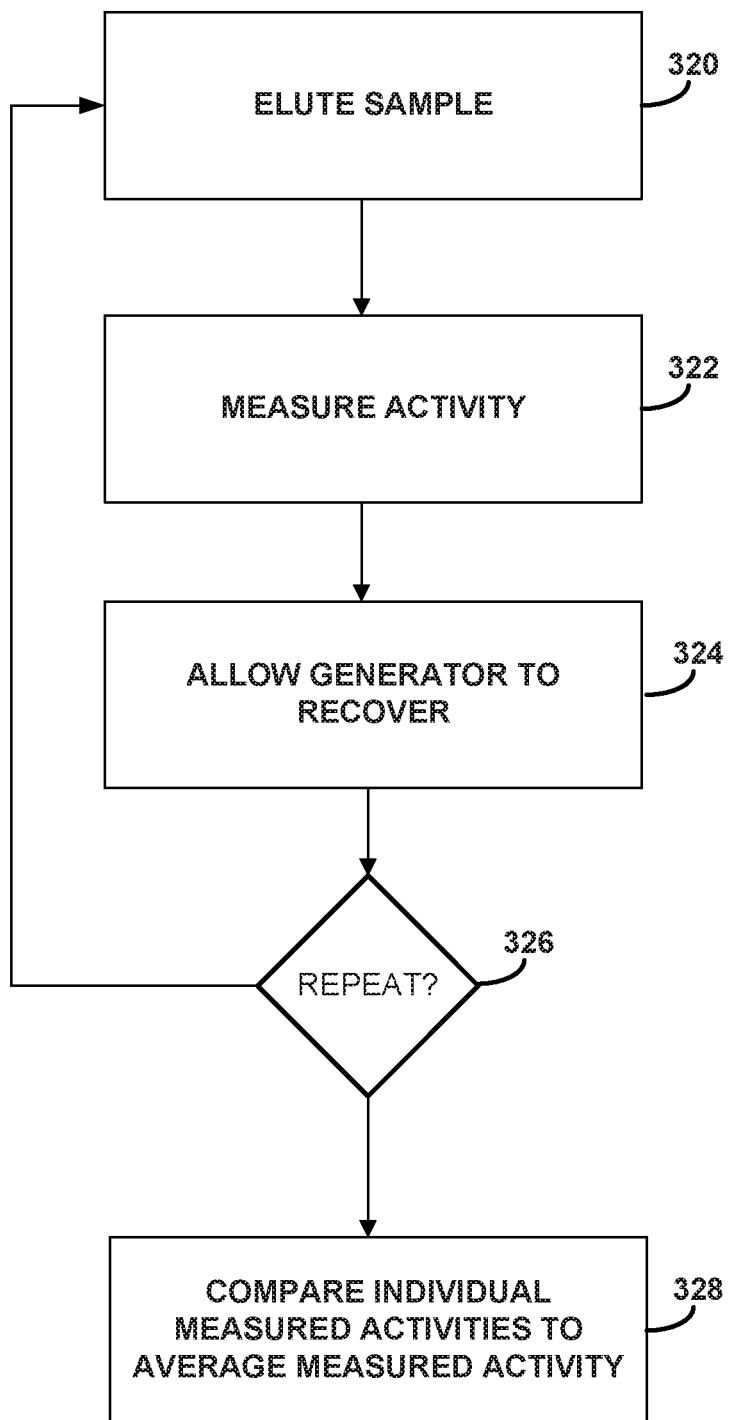

FIG. 16 is a flow diagram of an example technique that may be used to evaluate the repeatability or precision of activity measurements made by beta detector 58. The technique of FIG. 16 may be used by system 10 to evaluate whether beta detector 58 is providing consistent and repeatable activity measurements across multiple sample acquisitions of a sample at the same activity level.

In the technique of FIG. 16, a dose repeatability test may be performed using beta detector 58 by repeatedly exposing the beta detector to the same calibration source having a known level of activity. A liquid calibration source may be passed through the tubing line positioned adjacent beta detector 58. For example, controller 80 may control system 10 to generate radioactive eluate via radioisotope generator 52 to provide a radioisotope source for testing the constancy of beta detector 58 (320).

Controller 80 may follow steps similar to steps 200-208 discussed above with respect to FIG. 8 during a quality control elution to supply radioactive eluate to eluate-receiving container 56. Controller 80 can divert radioactive eluate generated by radioisotope generator 52 and flowing past beta detector 58 during the constancy test to waste container 54. Beta detector 58 can measure beta emissions emitted by radioactive eluate flowing through the tubing line positioned adjacent the beta detector (322).

The target activity of the radioactive eluate flowing through the tubing line may range from 10 mCi to 100 mCi, such as from 20 mCi to 50 mCi, or from 25 mCi to 35 mCi. For example, the target activity level may be 30 mCi, although other activity levels can be used. The radioactive eluate may be supplied at flow rates ranging from 5 ml/min to 100 ml/min, such as from 20 ml/min to 50 ml/min, although other flow rates can be used.

After detecting beta emissions emanating from the eluate flowing through the tubing line, controller 80 may determine the activity of the calibration eluate (322). Controller 80 can cease generating radioactive eluate and wait a period of time sufficient to allow radioisotope generator 52 to recover (324). Thereafter, controller 80 can again control system 10 to generate radioactive eluate having the same target activity as that generated initially during constancy testing (326). System 10 may generate, and beta detector 58 may measure, at least two samples of eluate having the target activity, such as at least 5, or at least 10. For example, system 10 may generate, and beta detector 58 may measure, from 2 to 20 samples, such as from 5 to 15 samples.

After measuring the activity of repeated samples a desired number of times, the technique of FIG. 16 includes comparing each measured activity to an average of multiple of the measured calibration activities (328). In some examples, controller 80 determines an average (e.g., mean, median) measured activity of the calibration sample based on all of the measurements made during the test. Controller 80 may further compare each individual measured activity determined during the test to the average measured activity and determine if any one measured activity deviates from the average measured activity by more than acceptable threshold. In some examples, the acceptable threshold may be within plus or minus 10% of the average measured activity, such as within plus or minus 5% of the average measured activity, or within plus or minus 2% of the average measured activity.

If controller 80 determines that any one of the plurality of measured activities exceeds the average measured activity by more than the acceptable threshold, the controller may take action to indicate that beta detector 58 is not producing sufficiently repeatable results. In some examples, controller 80 issues a user alert (e.g., via user interface 16) informing an operator that beta detector 58 is not producing sufficiently repeatable results.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), magnetoresistive random access memory (MRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following examples may provide additional details about radioisotope delivery systems in accordance with the disclosure.

Example 1

Sr-82 and Sr-85 samples covering the range of activity levels that may be observed during operation of a strontium-rubidium radioisotope generator were compared using three exemplary measurement systems: a CZT gamma detector, a dose Calibrator, and a high-purity germanium gamma detector (HPGe). Ten activity readings were made across the range of activity levels for each of the detectors. The results are presented in Table 1 below.

TABLE 1

Comparison of measurements by the three detector systems

| | HPGe Gamma Detector | | | | Sr-82 Level[#] Ratio | CZT Gamma Detector | | | | Dose Calibrator | | | |
|---|---|---|---|---|---|---|---|---|---|---|---|---|---|
| | Sr-82 | | Sr-85 | | μCi/mCi | Sr-82 | | | Sr-85 | Reading | Sr-82 | | Sr-85 |
| ID | μCi | % CV** | μCi | % CV | Rb-82 | μCi | Error %* | % CV** | μCi | μCi | μCi | % Error* | μCi |
| 1 | 7.0488 | 0.5 | 10.4061 | 0.1 | 0.2350 | 6.211 | 11.89 | 0.31 | 9.080 | 11.19 | 6.58 | 6.71 | 9.61 |
| 2 | 3.4297 | 0.7 | 5.0836 | 0.2 | 0.1143 | 3.098 | 9.67 | 0.44 | 4.529 | 5.63 | 3.31 | 3.54 | 4.84 |
| 3 | 0.7645 | 1.5 | 1.1258 | 0.4 | 0.0255 | 0.709 | 7.26 | 0.93 | 1.037 | 1.25 | 0.73 | 3.92 | 1.07 |
| 4 | 0.4285 | 2.0 | 0.6219 | 0.5 | 0.0143 | 0.39 | 8.98 | 1.25 | 0.570 | 0.74 | 0.43 | −1.48 | 0.64 |
| 5 | 0.2450 | 2.6 | 0.3506 | 0.7 | 0.0082 | 0.223 | 8.98 | 1.64 | 0.326 | 0.38 | 0.22 | 8.86 | 0.33 |
| 6 | 0.1420 | 3.4 | 0.2085 | 0.8 | 0.0047 | 0.131 | 7.75 | 2.14 | 0.192 | 0.24 | 0.14 | 0.68 | 0.21 |
| 7 | 0.0791 | 4.6 | 0.1142 | 1.1 | 0.0026 | 0.069 | 12.77 | 2.91 | 0.101 | 0.11 | 0.06 | 18.28 | 0.09 |
| 8 | 0.0501 | 5.8 | 0.0735 | 1.4 | 0.0017 | 0.044 | 12.18 | 3.62 | 0.064 | 0.06 | 0.04 | 29.63 | 0.05 |
| 9 | 0.0280 | 5.9 | 0.0421 | 1.4 | 0.0009 | 0.027 | 3.50 | 4.51 | 0.039 | 0.03 | 0.02 | 37.00 | 0.03 |
| 10 | 0.0152 | 5.7 | 0.0240 | 1.3 | 0.0005 | 0.015 | 1.48 | 5.87 | 0.022 | 0.03 | 0.02 | −15.78 | 0.03 |
| 11 | 0.0110 | 5.5 | 0.0160 | 1.3 | 0.0004 | 0.009 | 18.43 | 6.97 | 0.013 | 0.01 | 0.01 | 46.74 | 0.01 |
| 12 | 0.0104 | 4.9 | 0.0104 | 1.4 | 0.0003 | 0.006 | 42.21 | 8.25 | 0.009 | 0.04 | 0.02 | −126.38 | 0.03 |

**CV $= \left( \frac{\sqrt{\text{Net Counts}}}{\text{Net Counts}} \right) \times 100$, [#]Based on 30 mCi Rb−82, *% Error $= \frac{(\text{HPGE} - \text{DC or CZT})}{\text{HPGe}} \times 100$ The date in Table 1 were interpreted relative to three exemplary ratios or limits, designated an alert limit, and expiry limit, and a legal limit. For Sr-82, the values corresponding to these limits for purposes of the experiment 0.002, 0.01, and 0.02 μCi Sr-82 per mCi of Rb-82, respectively. For Sr-85, the values corresponding to these limits for purposes of the experiment were ten-fold higher than the Sr-82 limits, or 0.02, 0.1, and 0.2 μCi Sr-85 per mCi of Rb-82, respectively. The ten-fold increase corresponds to a maximum ratio of Sr-85/Sr-82 of 10.

Samples were measured with the CZT detector using a 600 second acquisition. Background radiation was measured before the samples and corrected automatically by the infusion system for each strontium activity calculation. The % CV for the CZT detector data (Sr-82/85) was determined based on net counts and was <4% down to and including the Alert Limit (0.002) or a total Sr-82/85 content of 0.1 μCi and still only approximately 8% at a ratio of 0.0003 almost 10-fold lower.

Counting times for the HPGe detector were adjusted to obtain good counting statistics with a maximum CV of approximately 6%. The Sr85/82 ratio of 1.462 corresponded approximately that of the example Sr/Rb generator used for the experiment at the end of its 42-day life starting from an initial ratio of <1. The higher proportion of Sr-85 leads to more counts than for Sr-82 and the lower CVs seen in Table 1.

For the dose calibrator, the reading of each sample was allowed to stabilize for approximately 30 second before recording the result.

The data show that both the dose calibrator and the CZT detector were able to accurately measure Sr82/85 radioactivity levels down to below the Expiry Limit (ratio 0.01). However, whereas the CZT detector still exhibited an acceptable error down to a ratio of 0.0004 the Dose Calibrator exhibited unacceptable error at 0.0017, just below the Alert Limit, under the experimental conditions used. Any apparent errors in the readings provided by the CZT detector were uniform down to the second lowest sample but all positive, which suggests good precision but inaccuracy due to insufficient calibration. The errors of the dose calibrator were larger at lower levels and both positive and negative, suggesting accuracy at higher levels but a lack of precision at lower levels.

The data show that the CZT detector made precise measurements down to radioactivity levels well below those encountered at the Alert Limit while the dose calibrator lacked precision at radioactivity levels at or lower than the Alert Limit. This is consistent with counting statistics (indicating that sufficient counts are being recorded to achieve a desired precision). A dose calibrator may have a limited measurement resolution of only 0.01 μCi. This is typically caused by the resolution of the display, which cause rounding or truncation errors. Independent of and additive to any inherent uncertainty in the measurement, the minimum change that can be registered with dose calibrators exhibiting such precision for a total Sr-82/85 dose of 0.06+0.01 μCi at the Alert Limit for 30 mCi Rb-82 is plus or minus 17%.

The data show that the CZT used in the example was more precise than the dose calibrator at Sr-82/85 levels encountered near the Alert Limit.

The invention claimed is:

1. An infusion system comprising:
   a frame that carries a beta detector, a gamma detector, and a controller communicatively coupled to the beta detector and the gamma detector,
   wherein the frame is further configured to receive a strontium-rubidium radioisotope generator that generates a radioactive eluate via elution,
   the beta detector is positioned to measure beta emissions emitted from the radioactive eluate,
   the gamma detector is positioned to measure gamma emissions emitted from the radioactive eluate, and
   the controller is configured to determine an activity of rubidium in the radioactive eluate based on the beta emissions measured by the beta detector and determine an activity of strontium in the radioactive eluate based on the gamma emissions measured by the gamma detector.

2. The infusion system of claim 1, wherein the gamma detector is positioned to measure the gamma emissions emitted from a static portion of the radioactive eluate.

3. The infusion system of claim 1, wherein the controller is configured to control the infusion system to prevent a patient infusion procedure if the determined activity of strontium exceeds an allowable limit.

4. The infusion system of claim 1, further comprising an infusion tubing line configured to receive the radioactive eluate, either directly or indirectly, from the strontium-rubidium radioisotope generator, when the strontium-rubidium radioisotope generator is received by the frame.

5. The infusion system of claim 4, further comprising an eluate-receiving container in fluid communication with the infusion tubing line to receive a portion of the radioactive eluate, thereby providing a static portion of the radioactive eluate.

6. The infusion system of claim 5,
wherein the beta detector is positioned to measure the beta emissions emitted from the radioactive eluate flowing through the infusion tubing line; and
the gamma detector is positioned to measure the gamma emissions emitted from the static portion of the radioactive eluate in the eluate-receiving container.

7. The infusion system of claim 5, wherein the eluate-receiving container comprises a vial, the infusion tubing line comprises a needle at an end of the infusion tubing line, and the needle on the infusion tubing line is inserted into the vial.

8. The infusion system of claim 5, further comprising a waste container.

9. The infusion system of claim 1, further comprising the strontium-rubidium radioisotope generator received by the frame, wherein the strontium-rubidium radioisotope generator is configured to generate the radioactive eluate containing rubidium-82 via elution of a column containing strontium-82.

10. The infusion system of claim 9, further comprising:
an eluant reservoir containing an eluant;
a pump coupled to the eluant reservoir via an eluant line;
an eluate-receiving container carried by the frame;
a waste container carried by the frame; and
an infusion tubing circuit that includes an infusion tubing line, an eluate line, a waste line, and a multi-way divergence valve, wherein the infusion tubing line is in fluid communication with the eluate line via the multi-way divergence valve and the waste line is in fluid communication with the eluate line via the multi-way divergence valve,
wherein the beta detector is positioned to measure the beta emissions from the radioactive eluate flowing through the eluate line, and the gamma detector is configured to measure the gamma emissions from a static portion of the radioactive eluate in the eluate-receiving container and received from the infusion tubing line.

11. The infusion system of claim 10, wherein
the controller is communicatively coupled to the multi-way divergence valve and configured to control flow from the eluate line to a select one of the infusion tubing line and the waste line via the multi-way divergence valve; and
the controller is further configured during a quality control process to:
control the pump to pump the eluant through the strontium-rubidium radioisotope generator and generate the radioactive eluate,
determine a radioactive activity of the radioactive eluate based on the beta emissions measured via the beta detector while the radioactive eluate is directed to the waste container,
upon the radioactive activity of the radioactive eluate reaching a threshold level of rubidium activity, control the multi-way divergence valve to place the infusion tubing line in fluid communication with the eluate line,
further control the pump to fill the eluate-receiving container with the radioactive eluate,
control the gamma detector to detect the gamma emissions from the radioactive eluate in the eluate-receiving container after a period of time sufficient for substantially all rubidium in the radioactive eluate to decay, and
determine the activity of strontium in the eluate-receiving container based on the gamma emissions measured by the gamma detector.

12. The infusion system of claim 11, wherein the controller is further configured to compare the determined activity of strontium to an allowable limit and control the infusion system to prevent a patient infusion procedure if the determined activity of strontium exceeds the allowable limit.

13. The infusion system of claim 11, wherein the threshold level of rubidium activity ranges from 5% to 15% of a maximum rubidium activity detected during the immediate prior quality control process.

14. The infusion system of claim 11, wherein the threshold level of rubidium activity is between 8% and 12% of a maximum rubidium activity detected during the immediate prior quality control process.

15. The infusion system of claim 11, wherein the threshold level of rubidium activity is about 10% of a maximum rubidium activity detected during the immediate prior quality control process.

16. The infusion system of claim 10, wherein the controller is communicatively coupled to the multi-way divergence valve and configured to control flow from the eluate line to a select one of the infusion tubing line and the waste line via the multi-way divergence valve; and
the controller is further configured to:
control the pump to pump the eluant through the strontium-rubidium radioisotope generator and generate the radioactive eluate flowing through the eluate line to the waste line and the waste container,
control the beta detector to measure the beta emissions from the radioactive eluate flowing through the eluate line to the waste line and determine therefrom the activity of the radioactive eluate;
upon the activity of the radioactive eluate reaching a threshold level, control the multi-way divergence valve to place the infusion tubing line in fluid communication with the eluate line,
control the beta detector to measure the beta emissions from the radioactive eluate flowing through the eluate line to the eluate-receiving container via the infusion tubing line and determine therefrom an accumulated rubidium radioactive dose supplied to the eluate-receiving container,
upon determining that the accumulated rubidium radioactive dose has reached a Quality Control (QC) threshold level, control the pump to cease pumping the eluant through the strontium-rubidium radioisotope generator, thereby establishing a time from which an end of filling of the eluate-receiving container is measured,
control the gamma detector to measure the gamma emissions from the radioactive eluate in the eluate-receiving container within a constancy time window after the end of filling of the eluate-receiving container and determine therefrom an accumulated constancy gamma activity, and calculate a constancy ratio based on the accumulated rubidium radioactive dose supplied to the eluate-receiving container and the accumulated constancy gamma activity.

17. The infusion system of claim 16, wherein the controller is configured to calculate the constancy ratio by at least dividing the accumulated rubidium radioactive dose supplied to the eluate-receiving container by the accumulated constancy gamma activity.

18. The infusion system of claim 16, wherein the controller is configured to compare the constancy ratio to a reference constancy ratio and determine if the constancy ratio deviates from the reference constancy ratio by more than a tolerable range.

19. The infusion system of claim 16, wherein the controller is configured to issue an user alert or initiate recalibration of the infusion system if the constancy ratio deviates from a reference constancy ratio by more than a tolerable range.

20. The infusion system of claim 19, wherein the controller is configured to recalibrate with a rubidium activity measurement made using a dose calibrator during recalibration.

21. The infusion system of claim 19, wherein the controller is configured to recalibrate using a rubidium activity measurement made with the gamma detector during recalibration.

22. The infusion system of claim 10, wherein the controller is communicatively coupled to the multi-way divergence valve and configured to control flow from the eluate line to a select one of the infusion tubing line and the waste line via the multi-way divergence valve; and the controller is further configured to:
control the pump to pump the eluant through the strontium-rubidium radioisotope generator and generate the radioactive eluate flowing through the eluate line to the waste line and the waste container,
control the beta detector to measure the beta emissions from the radioactive eluate flowing through the eluate line to the waste line and determine therefrom the activity of the radioactive eluate;
upon the activity of the radioactive eluate reaching a threshold level, control the multi-way divergence valve to place the infusion tubing line in fluid communication with the eluate line,
control the beta detector to measure the beta emissions from the radioactive eluate flowing through the eluate line to the eluate-receiving container via the infusion tubing line and determine therefrom an accumulated rubidium radioactive dose supplied to the eluate-receiving container,
determine a total volume of the radioactive eluate flowing to the eluate-receiving container,
upon determining that the total volume of the radioactive eluate flowing to the eluate-receiving container has reached a QC threshold volume, control the pump to cease pumping the eluant through the strontium-rubidium radioisotope generator, thereby establishing a time from which an end of filling of the eluate-receiving container is measured,
control the gamma detector to measure the gamma emissions from the radioactive eluate in the eluate-receiving container within a constancy time window after the end of filling of the eluate-receiving container and determine therefrom an accumulated constancy gamma activity, and
calculate a constancy ratio based on the accumulated rubidium radioactive dose supplied to the eluate-receiving container and the accumulated constancy gamma activity.

23. The infusion system of claim 1, wherein the controller is configured to determine a cumulative volume of the radioactive eluate generated by the radioisotope generator, when installed in the infusion system.

24. The infusion system of claim 23, wherein the controller is configured to control the infusion system to prevent a patient infusion procedure if the cumulative volume of the radioactive eluate exceeds an allowable limit.

25. A method comprising:
pumping an eluant through a strontium-rubidium radioisotope generator and thereby generating a radioactive eluate via elution;
conveying the radioactive eluate across a beta detector and measuring beta emissions emitted from the radioactive eluate generated by the radioisotope generator and flowing through an eluate line and determining therefrom an activity of the radioactive eluate;
receiving the radioactive eluate conveyed across the beta detector in an eluate-receiving container positioned adjacent a gamma detector; and
measuring gamma emissions emitted from the radioactive eluate received by the eluate-receiving container and determining therefrom an activity of strontium in the radioactive eluate in the eluate-receiving container.

26. The method of claim 25, wherein the radioactive eluate received by the eluate-receiving container provides a static portion of the radioactive eluate from which the gamma emissions are measured.

27. The method of claim 25, wherein conveying the radioactive eluate across the beta detector comprises conveying the radioactive eluate through tubing positioned in front of the beta detector and in fluid communication with a waste container until the activity of the radioactive eluate exceeds a threshold and then diverting the flow of the radioactive eluate to the eluate-receiving container.

28. The method of claim 25, further comprising, prior to measuring the gamma emissions emitted from the radioactive eluate received by the eluate-receiving container, holding the radioactive eluate in the eluate-receiving container an amount of time sufficient to allow substantially all rubidium-82 initially present in the radioactive eluate to decay.

29. The method of claim 25, further comprising comparing the determined activity of strontium to a breakthrough threshold and preventing a patient infusion procedure if the determined activity of strontium exceeds the breakthrough threshold.

30. The method of claim 25, wherein
conveying the radioactive eluate across the beta detector comprises conveying the radioactive eluate through tubing positioned in front of the beta detector and in fluid communication with a waste container until the activity of the radioactive eluate exceeds a threshold and then diverting the flow of the radioactive eluate to the eluate-receiving container;

measuring the beta emissions emitted from the radioactive eluate generated by the radioisotope generator comprises measuring the beta emissions from the radioactive eluate flowing through the eluate line to the eluate-receiving container and determining therefrom an accumulated rubidium radioactive dose supplied to the eluate-receiving container; and measuring the gamma emissions emitted from the radioactive eluate received by the eluate-receiving container comprises measuring the gamma emissions emitted from the radioactive eluate in the eluate-receiving container within a constancy time window after the end of filling of the eluate-receiving container and determining therefrom an accumulated constancy gamma activity.

31. The method of claim 30, further comprising calculating a constancy ratio based on the accumulated rubidium radioactive dose supplied to the eluate-receiving container and the accumulated constancy gamma activity.

32. The method of claim 31, further comprising comparing the constancy ratio to a reference constancy ratio and determining if the constancy ratio deviates from the reference constancy ratio by more than a tolerable range.

33. The method of claim 32, further comprising recalibrating the beta detector if the constancy ratio deviates from the reference constancy ratio by more than the tolerable range.

34. The method of claim 33, wherein recalibrating the beta detector comprises recalibrating the beta detector with a dose calibrator.

35. The method of claim 33, wherein recalibrating the beta detector comprises recalibrating the beta detector using measurements of gamma emissions emitted from the radioactive eluate received by the eluate-receiving container.

36. The method of claim 30, wherein the constancy time window ranges from 700 seconds to 1000 seconds from the end of filling of the eluate-receiving container.

37. The method of claim 25, wherein the gamma detector comprises a solid state gamma detector and the beta detector comprises a scintillator and photomultiplier.

38. The method of claim 25, wherein pumping the eluant through the strontium-rubidium radioisotope generator comprises pumping saline at a rate ranging from 5 ml/min to 100 ml/min.

\* \* \* \* \*